(12) United States Patent
Yan et al.

(10) Patent No.: US 8,884,013 B2
(45) Date of Patent: Nov. 11, 2014

(54) POLYMORPHS OF DASATINIB, PREPARATION METHODS AND PHARMACEUTICAL COMPOSITIONS THEREOF

(75) Inventors: Rong Yan, Jiangsu (CN); Hao Yang, Jiangsu (CN); Yongxiang Xu, Jiangsu (CN)

(73) Assignees: Nan Jing Cavendish Bio-Engineering Technology Co., Ltd., Jiangsu (CN); Rong Yan, Jiangsu (CN)

( * ) Notice: Subject to any disclaimer, the term of this patent is extended or adjusted under 35 U.S.C. 154(b) by 0 days.

(21) Appl. No.: 13/577,624

(22) PCT Filed: Jan. 31, 2011

(86) PCT No.: PCT/CN2011/000185
§ 371 (c)(1),
(2), (4) Date: Aug. 7, 2012

(87) PCT Pub. No.: WO2011/095059
PCT Pub. Date: Aug. 11, 2011

(65) Prior Publication Data
US 2012/0309968 A1 Dec. 6, 2012

(30) Foreign Application Priority Data
Feb. 8, 2010 (CN) .......................... 2010 1 9026056

(51) Int. Cl.
| | | |
|---|---|---|
| C07D 403/00 | (2006.01) | |
| A61K 9/20 | (2006.01) | |
| A61K 9/48 | (2006.01) | |
| A61K 31/506 | (2006.01) | |
| C07D 417/12 | (2006.01) | |

(52) U.S. Cl.
CPC ............ *A61K 9/2018* (2013.01); *A61K 9/2054* (2013.01); *A61K 9/4866* (2013.01); *A61K 31/506* (2013.01); *A61K 9/2027* (2013.01); *A61K 9/4858* (2013.01); *C07D 417/12* (2013.01); *A61K 9/2059* (2013.01)
USPC ........................................................ 544/295

(58) Field of Classification Search
USPC ................. 544/328, 295; 514/252.14, 259.19
See application file for complete search history.

(56) References Cited

U.S. PATENT DOCUMENTS

| | | | |
|---|---|---|---|
| 7,491,725 B2 * | 2/2009 | Lajeunesse et al. | 514/252.19 |
| 2007/0105867 A1 * | 5/2007 | Chidambaram et al. | 514/252.19 |
| 2009/0093495 A1 * | 4/2009 | Lee | 514/252.18 |

FOREIGN PATENT DOCUMENTS

| | | | |
|---|---|---|---|
| CN | 1980909 A | | 6/2007 |
| CN | 101170996 A | | 4/2008 |
| CN | 101812060 A | | 8/2010 |
| CN | 101845045 A | | 9/2010 |
| CN | 101891738 A | | 11/2010 |
| CN | 102086195 A | * | 6/2011 |
| WO | 2004085388 A2 | | 10/2004 |
| WO | 2009053854 A2 | | 4/2009 |
| WO | WO 2009053854 A2 | * | 4/2009 |
| WO | WO 2010062715 A2 | * | 6/2010 |
| WO | WO 2010067374 A2 | * | 6/2010 |
| WO | WO 2010139979 A2 | * | 12/2010 |
| WO | WO 2010139980 A1 | * | 12/2010 |
| WO | WO 2010139981 A2 | * | 12/2010 |

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
H.G. Brittain, Preparation and Identification of Polymorphs and Solvatomorphs in, Preformulation in Solid Dosage Form Development, 185-228 (5th ed., M. C. Adeyeye et al., eds., 2008).*
International Search Report dated May 5, 2011 from International Patent Application No. PCT/CN2011/000185 filed Jan. 31, 2011 (12 pages).
Zang Jialiang et al., "Synthesis of Dasatinib", Chinese Journal of Pharmaceuticals, 2009, vol. 40, No. 5, pp. 321-323.
Wang, Wei, et al. Study of synthetic process of dasatinib, Chinese Journal of Medicinal Chemistry, Feb. 2009, vol. 19, No. 1, pp. 36-38.

* cited by examiner

*Primary Examiner* — James O. Wilson
*Assistant Examiner* — Alexander R Pagano
(74) *Attorney, Agent, or Firm* — Sunstone IP

(57) ABSTRACT

Polymorph I of dasatinib monohydrate and Polymorph II of dasatinib, their preparation methods and pharmaceutical compositions containing the same are provided. These polymorphs have better physicochemical properties, are more stable and are more suitable for industrial scale production.

10 Claims, 40 Drawing Sheets

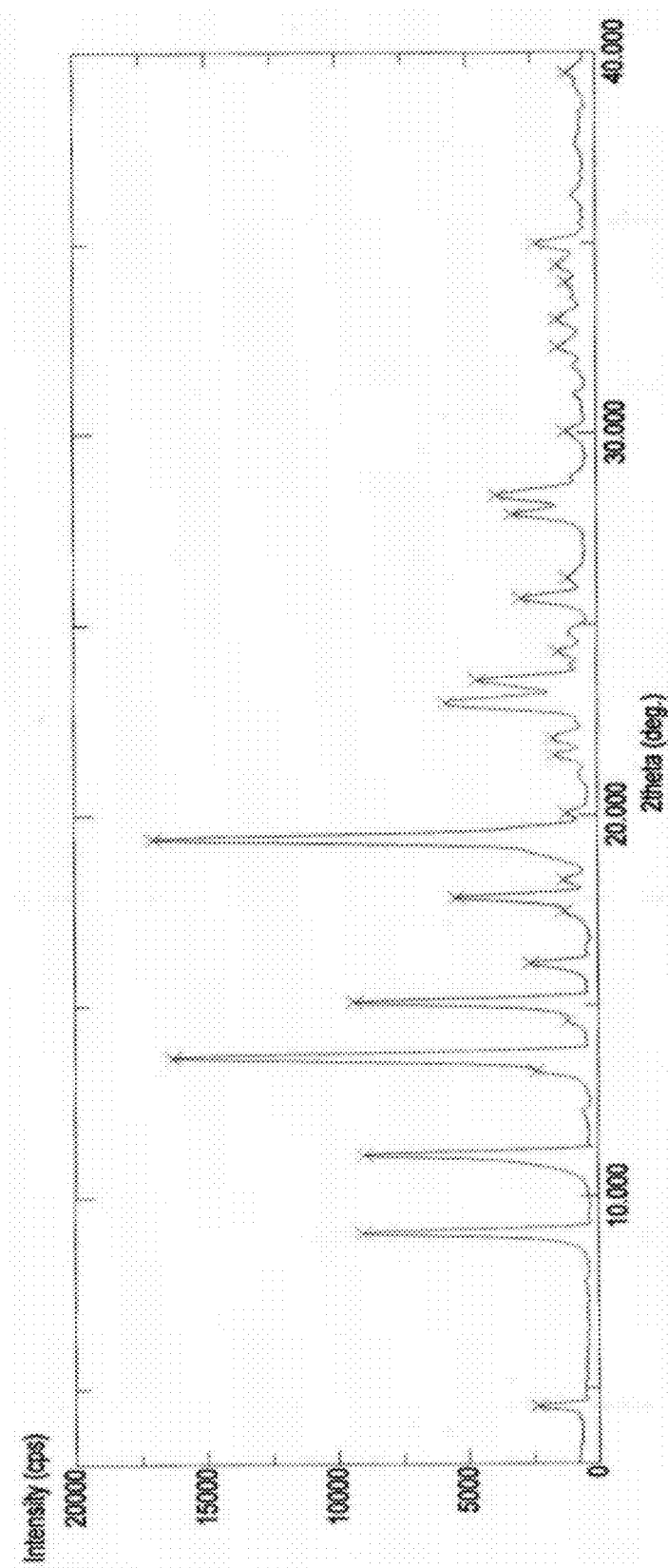

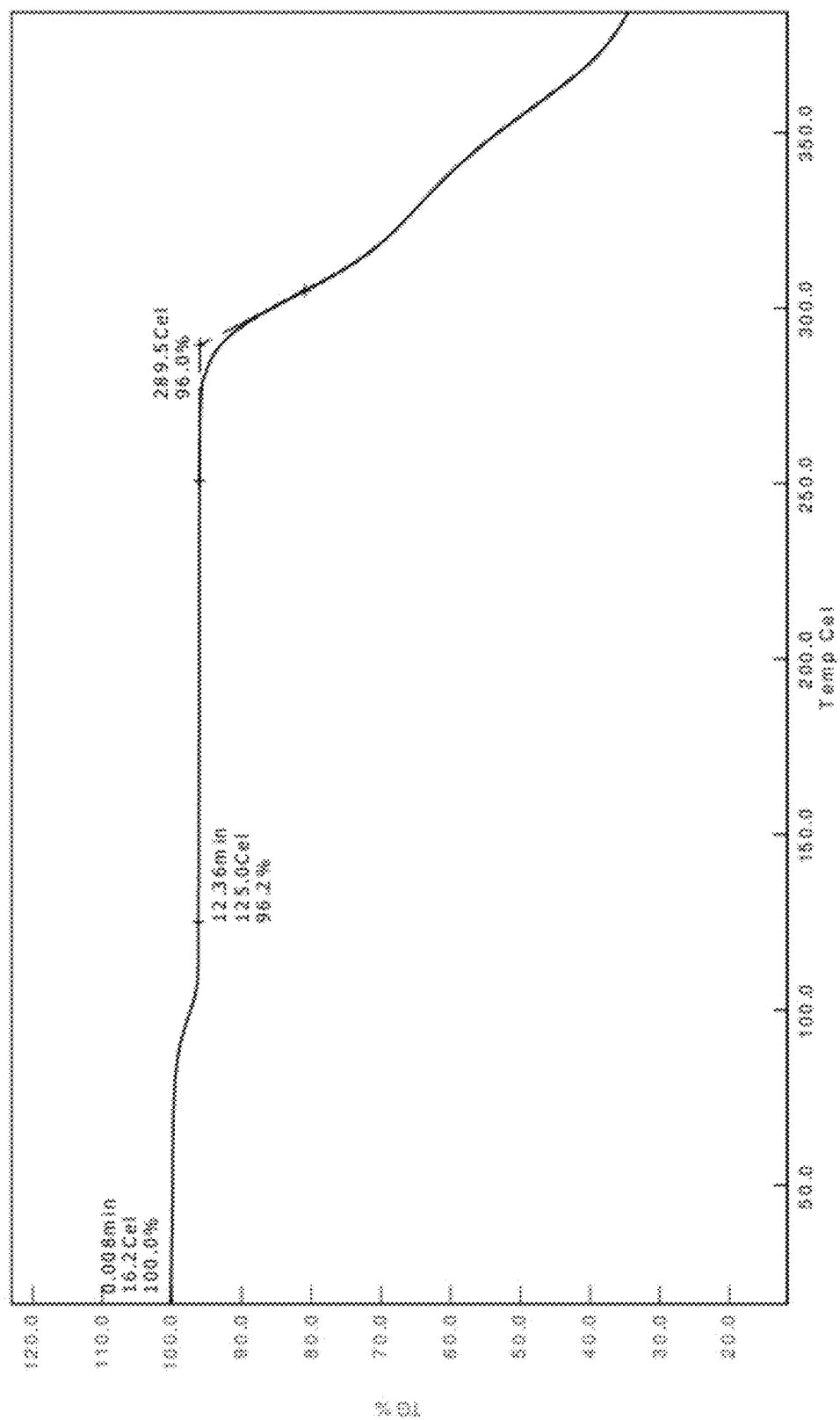

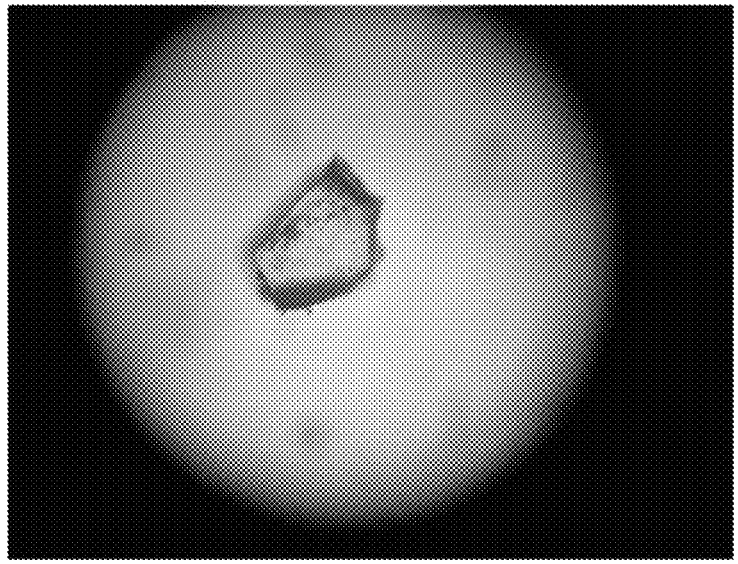
A
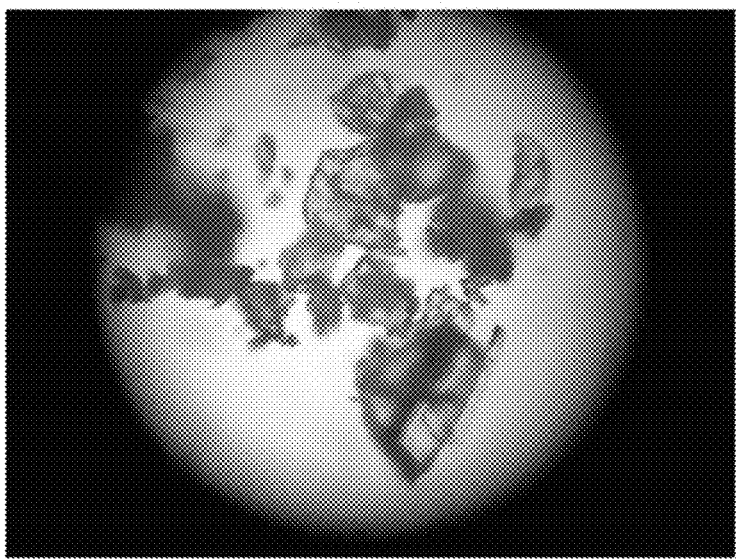
B
Fig. 14

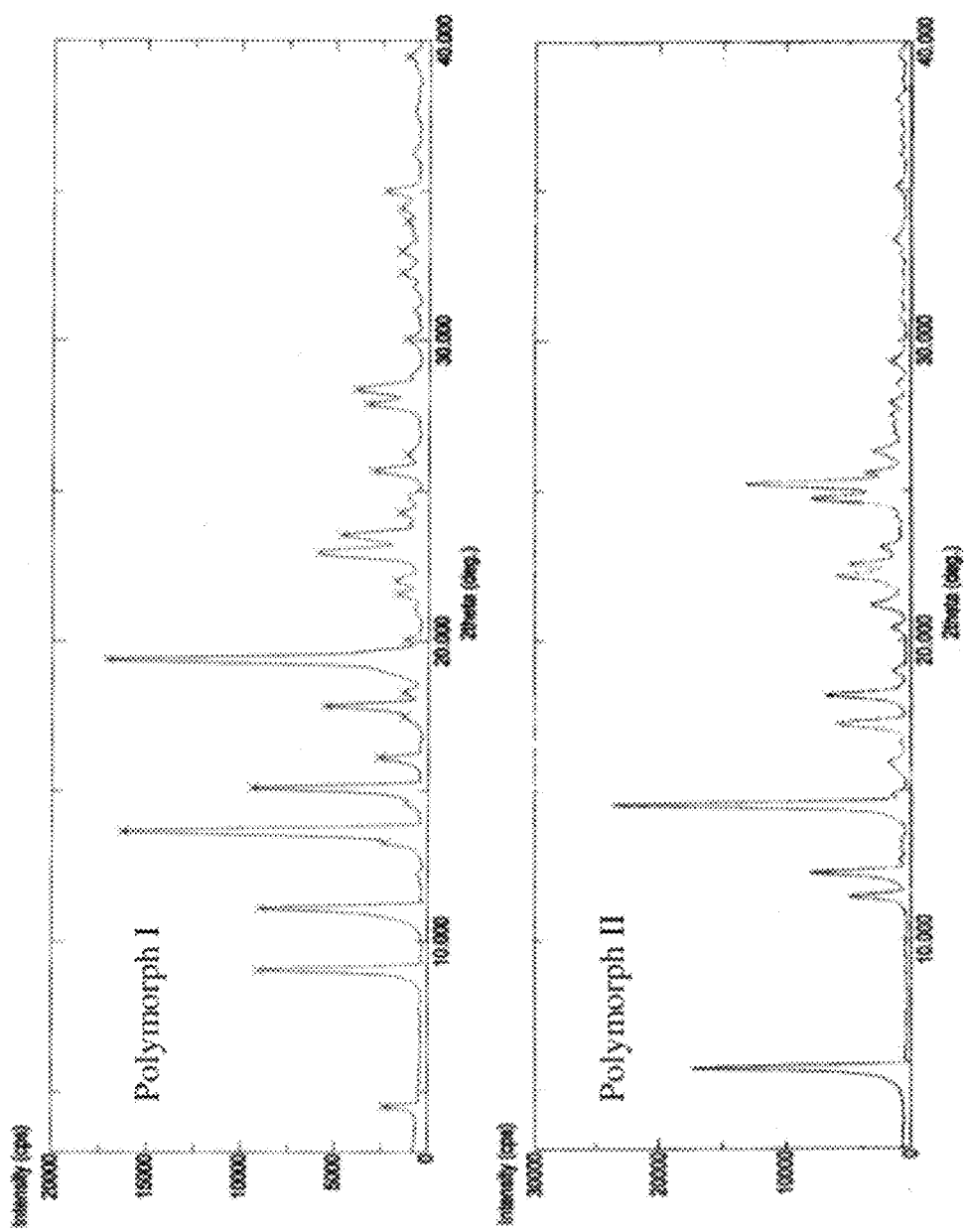

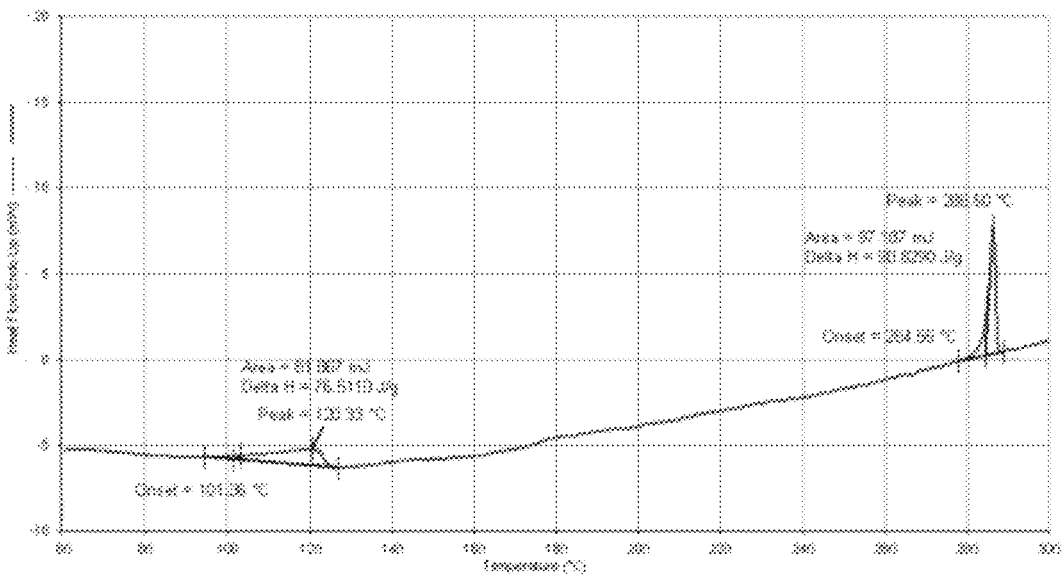
Polymorph I
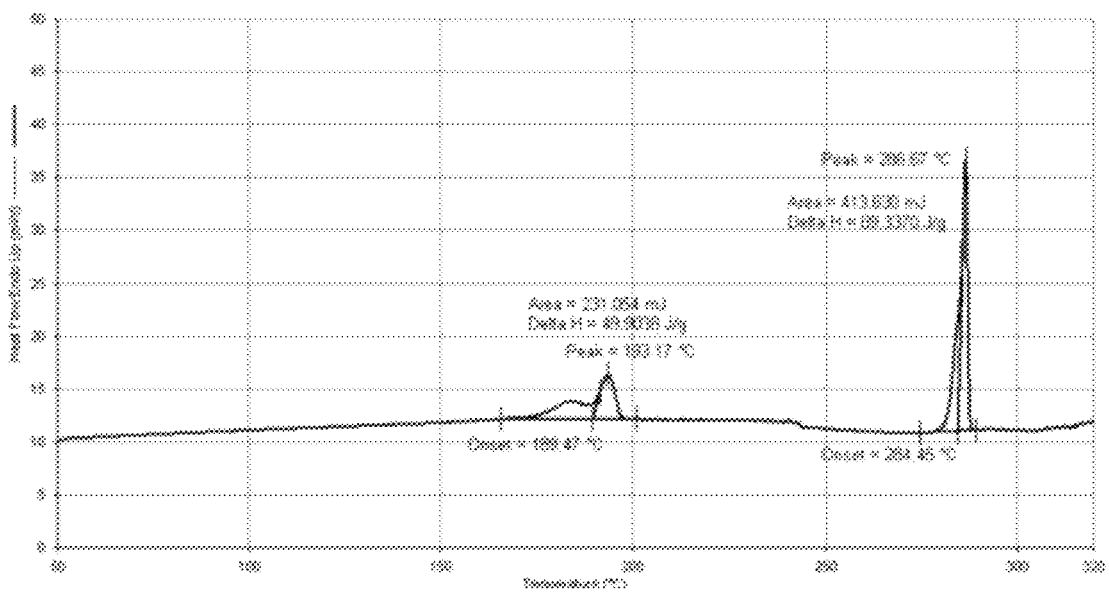
Polymorph II
Fig. 29

POLYMORPHS OF DASATINIB, PREPARATION METHODS AND PHARMACEUTICAL COMPOSITIONS THEREOF

FIELD OF THE INVENTION

The present invention is in the field of polymorphs of pharmaceutical compounds, and more specifically it relates to polymorphs of Dasatinib, and as well the preparing methods and pharmaceutical compositions thereof.

BACKGROUND OF THE INVENTION

Dasatinib, with the trade name SPRYCEL™, is a oral tyrosine kinase inhibitor and developed by BMS Company. It is used to cure adult chronic myelogenous leukemia (CML), acute lymphatic leukemia (ALL) with positive Philadelphia chromosome, etc. Its chemical name is N-(2-chloro-6-methylphenyl)-2-[[6-[4-(2-hydroxyethyl)-1-piperazinyl]-2-methyl-4-pyrimidyl]amino]-5-thiazolformamide and its chemical structure is as following:

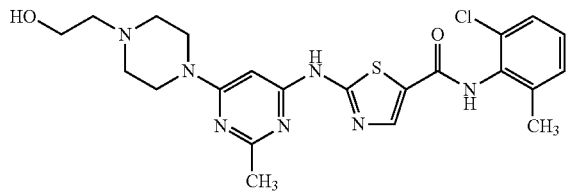 [SMILES: Cc1nc(Nc2ncc(C(=O)Nc3c(C)cccc3Cl)s2)cc(N2CCN(CCO)CC2)n1]

Five polymorphs of Dasatinib and the preparation methods thereof were described by Bristol-Myers Squibb in the Chinese Patent Application No. CN200580011916.6 (publication date is 13 Jun. 2007). The preparation methods instructed in this document are:

Monohydrate: Dasatinib (48 g) was added into ethanol (1056 mL 22 ml/g) and water (144 mL), and dissolved by heating to 75° C.; the mixture was purified, filtrated and transferred to the receiver. The solution reactor and transferring pipes were washed with the mixture of ethanol (43 mL) and water (5 mL). The solution was heated to 75~80° C. to be soluble completely and water (384 mL) was heated and the temperature of the solution was kept between 75° C. and 80° C. The seed crystal of monohydrate (preferable) was added when cooling to 75° C., and keep the temperature at 70° C. for 1 h; cooling to 5° C. within 2 h and keeping the temperature at 0~5° C. for 2 h. The slurry was filtrated and the filter cake was washed by the mixture of ethanol (96 mL) and water (96 mL); after being dried under vacuum≤50° C. 41 g of solid was obtained.

Butanol solvate: under refluxing (116° C.~118° C.), Dasatinib was dissolved in 1-butanol (about 1 g/25 mL) to yield crystalline butanol solvate of Dasatinib. When cooling, this butanol solvate was recrystallized from solution. The mixture was filtrated and the filter cake was dried after being washed with butanol.

Ethanol solvate: 5D (4 g, 10.1 mmol), 7B (6.6 g, 50.7 mmol), n-bubanol (80 mL) and DIPEA (2.61 g, 20.2 mmol)) were added into a 100 ml round flask. The obtained slurry was heated to 120° C. and kept the temperature for 4.5 h, and then cooled to 20° C. and stirred over night. The mixture was filtrate, and the wet filter cake was washed with n-butanol (2×10 mL) to yield white crystal product. The obtained wet filter cake was put back to the 100 ml reactor and 56 mL (12 mL/g) of 200 proof ethanol was added. Then additional ethanol (25 mL) was added at 80° C., and water (10 mL) was added into the mixture to make it dissolved rapidly. Heat was removed and crystallization was observed at 75° C.~77° C. The crystal slurry was further cooled to 20° C. and filtrated. The wet filter cake was washed with ethanol:water (1:1, 10 mL) once and then washed with n-heptane (10 mL) once. After that it was dried under the condition of 60° C./30 in Hg for 17 h to yield 3.55 g of substance only containing 0.19% water.

Neat form of N-6: DIPEA (155 mL, 0.89 mmol) was added into the mixture of compound 5D (175.45 g, 0.445 mol) and hydroxyethylpiperazine (289.67 g, 2.225 mol) in NMP (1168 mL). The suspension was heated at 110° C. for 25 min to be solution, which was then cooled down to about 90° C. The obtained solution was added dropwise into hot water (80° C., 8010 mL), and the mixture was stirred at 80° C. with heat preservation for 15 min and cooled to room temperature slowly. The solid was filtrated under vacuum and collected, washed by water (2×1600 mL) and dried under vacuum at 55° C.~60° C. to give 192.45 of compound.

Neat form of T1H1-7 (neat form and pharmaceutically acceptable carrier): monohydrate of Dasatinib was heated over dehydrate temperature to yield.

Because Dasatinib is practically insoluble in water or organic solvent (e.g. methanol, ethanol, propanol, isopropanol, butanol, pentanol, etc.), even in the condition of heating, a large amount (over 100 times) of solvent is needed, which is disadvantageous in industrial production; in addition, with the method described in the Patent document of CN200580011916.6, the related substances in products can not be lowed effectively during the process of crystal preparation to improve the products quality.

In terms of polymorphs of drug, each polymorph has different chemical and physical characteristics, including melting point, chemical stability, apparent solubility, rate of dissolution, optical and mechanical properties, vapor pressure as well as density. Such characteristics can directly influence the work-up or manufacture of bulk drug and formulation, and also affect the stability, solubility and bioavailability of formulation. Consequently, polymorph of drug is of great importance to quality, safety and efficacy of pharmaceutical preparation. When it comes to Dasatinib, there are still needs in the art for new polymorphs suitable for industrial production and with excellent physical and chemical properties as well.

SUMMARY OF THE INVENTION

The inventors of this invention have experienced a large amount of researches and unexpectedly found new polymorphs of Dasatinib to overcome the deficiencies of the prior art, and the new polymorphic forms have excellent physical and chemical properties and good stabilities, which are suitable for industrial production.

A purpose of this invention is to provide new polymorphs of Dasatinib.

Another purpose of this invention is to provide the preparation methods of these new polymorphs mentioned above.

The third purpose of this invention is to provide pharmaceutical compositions comprising the above-mentioned new polymorphs.

DETAILED DESCRIPTION OF THE INVENTION

More specifically, this invention provides a Polymorph I of Dasatinib with one molecule water and substantially without other solvents; as is shown in FIG. 1

The invention provides a Polymorph I of Dasatinib having the X-ray powder diffraction pattern by using Cu-Kα radiation, characterized by diffraction peaks at 9.1±0.2 and 19.4.0±0.2 of 2θ indicated with degree, further, one or multiple (in optional combination, including two or more peaks, or all peaks) of diffraction peaks at 9.1±0.2, 11.1±0.2, 13.7±0.2, 15.1±0.2, 17.8±0.2, 19.4±0.2 and 23.0±0.2; as is typically shown in FIG. 2

Diffraction peaks of the XRPD pattern for the Polymorph I of Dasatinib in the invention are listed as following

| Peak Number | 2θ | Flex Width | d-Value | Intensity | I/I0 |
|---|---|---|---|---|---|
| 1 | 4.520 | 0.188 | 19.5333 | 2322 | 14 |
| 2 | 9.060 | 0.235 | 9.7527 | 9061 | 54 |
| 3 | 11.100 | 0.212 | 7.9645 | 8989 | 53 |
| 4 | 13.260 | 0.141 | 6.6716 | 2361 | 14 |
| 5 | 13.640 | 0.259 | 6.4865 | 16278 | 96 |
| 6 | 14.580 | 0.188 | 6.0704 | 1155 | 7 |
| 7 | 15.100 | 0.235 | 5.8625 | 9371 | 56 |
| 8 | 16.100 | 0.235 | 5.5005 | 2594 | 16 |
| 9 | 17.440 | 0.165 | 5.0808 | 1298 | 8 |
| 10 | 17.820 | 0.235 | 4.9733 | 5443 | 32 |
| 11 | 18.280 | 0.259 | 4.8492 | 1295 | 8 |
| 12 | 19.380 | 0.259 | 4.5764 | 17013 | 100 |
| 13 | 20.040 | 0.212 | 4.4271 | 1157 | 7 |
| 14 | 21.560 | 0.212 | 4.1183 | 1641 | 10 |
| 15 | 22.000 | 0.353 | 4.0369 | 1720 | 11 |
| 16 | 22.940 | 0.400 | 3.8736 | 5828 | 35 |
| 17 | 23.540 | 0.235 | 3.7762 | 4597 | 28 |
| 18 | 24.280 | 0.235 | 3.6628 | 1489 | 9 |
| 19 | 25.680 | 0.329 | 3.4662 | 2926 | 18 |
| 20 | 26.200 | 0.165 | 3.3985 | 1128 | 7 |
| 21 | 27.860 | 0.282 | 3.1997 | 3236 | 20 |
| 22 | 28.360 | 0.400 | 3.1444 | 3833 | 23 |
| 23 | 30.040 | 0.188 | 2.9723 | 1169 | 7 |
| 24 | 32.260 | 0.282 | 2.7726 | 1455 | 9 |
| 25 | 32.980 | 0.424 | 2.7137 | 1485 | 9 |
| 26 | 33.980 | 0.353 | 2.6361 | 1136 | 7 |
| 27 | 34.420 | 0.471 | 2.6034 | 1461 | 9 |
| 28 | 35.000 | 0.329 | 2.5616 | 2299 | 14 |
| 29 | 39.460 | 0.212 | 2.2817 | 1118 | 7. |

The Polymorph I of Dasatinib provided by this invention is characterized in that its differential scanning calorimetry (DSC) has the first endothermic peak between about 100° C. and about 130° C., more specifically, at about 120° C., and the second endothermic peak, namely the maximal endothermic transformation, between 284° C. and 290° C., more specifically, at about 286.50° C. DSC diagram of the Polymorph I of Dasatinib of this invention is typically shown in FIG. 4-1, and Thermal Gravimetric Analysis (TGA) diagram is typically shown in FIG. 4-2.

In addition, the Polymorph I of Dasatinib in this invention has IR (Infrared Spectrum) in KBr disc, which is characterized by absorption peaks at about 3462.42 cm$^{-1}$, 3210.67 cm$^{-1}$, 3003.96 cm$^{-1}$, 2954.14 cm$^{-1}$, 2823.49 cm$^{-1}$, 1682.15 cm$^{-1}$, 1629.58 cm$^{-1}$, 1612.25 cm$^{-1}$, 1583.84 cm$^{-1}$, 1305.47 cm$^{-1}$, 1290.91 cm$^{-1}$, 1000.19 cm$^{-1}$, and 1040.60 cm$^{-1}$; as is typically shown in FIG. 3.

The Polymorph I of Dasatinib in this invention has characteristic chemical shifts δ(ppm) in $^{13}$C solid-state NMR spectrum: 16.75±0.2 ppm, 24.92±0.2 ppm, 41.72±0.2 ppm, 43.23±0.2 ppm, 44.28±0.2 ppm, 54.01±0.2 ppm, 55.48±0.2 ppm, 57.53±0.2 ppm, 58.70±0.2 ppm, 62.23±0.2 ppm, 63.20±0.2 ppm, 84.66±0.2 ppm, 127.92±0.2 ppm, 128.81±0.2 ppm, 132.70±0.2 ppm, 137.68±0.2 ppm, 139.00±0.2 ppm, 157.17±0.2 ppm, 162.07±0.2 ppm, 163.54±0.2 ppm, 166.84±0.2 ppm, and 167.58±0.2 ppm; as is typically shown in FIG. 5.

In one embodiment of the invention, this invention provides a preparing method of the Polymorph I of Dasatinib monohydrate, including the following steps:

(1). Dasatinib is added into dimethylformamide (DMF) or dimethylsulfoxide (DMSO), in which: the volume to weight ratio of DMF to Dasatinib is generally from 1:1 to 200:1 (ml:g); preferably, the volume to weight ratio is from 2:1 to 200:1; more preferably, the volume to weight ratio is from 3.5:1 to 4:1, whereas the volume to weight ratio of DMSO to Dasatinib is generally from 1:1 to 200:1; preferably, the volume to weight ratio is from 1.5:1 to 200; more preferably, the volume to weight ratio is from 2.5:1 to 3:1.

(2). It was stirred and heated to be dissolved; wherein, heating temperature can be between room temperature and the refluxing temperature of dimethylsulfoxide (DMSO) or dimethylformamide (DMF); preferable heating temperature may be between 40° C. and 100° C.; more preferably heating temperature may be between 50° C. and 80° C.

(3). A mixed solvent system of purified water and an organic solvent is added, wherein, the mentioned organic solvent is one kind of solvent or a mixed solvent of several kinds, to which Dasatinib is insoluble or slightly soluble. Preferably the temperature is at 40° C.~100° C. and more preferably at 50° C.~80° C.; wherein: the volume ratio of the mixed solvent system of purified water and an organic solvent to DMF or DMSO is generally from 1:1 to 200:1; preferably, the volume ratio is from 2:1 to 200:1; more preferably, the volume ratio is from 3:1 to 200:1; wherein, the mentioned organic solvent is one kind of solvent or a mixed solvent of several kinds, to which Dasatinib is insoluble or slightly soluble; preferably, is selected from the group consisting of acetonitrile, cyclohexane, 1,2-dichloroethene, 1,2-dimethoxyethane, dioxane, 2-ethoxyethanol, ethylene glycol, n-hexane, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, methanol, ethanol, propanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from the organic solvent in Class 3 or over regulated by ICH, such as: acetone, methoxybenzene, n-butanol, 2-butanol, butyl acetate, methyl tertiary-butyl ether, isopropylbenzene, ethanol, methanol, propanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether etc., and a mixture thereof, wherein the mixed solvent system is a dual or multiple mixture system consisting of water and organic solvent, and the weight ratio of water to organic solvent mentioned above is generally over 10%; preferably, this ratio was over 20%; more preferably this ratio was over 30%.

(4). After finish adding by droplet and heat preservation, with stirring cool it slowly to 0° C.~5° C. to precipitate solid completely and grow the grain; the time of heat preservation can be more than 10 min, preferably more than 1 h, more preferably more than 2 h; the time of growing grain can be more than 10 mins, preferably more than 1 h, more preferably more than 2 h.

(5). After filtration, the solid was collected and dried, preferably using phosphorus pentoxide as drying aid at 50° C. under −0.095 MPa over 12 h.

In another embodiment, this invention provides a Polymorph II of Dasatinib of an organic solvate without crystal water, which is shown in FIGS. 14-A and 14-B.

The Polymorph II of Dasatinib provided in the invention having the X-ray powder diffraction pattern by using Cu-Ka radiation, characterized by diffraction peaks at 5.7±0.2 and 14.5±0.2 of 2θ indicated with degree, further, one or multiple (in optional combination, including two or more peaks, or all peaks) of diffraction peaks at 5.7±0.2, 11.5±0.2, 12.3±0.2, 14.5±0.2, 17.2±0.2, 18.2±0.2, 22.2±0.2, 22.6±0.2, 24.7±0.2 and 25.2±0.2; as is shown in FIGS. 15-1 and 15-2. Wherein, the mentioned organic solvent is a mixture of dimethylsulfoxide (or dimethylformamide) and one or more solvents which Dasatinib is insoluble or slightly soluble in; the solvent Dasatinib insoluble or slightly soluble in, preferably, is selected from the group consisting of acetonitrile, trichloromethane, cyclohexane, 1,2-dichloroethene, dichloromethane, 1,2-dimethoxyethane, dioxane, 2-ethoxyethanol, ethylene glycol, n-hexane, methanol, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from one or more mixtures of acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether etc.; most preferably, the mentioned organic solvent is the mixture of dimethylsulfoxide and acetone or ethyl acetate, or the mixture of dimethylformamide and acetone or ethyl acetate.

Diffraction peaks of the XRPD pattern for Polymorph II of Dasatinib in the invention are listed as following

| Peak Number | 2θ | Flex Width | d-Value | Intensity | I/I0 |
|---|---|---|---|---|---|
| 1 | 5.720 | 0.212 | 15.4378 | 17437 | 74 |
| 2 | 11.480 | 0.212 | 7.7017 | 4950 | 21 |
| 3 | 12.260 | 0.235 | 7.2134 | 8089 | 35 |
| 4 | 14.520 | 0.212 | 6.0953 | 23640 | 100 |
| 5 | 14.860 | 0.165 | 5.9566 | 1571 | 7 |
| 6 | 15.940 | 0.282 | 5.5554 | 1821 | 8 |
| 7 | 17.240 | 0.259 | 5.1393 | 5961 | 26 |
| 8 | 18.200 | 0.235 | 4.8703 | 6730 | 29 |
| 9 | 18.980 | 0.235 | 4.6719 | 1476 | 7 |
| 10 | 20.440 | 0.235 | 4.3414 | 1527 | 7 |
| 11 | 21.180 | 0.212 | 4.1913 | 3249 | 14 |
| 12 | 22.160 | 0.235 | 4.0081 | 6002 | 26 |
| 13 | 22.560 | 0.212 | 3.9380 | 4970 | 22 |

-continued

| Peak Number | 2θ | Flex Width | d-Value | Intensity | I/I0 |
|---|---|---|---|---|---|
| 14 | 23.140 | 0.235 | 3.8406 | 2388 | 11 |
| 15 | 24.120 | 0.235 | 3.6867 | 1177 | 5 |
| 16 | 24.740 | 0.259 | 3.5957 | 7961 | 34 |
| 17 | 25.240 | 0.235 | 3.5256 | 13052 | 56 |
| 18 | 25.600 | 0.188 | 3.4768 | 3701 | 16 |
| 19 | 26.320 | 0.235 | 3.3833 | 3072 | 13 |
| 20 | 26.940 | 0.165 | 3.3068 | 1379 | 6 |
| 21 | 27.180 | 0.188 | 3.2782 | 1469 | 7 |
| 22 | 27.520 | 0.188 | 3.2384 | 1659 | 8 |
| 23 | 27.940 | 0.329 | 3.1907 | 1668 | 8 |
| 24 | 28.560 | 0.282 | 3.1228 | 1194 | 6 |
| 25 | 29.300 | 0.235 | 3.0456 | 1665 | 8 |
| 26 | 33.340 | 0.235 | 2.6852 | 1437 | 7 |
| 27 | 35.120 | 0.282 | 2.5531 | 1248 | 6 |
| 28 | 38.000 | 0.329 | 2.3660 | 1202 | 6 |

The Polymorph II of Dasatinib provided by this invention, typically the dimethylformamide/acetone solvate, is characterized in that its DSC has two endothermic peaks between 160° C. and 210° C., one of which is a greater endothermic peaks at about 193° C.; the third endothermic peak, namely the maximal endothermic transformation, between 280° C. and 290° C., more specifically, at about 286.67° C. DSC diagram of the Polymorph II of Dasatinib of this invention is typically shown in FIG. 17-1, and TGA diagram is typically shown in FIG. 17-2.

In addition, the Polymorph II of Dasatinib in this invention, typically the dimethylformamide/acetone solvate, has IR (Infrared Spectrum) in KBr disc, which is characterized by absorption peaks at about 3395.73 cm$^{-1}$, 3201.34 cm$^{-1}$, 3067.99 cm$^{-1}$, 2925.57 cm$^{-1}$, 2842.67 cm$^{-1}$, 2822.19 cm$^{-1}$, 1716.01 cm$^{-1}$, 1619.56 cm$^{-1}$, 1578.34 cm$^{-1}$, 1537.01 cm$^{-1}$, 1315.41 cm$^{-1}$, 1293.55 cm$^{-1}$, 1006.06 cm$^{-1}$, 984.74 cm$^{-1}$, and 1056.29 cm$^{-1}$; as is typically shown in FIG. 16.

The Polymorph II of Dasatinib provided by this invention, typically the dimethylformamide/acetone solvate, has characteristic chemical shifts δ (ppm) in $^{13}$C solid-state NMR spectrum: 18.80±0.2 ppm, 26.22±0.2 ppm, 27.60±0.2 ppm, 30.99±0.2 ppm, 36.57±0.2 ppm, 43.62±0.2 ppm, 51.57±0.2 ppm, 52.50±0.2 ppm, 55.09±0.2 ppm, 56.98±0.2 ppm, 62.51±0.2 ppm, 83.08±0.2 ppm, 125.43±0.2 ppm, 126.61±0.2 ppm, 128.44±0.2 ppm, 129.33±0.2 ppm, 132.65±0.2 ppm, 139.50±0.2 ppm, 156.34±0.2 ppm, 161.15±0.2 ppm, 162.96±0.2 ppm, 164.68±0.2 ppm, 165.47±0.2 ppm, and 203.49±0.2 ppm; as is typically shown in FIG. 18.

In one embodiment of the invention, this invention provides a preparing method of the Polymorph II of Dasatinib, including the following steps:

(1). Dasatinib is added into anhydrous dimethylformamide (DMF) or anhydrous dimethylsulfoxide (DMSO), in which: the volume to weight ratio of anhydrous DMF or andhydrous DMSO to Dasatinib is generally from 1:1 to 200:1 (ml:g); preferably, the volume to weight ratio is from 2:1 to 200:1; more preferably, the volume to weight ratio is from 3.5:1 to 4:1; and dissolved by stirring and heating;

(2). the solution mentioned above is added into an anhydrous organic solvent system which is several times in volume as much as that of the solution, wherein, the anhydrous organic solvent is selected from one or more of the solvent(s), to which Dasatinib is insoluble or slightly soluble. Wherein, the volume ratio of organic solvent to DMF or DMSO is generally 1~200:1; preferably, the volume ratio is 3~200:1; more preferably, the volume ratio is over 5~200:1. The mentioned organic solvent is herein one kind of solvent or a mixed solvent of several kinds, to which Dasatinib is insoluble or slightly soluble; preferably, is selected from the group consisting of acetonitrile, trichloromethane, cyclohexane, 1,2-dichloroethane, dichloroethene, dichloromethane, 1,2-dimethoxyethane, dioxane, 2-ethoxyethanol, ethylene glycol, n-hexane, methanol, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from one or more of acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether etc., and mixtures thereof;

(3). the organic solvent was evaporated slowly into the solution of Dasatinib in dimethylformamide or dimethyl sulfoxide between room temperature and the refluxing temperature of the organic solvent; wherein, the time of organic solvent evaporation can be from several hours at least to a few days; preferably is over 24 h; more preferably is over 72 h;

(4). after filtration, the solid was collected and dried, preferable using phosphorus pentoxide as drying aid at 50° C. under −0.095 MPa over 12 h.

In this invention, the scientific instruments and the test conditions involved in X-ray powder diffraction were: anode target-rotating X-ray diffractometer D/max-2500/PC-type (Japan Rigaku); Cu-target, graphite monochromator, tube voltage of 40 kV, tube current of 100 mA, both divergence slit and antidivergence slit of 1°, receiving slit of 0.3 mm, scanning speed of 5°/min and scanning range of from 3 to 40°.

The scientific instruments and the test conditions involved in DSC in this invention were: US Perkin Elmer Diamond DSC; heating from 25° C. to 300° C. at the rate of 10° C./min.

The scientific instruments and the test conditions involved in TGA in this invention were: US Perkin Elmer Thermal Analysis Pyris 1 TGA; heating from 25° C. to 300° C. at the rate of 10° C./min.

The scientific instruments and the test conditions involved in solid-state NMR in this invention were:

instruments: wide-bore solid-state NMR spectrometer AVANCE III 400 MH-type (BRUKER);

test conditions: CP-MAS; methods: rotating speed of 14000 Hz, scanning times of 1404, relaxation delay of 40 s, contact time of 2 ms, 13C frequency of 100.6234936 MHz and 1H frequency of 400.1413530 MHz.

The conditions and methods of related substance test involved in this invention was in accordance with HPLC (Appendix VD of Chinese Pharmacopoeia, Vol. II, (2005)).

Chromatographic conditions and system applicability:
octadecylsilane bonded silica as the filler; 0.05 mol/L of potassium dihydrogen phosphate (adjusted to pH 2.5 by phosphoric acid)-methanol (45:55) as the mobile phase; detection wavelength was 230 nm; the number of theoretical plates should be not less than 2000, calculated according to the peak area of Dasatinib. The resolution of the peak of Dasatinib from the peaks of adjacent impurities should meet requirements.

Test Method: the sample was weight and dissolved into mobile phase to be the solution containing 0.5 mg per mL, and 20 μL of this solution was taken and injected into liquid chromatography. Chromatogram was recorded until it is 6 times as the retention time of the main peak.

The Characteristics of the Polymorph I of Dasatinib Monohydrate

1. Solubility: test was performed according to the Examples of Chinese Pharmacopoeia, Vol. II, (2000).

Method: a definite quantity of the Polymorph I of Dasatinib measured accurately was added into a certain quantity of solvent slowly, while the mixture was shaken strongly for 30 seconds every 5 minutes and the dissolving status within 30 minutes was observed. Results were listed in Tab. 1.

TABLE 1 solubility test of the Polymorph I of Dasatinib monohydrate

| Solvent | Sample quantity (g) | Solvent quantity (ml) | Solute:Solvent | Dissolving status | Conclusion |
|---|---|---|---|---|---|
| water | 0.0101 | 105 | 1:10396 | cannot fully dissolved | practically insoluble |
| 0.1 mol/L NaOH solution | 0.0109 | 120 | 1:11009 | cannot fully dissolved | practically insoluble |
| 0.1 mol/L HCl solution | 0.0100 | 80 | 1:8000 | fully dissolved | very slightly |
| acetonitrile | 0.0106 | 100 | 1:9434 | fully dissolved | very slightly |
| methanol | 0.0106 | 120 | 1:11321 | cannot fully dissolved | practically insoluble |

2. Stability 2.1 Photostability Test

The Polymorph I of Dasatinib monohydrate was distributed homogeneously in open petri dish with the thickness of the raw material not more than 5 mm, and the distance was adjusted to make illumination intensity at 4500±500 Lx. Sample was tested at the $5^{th}$ and $10^{th}$ day respectively and the results were contrasted with that of the Day 0. Results were listed in Tab. 2. After strong illumination for 10 days, the X-ray powder diffraction pattern was shown in FIG. 6; DSC diagram of the Polymorph I of Dasatinib monohydrate was shown in FIG. 7.

TABLE 2

Photostability Test (4500 ± 500lx)

| Time (days) | Appearance | Related substance | Content | Melting point (Decomposition point) |
|---|---|---|---|---|
| 0 | white powder | 0.07% | 99.7% | 286.50° C. |
| 5 | white powder | 0.21% | 99.6% | / |
| 10 | white powder | 0.34% | 99.4% | 284.83° C. |

Note:
the fluctuation of temperature was between 23° C. and 26° C.; relative humidity was between 56% and 63%.

2.2 High Temperature Test

The raw material of Polymorph I of Dasatinib monohydrate was put into a clean sealed glass bottle and then put in thermostatic drying chamber at 60° C. Sample was tested at the 5th and 10th day respectively and the results were contrasted with that of the Day 0. Results were listed in Tab. 3. After high temperature test of 60° C. for 10 days, the X-ray powder diffraction pattern was shown in FIG. 8; DSC diagram was in FIG. 9-1, and TGA diagram was in FIG. 9-2.

TABLE 3

High Temperature Test (60° C.)

| Time (days) | Appearance | Related substance | Content | Melting point |
|---|---|---|---|---|
| 0 | white powder | 0.06% | 99.8% | 286.50° C. |
| 5 | white powder | 0.09% | 99.7% | / |
| 10 | white powder | 0.12% | 99.5% | 284.83° C. |

Note:
the variation of relative humidity was between 54% and 62%.

2.3 High Humidity Test

The raw material of Polymorph I of Dasatinib monohydrate was distributed homogeneously in open petri dish with thickness of the raw material not more than 5 mm and put into thermostatic and humidostatic incubator at room temperature (about 25° C.) and 75±5% relative humidity. Sample was tested at the 5th and 10th day respectively and the results were contrasted with that of the Day 0. Results were listed in Tab. 4. After high humidity test of 75±5% relative humidity for 10 days, the X-ray powder diffraction pattern was shown in FIG. 10; DSC diagram was in FIG. 11-1; TGA diagram was in FIG. 11-2.

TABLE 4

High Humidity Test (room temperature and 75 ± 5% relative humidity)

| Time (days) | Appearance | Weight gain of moisture absorption (%) | Content (%) | Melting point (° C.) |
|---|---|---|---|---|
| 0 | white powder | 3.57% | 99.7% | 286.50° C. |
| 5 | white powder | 3.73% | 99.6% | / |
| 10 | white powder | 3.76% | 99.7% | 284.67° C. |

Note:
the fluctuation of temperature was between 23° C. and 26° C.

2.4 Accelerated Test

The raw material of Polymorph I of Dasatinib was hermetically packed in plastic bags of polyethylene film and put in thermostatic and humidostatic incubator at 40±2° C. and 75±5% relative humidity for six months. Sample was tested at the end of the 1st, 2nd, 3rd and 6th month respectively and the results were contrasted with that of the zeroth month. Results were listed in Tab. 5. After six months, the X-ray powder diffraction pattern was shown in FIG. 12; DSC diagram was in FIG. 13-1; TGA diagram was in FIG. 13-2.

TABLE 5

Accelerated Test (40° C. and 75% relative humidity)

| Time (months) | Appearance | Related substances (%) | Content (%) | Melting point (° C.) |
|---|---|---|---|---|
| 0 | white powder | 0.07% | 99.7% | 286.50° C. |
| 1 | white powder | 0.07% | 99.6% | / |
| 2 | white powder | 0.08% | 99.6% | / |
| 3 | white powder | 0.08% | 99.6% | / |
| 6 | white powder | 0.09% | 99.5% | 284.83° C. |

As is known from above results that in photostability test related substances of Polymorph I of Dasatinib monohydrate obtained by this invention increased slightly, while the content of product was of some drop; in high temperature (60° C.) test, the appearance had few obvious change while the content of this product went down marginally; in high humidity test, both appearance and content of this product had no obvious change, and hydroscopic property was lower; the results of accelerated test demonstrates that the physical and chemical characteristic are relatively stable.

In the observation test of long-term sample storage, crystal transformation was not found, while related substances increased slightly and content of product decreased slightly, which means that the crystal morphology of polymorph I is relatively stable and suitable for long-term storage.

In addition, weight (water)-loss process of the polymorph I happened during a period from 70° C. to 150° C., weight loss was 3.60% calculated on the base of TGA scan diagram of the Polymorph I of Dasatinib monohydrate (FIG. 4-2); also after test it reveals that the amount of organic solvent residue in the product compound was in accordance with the limit requests regulated by ICH; moisture content was 3.59% determined with KF method; in sum, the analyses of test results mentioned above demonstrate that the Polymorph I of Dasatinib of this invention is monohydrate.

Through further tests it is found that the Polymorph I of this invention would lose crystal water (partly to all) step by step when it was put in a sealed surrounding with strong dehydrating agent (such as allochroic silicagel and phosphorus pentoxide etc.), but the polymorph losing part crystal moisture would return to the Polymorph I with one crystal water step by step when it was put in air environment.

The Characteristics of the Polymorph II of Dasatinib

1. Solubility: test was performed according to the Examples of Chinese Pharmacopoeia, Vol. II, (2000).

Method: a definite quantity of the Polymorph II of Dasatinib measured accurately was added into a certain quantity of solvent slowly, while the mixture was shaken strongly for 30 seconds every 5 minutes and the dissolving status within 30 minutes was observed. Results were listed in Tab. 6.

TABLE 6 solubility test of the Polymorph II of Dasatinib

| Solvent | Sample quantity (g) | Solvent quantity (ml) | Solute: Solvent | Dissolving status | Conclusion |
|---|---|---|---|---|---|
| water | 0.0099 | 100 | 1:10101 | cannot fully dissolved | practically insoluble |
| 0.1 mol/L NaOH solution | 0.0100 | 100 | 1:10000 | cannot fully dissolved | practically insoluble |
| 0.1 mol/L HCl solution | 0.0097 | 80 | 1:8247 | fully dissolved | very slightly soluble |

TABLE 6-continued solubility test of the Polymorph II of Dasatinib

| Solvent | Sample quantity (g) | Solvent quantity (ml) | Solute: Solvent | Dissolving status | Conclusion |
|---|---|---|---|---|---|
| acetonitrile | 0.0110 | 120 | 1:10910 | cannot fully dissolved | practically insoluble |
| methanol | 0.0106 | 100 | 1:9434 | fully dissolved | very slightly soluble |

2. Stability
2.1 Photostability Test

The Polymorph II of Dasatinib was distributed homogeneously in open petri dish with the thickness of the raw material not more than 5 mm, and the distance was adjusted to make illumination intensity at 4500±500 Lx. Sample was tested at the $5^{th}$ and $10^{th}$ day respectively and the results were contrasted with that of the Day 0. Results were listed in Tab. 7. After strong illumination for 10 days, the X-ray powder diffraction pattern was shown in FIG. 19; DSC diagram of the Polymorph II of Dasatinib was shown in FIG. 20.

TABLE 7

Photostability Test (4500 ± 500lx)

| | | Items | | |
|---|---|---|---|---|
| Time (days) | Appearance | Related substance (%) | Content (%) | Melting point (Decomposition point) |
| 0 | white powder | 0.06% | 99.8% | 286.67° C. |
| 5 | white powder | 0.22% | 99.6% | / |
| 10 | white powder | 0.36% | 99.3% | 287.17° C. |

Note:
the fluctuation of temperature was between 23° C. and 26° C.; relative humidity was between 56% and 63%.

2.2 High Temperature Test

The raw material of Polymorph II of Dasatinib was put into a clean sealed glass bottle and then put in thermostatic drying chamber at 60° C. Sample was tested at the $5^{th}$ and $10^{th}$ day respectively and the results were contrasted with that of the Day 0. Results were listed in Tab. 8. After high temperature test of 60° C. for 10 days, the X-ray powder diffraction pattern was shown in FIG. 21; DSC diagram was in FIG. 22.

TABLE 8

High Temperature Test (60° C.)

| | | Items | | |
|---|---|---|---|---|
| Time (days) | Appearance | Related substance (%) | Content (%) | Melting point (Decomposition point) |
| 0 | white powder | 0.06% | 99.8% | 286.67° C. |
| 5 | white powder | 0.11% | 99.7% | / |
| 10 | white powder | 0.16% | 99.4% | 286.83° C. |

Note:
the variation of relative humidity was between 54% and 62%.

2.3 High Humidity Test

The raw material of Polymorph II of Dasatinib was distributed homogeneously in open petri dish with thickness of the raw material not more than 5 mm and put into thermostatic and humidostatic incubator at room temperature (about 25° C.) and 75±5% relative humidity. Sample was tested at the $5^{th}$ and $10^{th}$ day respectively and the results were contrasted with that of the Day 0. Results were listed in Tab. 9. After high humidity test of 75±5% relative humidity for 10 days, the X-ray powder diffraction pattern was shown in FIG. 23; DSC diagram was in FIG. 24-1; TGA diagram was in FIG. 24-2.

TABLE 9

High Humidity Test (room temperature and 75 ± 5% relative humidity)

| | | Items | | |
|---|---|---|---|---|
| Time (days) | Appearance | Weight gain of moisture absorption (%) | Content (%) | Melting point (Decomposition point, ° C.) |
| 0 | white powder | 0.57% | 99.8% | 286.67° C. |
| 5 | white powder | 3.63% | 99.7% | / |
| 10 | white powder | 3.72% | 99.8% | 288.50° C. |

Note:
the fluctuation of temperature was between 23° C. and 26° C.

2.4 Accelerated Test

The raw material of Polymorph II of Dasatinib was hermetically packed in plastic bags of polyethylene film and put in thermostatic and humidostatic incubator at 40±2° C. and 75±5% relative humidity for six months. Sample was tested at the end of the $1^{st}$, $2^{nd}$, $3^{rd}$ and $6^{th}$ month respectively and the results were contrasted with that of the zeroth month. Results were listed in Tab. 10. After accelerated test at 40° C. for six months, the X-ray powder diffraction pattern was shown in FIG. 25; DSC diagram was in FIG. 26-1; TGA diagram was in FIG. 26-2.

TABLE 10

Accelerated Test (40° C. and 75% relative humidity)

| | | Items | | |
|---|---|---|---|---|
| Time (months) | Appearance | Related substance (%) | Content (%) | Melting point (Decomposition point, ° C.) |
| 0 | white powder | 0.06% | 99.8% | 286.67° C. |
| 1 | white powder | 0.07% | 99.7% | / |
| 2 | white powder | 0.08% | 99.8% | / |
| 3 | white powder | 0.07% | 99.6% | / |
| 6 | white powder | 0.08% | 99.6% | 287.17° C. |

As is known from above results that in photostability test, the appearance of Polymorph II of Dasatinib obtained by this invention had no obvious change and related substances increased slightly, while the content of product was of some drop; in high temperature (60° C.) test, both appearance and content of this product had few obvious change, which demonstrated the characteristic of relative stability; in high humidity test, both appearance and content of this product had no obvious change, and hydroscopic property was lower; the results of accelerated test reveals that the physical and chemical characteristic are of relative stability.

In another embodiment of this invention, it provides pharmaceutical compositions comprising one or more of the Polymorph I and II of Dasatinib and a pharmaceutical excipient; preferably, the pharmaceutical composition contains 1 mg~500 mg of the polymorph of Dasatinib; more preferably, it contains 20 mg, 50 mg, 70 mg or 100 mg of the polymorph of Dasatinib. The pharmaceutical compositions of this invention could be prepared into all kinds of formulations and the proper pharmaceutical excipient could be selected. For instance, according to the diseases and subjects, the pharmaceutical compositions of this invention could be delivered through such administration routes: oral, parenteral (e.g. intramuscular, intraperitoneal, intravenous, intracerebroventricular, intracisternal and subcutaneous injection or infusion), inhalation spray, nasal, vaginal, rectal, sublingual or local delivery; preferably, it is oral formulations, such as tablets, capsules or granules. A person having ordinary skill in the art can coat the oral pharmaceutical compositions according to the teaching in the prior art, for instant, the Chinese Patent CN 101170996A (publication date is 30 Apr. 2008)

Depending on the needs the pharmaceutical composition containing the polymorph of Dasatinib of this invent can contain other therapeutic ingredients, for example, one or more kinds of Ipsapirone, Taxol, Docetaxel, Cisplatin, Carboplatin, Bevacizumab, Bendamustine, Erlotinib, Nilotinib, Rituxima, Dexamethason, Lenalidomide, Capecitabine, Exemestane, Letrozole, Dacarbazine, Vandetanib, Ipilimumab, etc.

The pharmaceutical composition of this invention was administrated once or multiple times every day on the basis of daily dose, and the daily dose was about from 5 mg to 1000 mg per day, more preferably from 10 mg to 500 mg per day. Alternatively, the pharmaceutical composition was administrated every other day, from about 10 mg to about 250 mg per day.

The diseases and conditions which can be treated by Dasatinib of the invention include, but not limited to: transplant rejection, rheumatoid arthritis, Multiple Sclerosis, enteritis, lupus, graft versus host disease, T-cell mediated hypersensitive disease, psoriasis, Hashimoto's struma, cancer (including chronic myelogenous leukemia, gastrointestinal stromal tumor, small cell lung cancer, non-small cell lung cancer, oophoroma, melanoma, mastocytosis, gonioma, acute myelogenous leukemia, sarcoma in children, breast cancer, colorectal cancer, pancreatic carcinoma, prostatic carcinoma, etc.), contact dermatitis, anaphylactic disease, asthma, diabetic retinopathy, and chronic obstructive pulmonary disease, etc. In addition, by the instruction of this invention, a person skilled in the art can confirm the specific methods and dosages according to the teaching in the prior art, for instant, the International application for patent with publication number WO2004085388A2.

The technical advantages of this invention include: although polymorphs of Dasatinib and the preparation methods thereof have been reported in the patent documentation of CN200580011916.6, the methods provided by the Patent CN200580011916.6 to prepare the polymorphs of Dasatinib was verified by tests that the crystal transformation method described in the patent was unsuitable for industrial production.

By the existing technique in patent document CN200580011916.6, the preparation method was that: Dasatinib was added into alcohol organic solvent or the mixture of alcohol organic solvent and water (alcohol solvents such as methanol, ethanol and butanol etc.) which Dasatinib is practically insoluble in, after dissolved by heating, crystal was precipitated when being cooled.

1. Because Dasatinib was practically insoluble in water or the alcohol solvents mentioned above, and a large quantity of solvent should be used even in the condition of heating. So the processes of crystal transformation are complicated, and products quality is controlled poorly, which is unsuitable for industrial production steadily.

2. By the method of crystal transformation described in the patent of CN CN200580011916.6, the related substances of the original products did not decrease dramatically to improve product quality.

3. It is revealed through tests that by comparison with Polymorph I of this invention, Polymorph A prepared according to the conditions described in the patents of CN CN200580011916.6 had worse performance in stability.

In a word, the methods of Dasatinib polymorph preparation in patent CN200580011916.6 were unsuitable to industrial production steadily.

However, this invention provided two polymorphs of Dasatinib suitable to industrial manufacture, and overcame the problems in existing technique.

In terms of the two new polymorphs of Dasatinib in this invention, the crystallization conditions were contemplated in views of the insolubility of Dasatinib in most solvents and difficult purification, so easy and feasible preparation methods were adopted:

1. the preparation process of this invention was simple, quite easy for operation and convenient for industrial production, and the quality of the products was controllable with paralleled yields;

2. by the methods of crystal transformation, strong-polar impurities were removed easily, resulting in dramatically reduction in related substance;

3. by comparison to the polymorphs prepared by the processes in this invention with those produced by the original methods, it is evident that the appearance, color and luster of the products could be improved;

4. the polymorphs prepared by the processes in this invention had good stability suitable to long-term storage;

5. by comparison to the polymorph A described in patent CN200580011916.6, the Polymorph I and Polymorph II of this invention had better stability in water, so the polymorphs of this invention had more advantages for formulation and long-term storage; in addition, the experiments have shown that after being formulated, the crystalline forms of Polymorph I and Polymorph II of this invention had no substantially change, and stability of the crystalline form was excellent, furthermore, the relative substances of bulk drug in the formulation didn't increase when detecting, so they were more suitable for pharmaceuticals.

6. by the methods of polymorph preparation in this invention, the amount of organic solvent used in crystal transformation could be reduced greatly, which led to reduced cost of products;

7. by the methods of this invention, water or organic solvents in Class III with low toxicity could be used selectively to prepare the polymorphs of this invention, reducing the toxic effects of the residual organic solvents potentially on human body to some extent.

Due to the above-mentioned advantages, this invention was beneficial to dramatic improvement in products quality and suitable to industrial production.

BRIEF DESCRIPTION OF DRAWINGS

FIG. 2 is a typical XRPD pattern of the Polymorph I of Dasatinib of this invention.

FIG. 4-1 and FIG. 4-2 are respectively DSC diagram and TGA diagram of the Polymorph I of Dasatinib of this invention.

FIG. 9-1 and FIG. 9-2 are respectively DSC diagram and TGA diagram of the Polymorph I of Dasatinib of this invention after high temperature test of 60° C. for 10 days.

FIG. 11-1 and FIG. 11-2 are respectively DSC diagram and TGA diagram of the Polymorph I of Dasatinib of this invention after high humidity for 10 days.

FIG. 13-1 and FIG. 13-2 are respectively DSC diagram and TGA diagram of the Polymorph I of Dasatinib of this invention after accelerated test at 40° C. for six months.

FIG. 14-A and FIG. 14-B are microscopic photos of Polymorph II of Dasatinib of this invention.

FIG. 15-1 is a typical XRPD pattern of the Polymorph II of Dasatinib (dimethylformamide/acetone) of this invention.

FIG. 15-2 is a typical XRPD pattern of the Polymorph II of Dasatinib (dimethyl sulfoxide/ethyl acetate) of this invention.

FIG. 17-1 and FIG. 17-2 are respectively DSC diagram and TGA diagram of the Polymorph II of Dasatinib of this invention.

FIG. 24-1 and FIG. 24-2 are respectively DSC diagram and TGA diagram of the Polymorph II of Dasatinib of this invention after high humidity for 10 days.

FIG. 26-1 and FIG. 26-2 are respectively DSC diagram and TGA diagram of the Polymorph II of Dasatinib of this invention after accelerated test at 40° C. for six months.

FIG. 27 is a comparative XRPD pattern of the Polymorph I and II of Dasatinib of this invention.

FIG. 29 is a comparative DSC diagram of the Polymorph I and II of Dasatinib of this invention

DESCRIPTION OF EMBODIMENTS

Example 1

Preparation of the Polymorph I

A. Dasatinib (10 g) and DMSO (40 ml) were added into a flask and heated up to 60~70° C. by stirring, after dissolving, the mixture (120 mL) of water and acetone (1:1) was added under heat preservation. When crystal was precipitated, cooled it down to 0° C. to grow the grains for 10 minutes. Filtrate it and the cake was washed by water and then by the mixture of water and acetone (1:1). After that it was dried under −0.095 MPa at about 50° C. using phosphorus pentoxide as drying aid to give 7.7 g of white solid. Yield was 77%.

| | Contrasts | |
|---|---|---|
| Items | Index of raw material before transformation | Index of Polymorph I |
| Appearance | off-white powder | White crystal powder |
| Related substance | 0.85% | 0.07% |
| KF moisture | 0.67% | 3.59% |
| 70~150 TGA weight loss | 0.72% | 3.63% |

Figure 1:
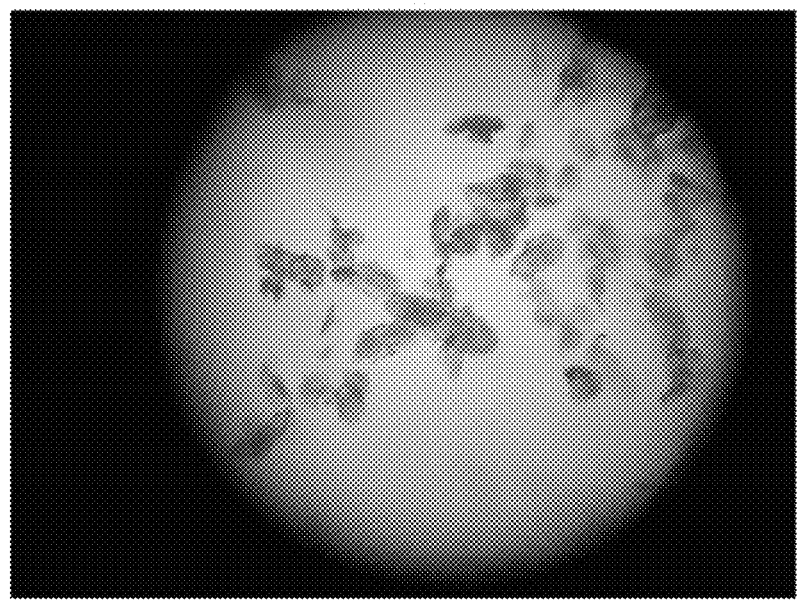
FIG. 1 is a microscopic photo of Polymorph I of Dasatinib of this invention.
Figure 3:
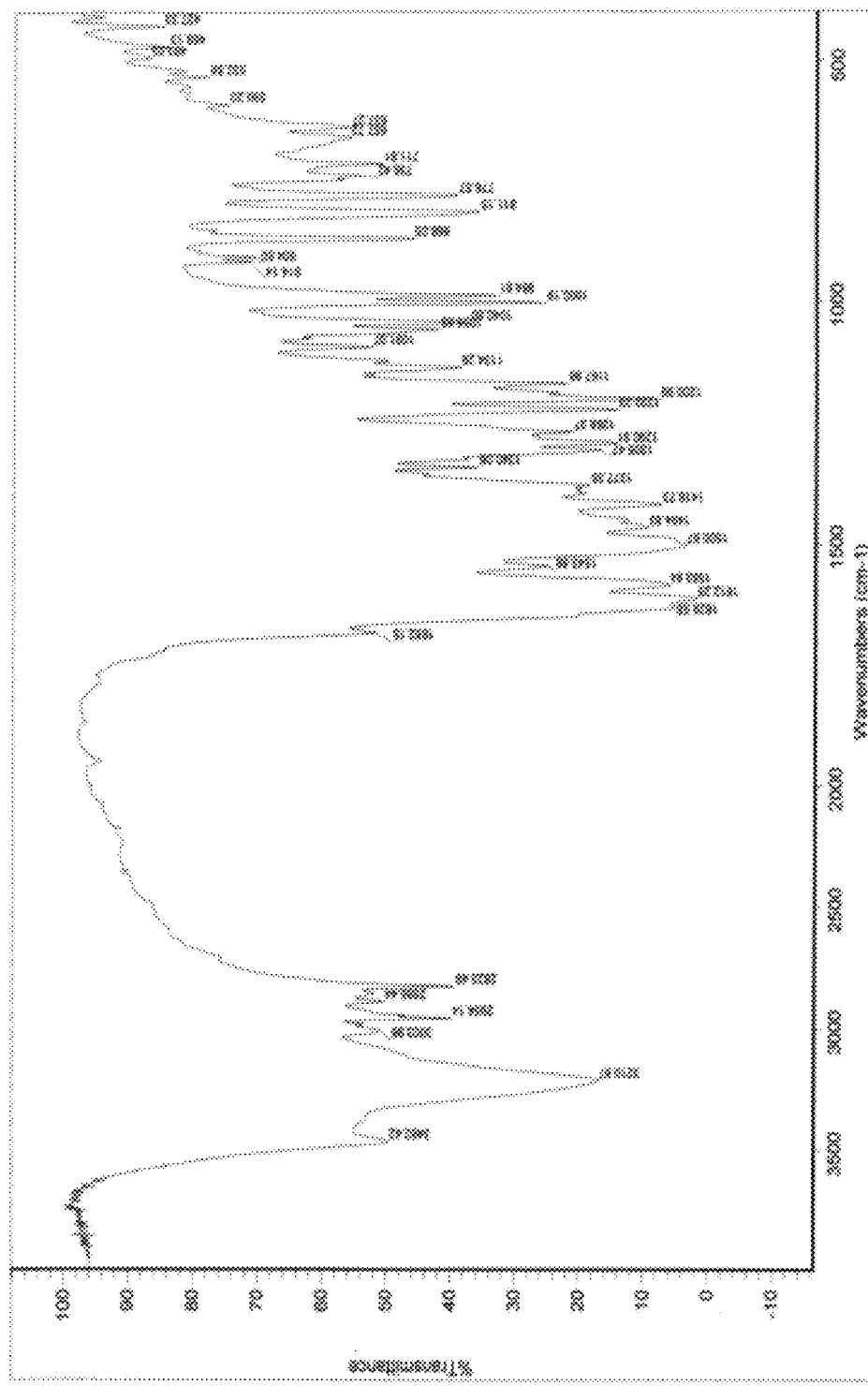
FIG. 3 is an IR diagram of the Polymorph I of Dasatinib of this invention.
Figures 1, 4:
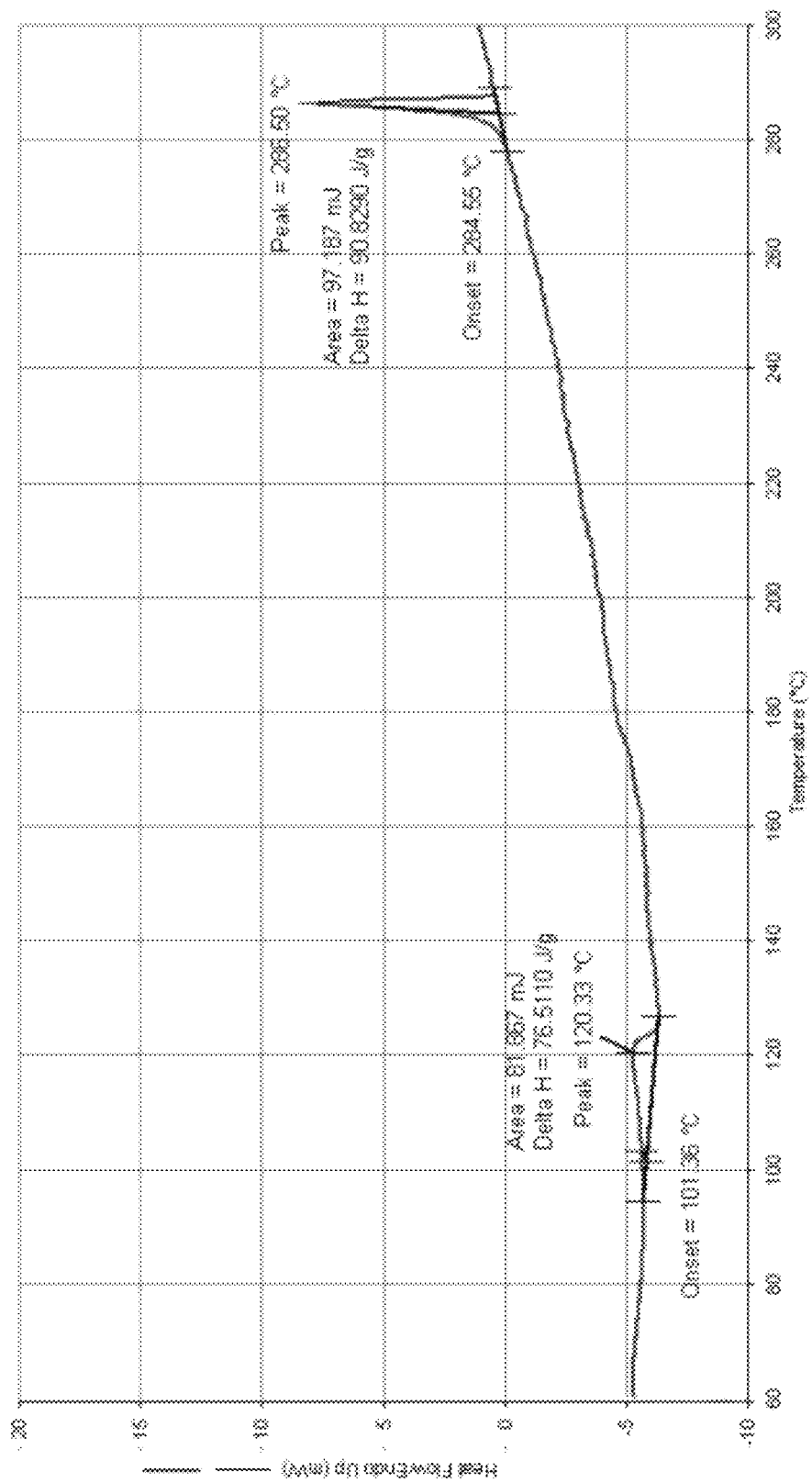
Figures 2, 4:
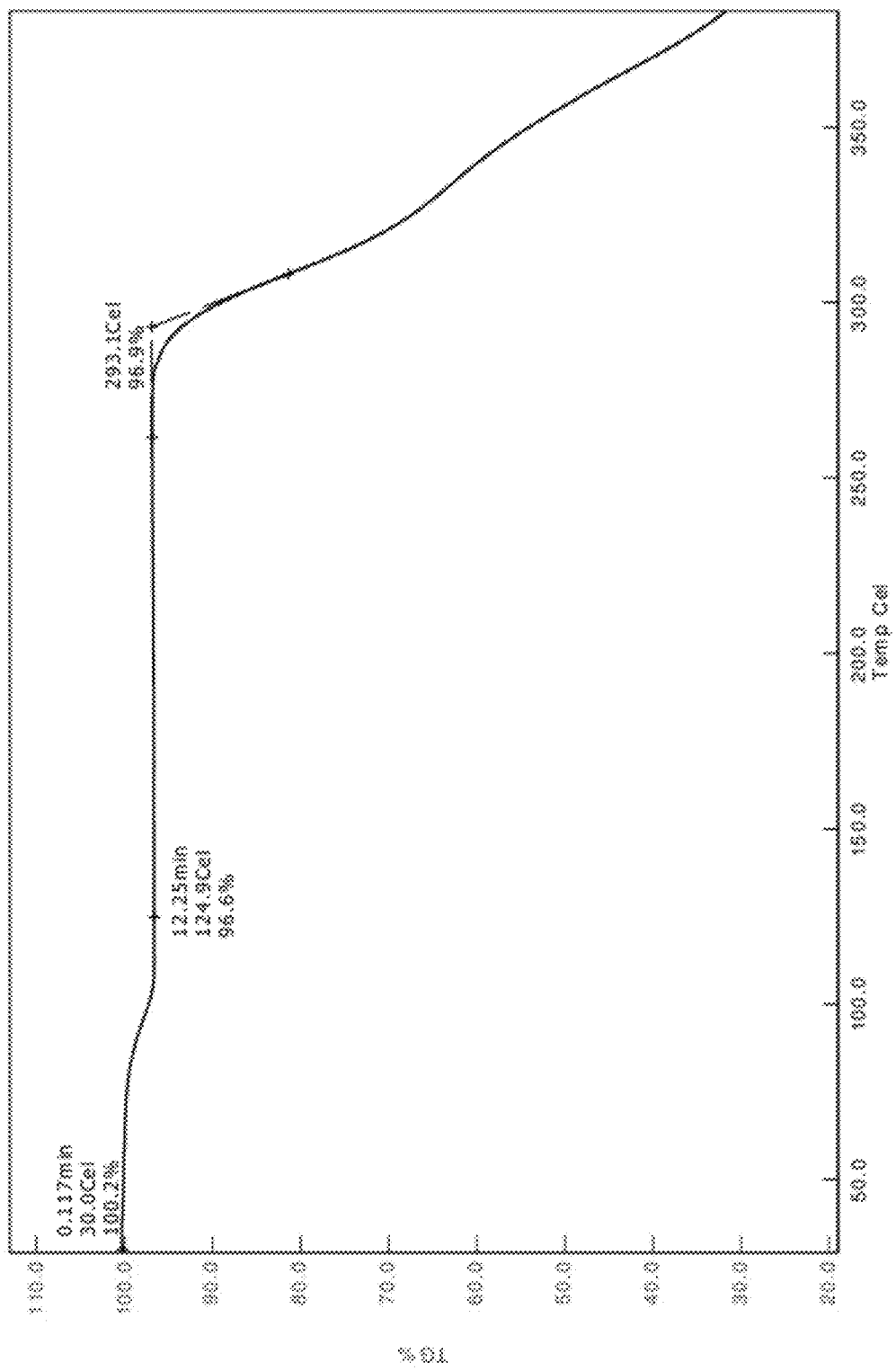
Figure 5:
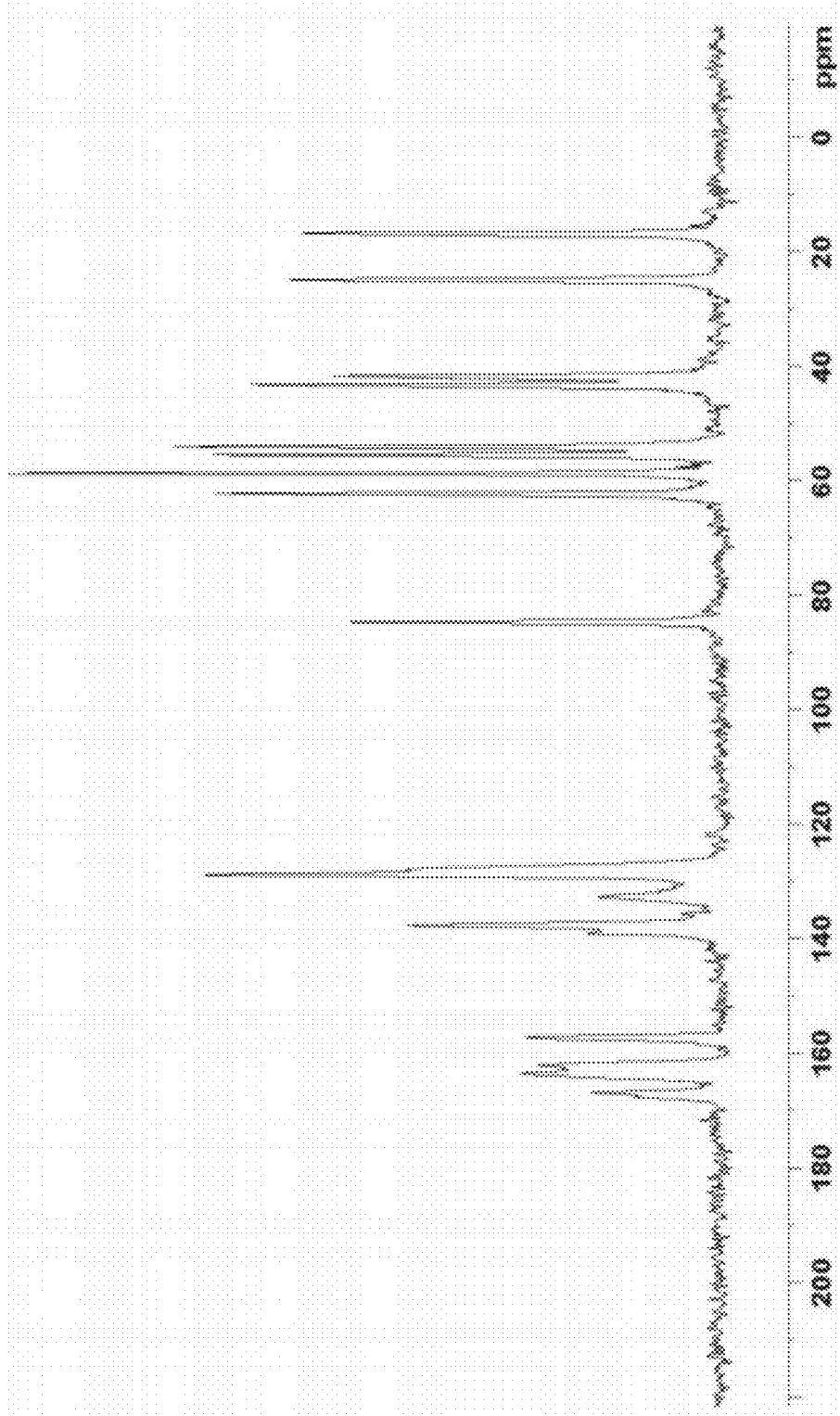
FIG. 5 is a 13C solid-state NMR spectrum of the Polymorph I of Dasatinib of this invention.
Figure 6:
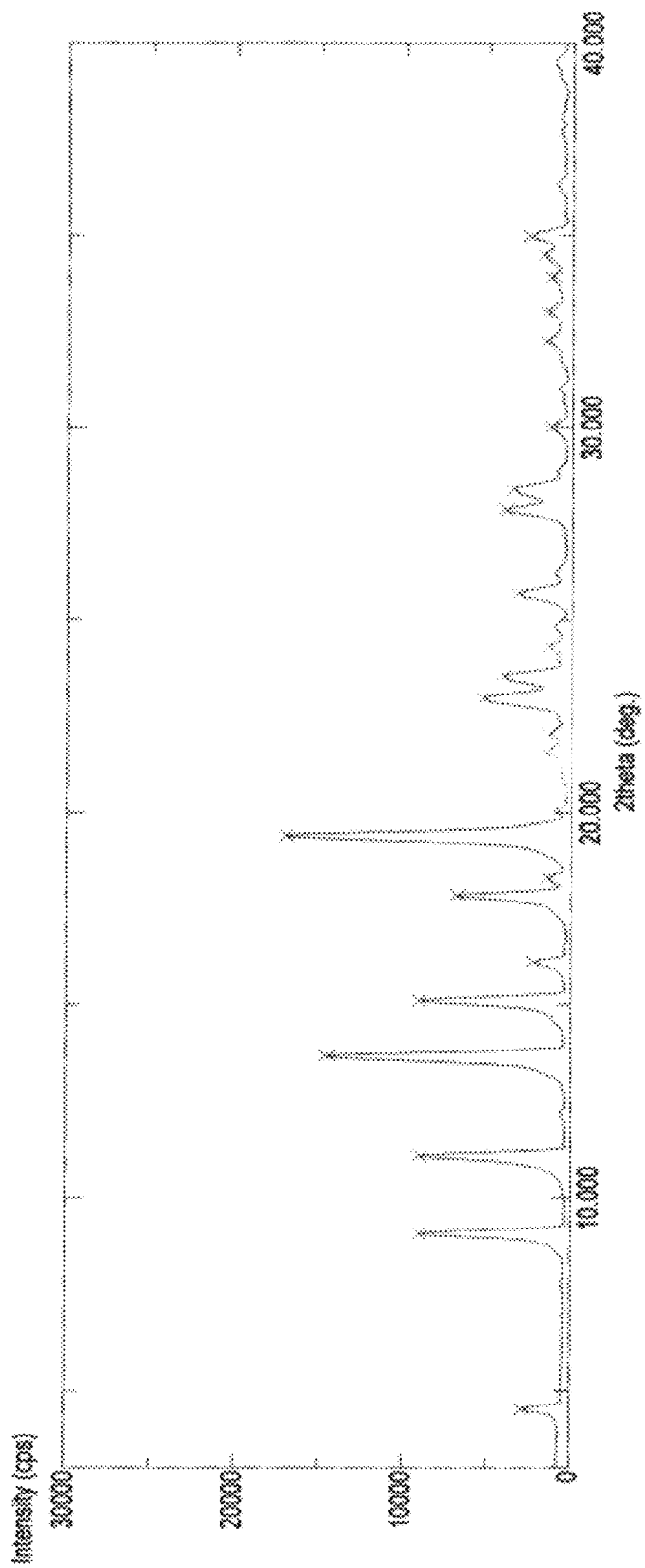
FIG. 6 is an XRPD pattern of the Polymorph I of Dasatinib of this invention after strong illumination for 10 days.
Figure 7:
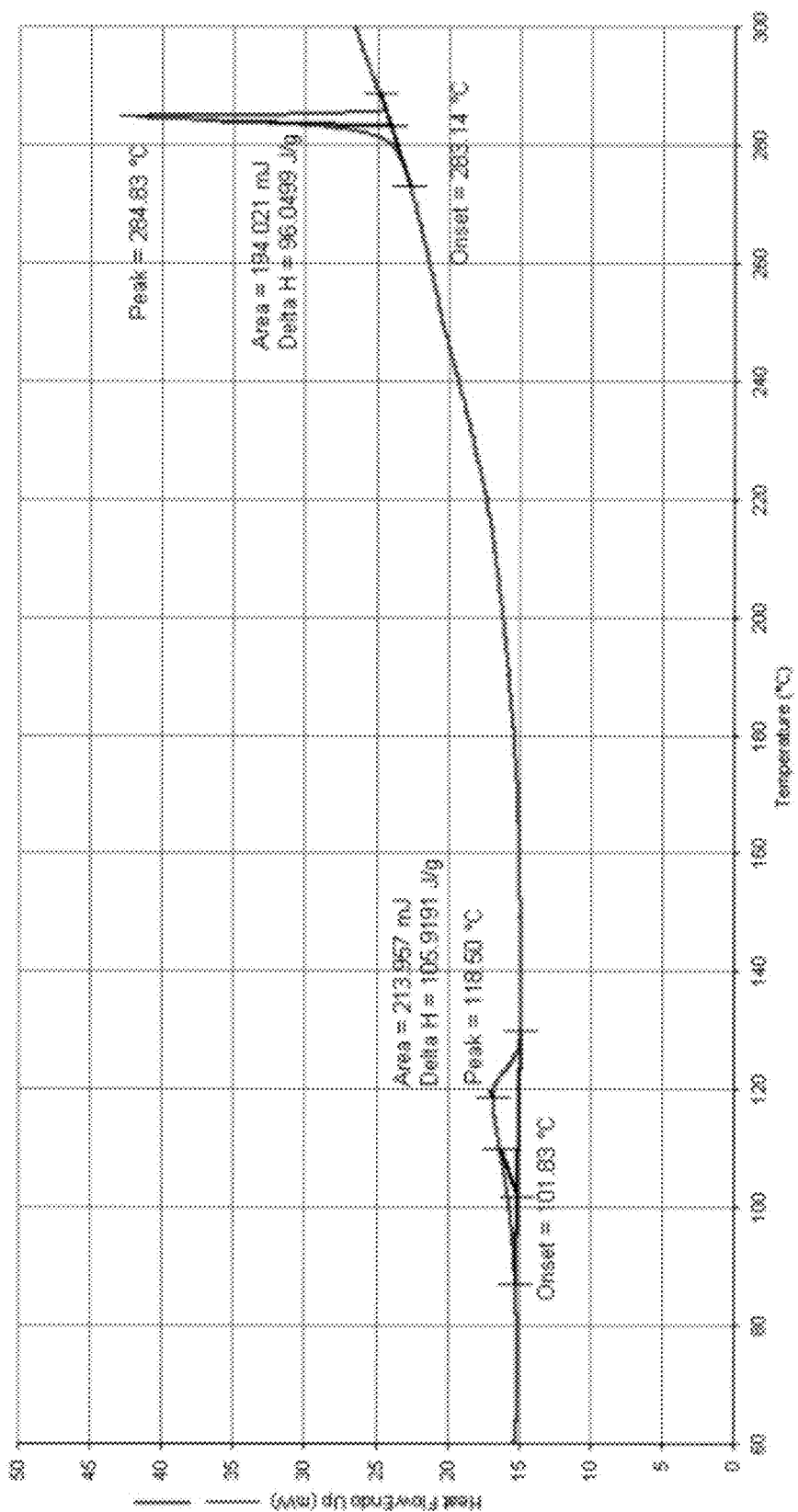
FIG. 7 is a DSC diagram of the Polymorph I of Dasatinib of this invention after strong illumination for 10 days.
Figure 8:
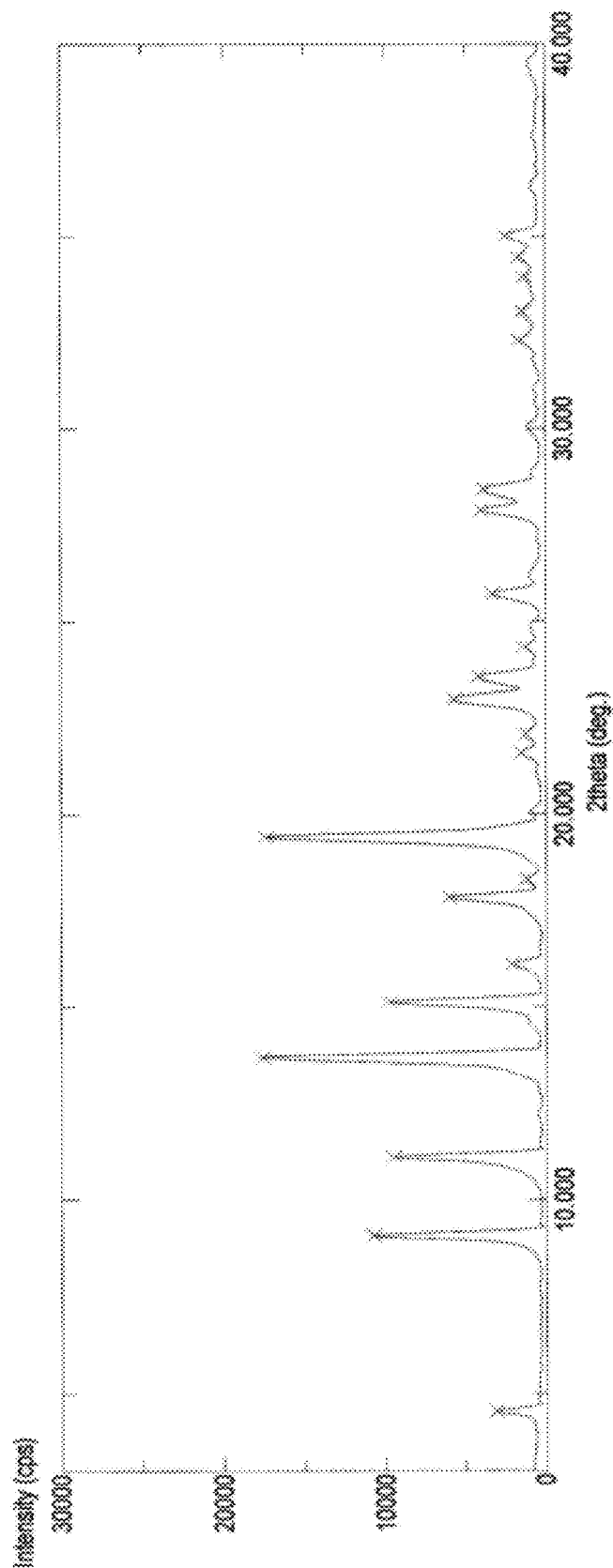
FIG. 8 is an XRPD pattern of the Polymorph I of Dasatinib of this invention after high temperature test of 60° C. for 10 days.
Figures 1, 9:
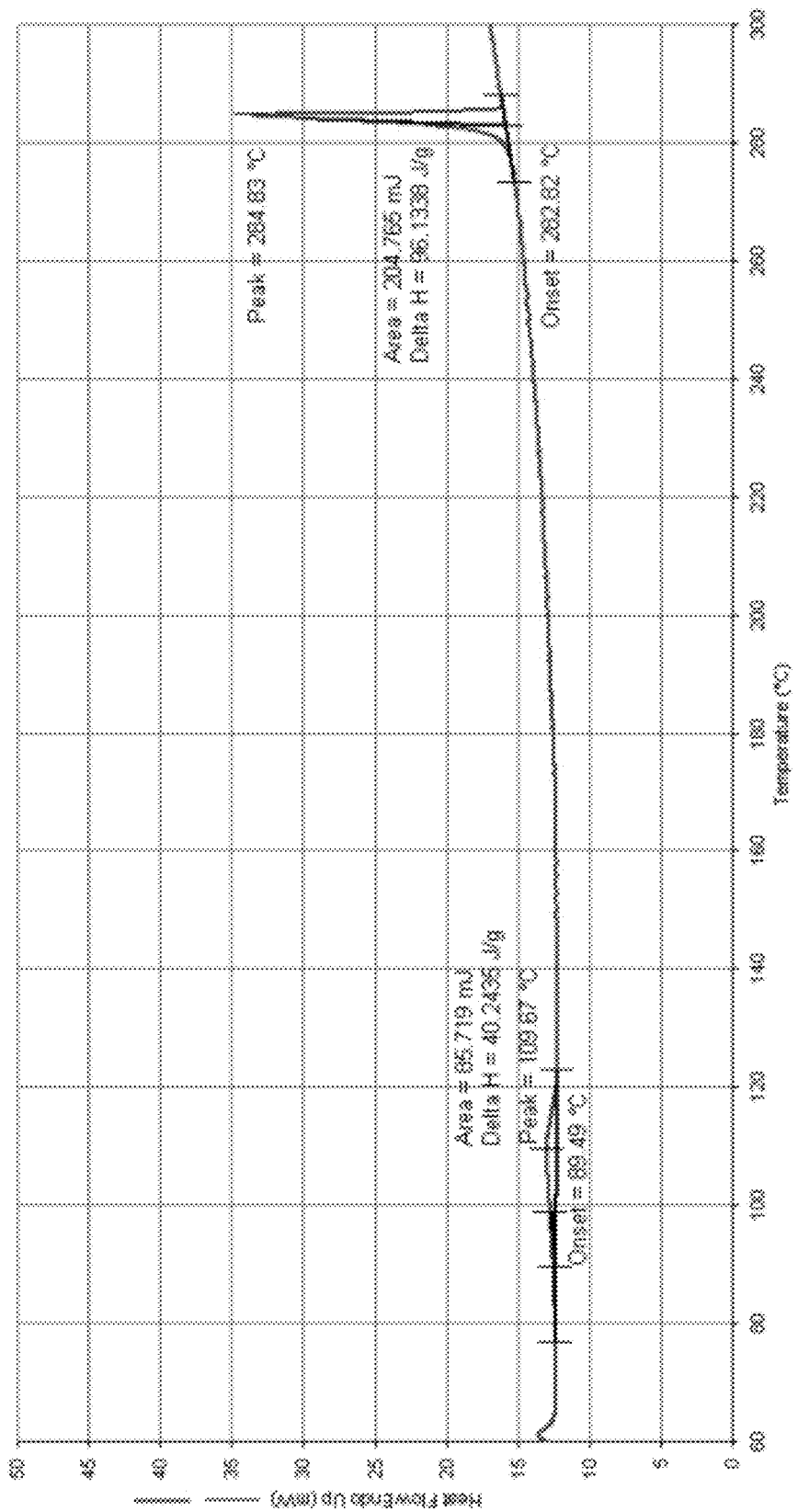
Figures 2, 9:
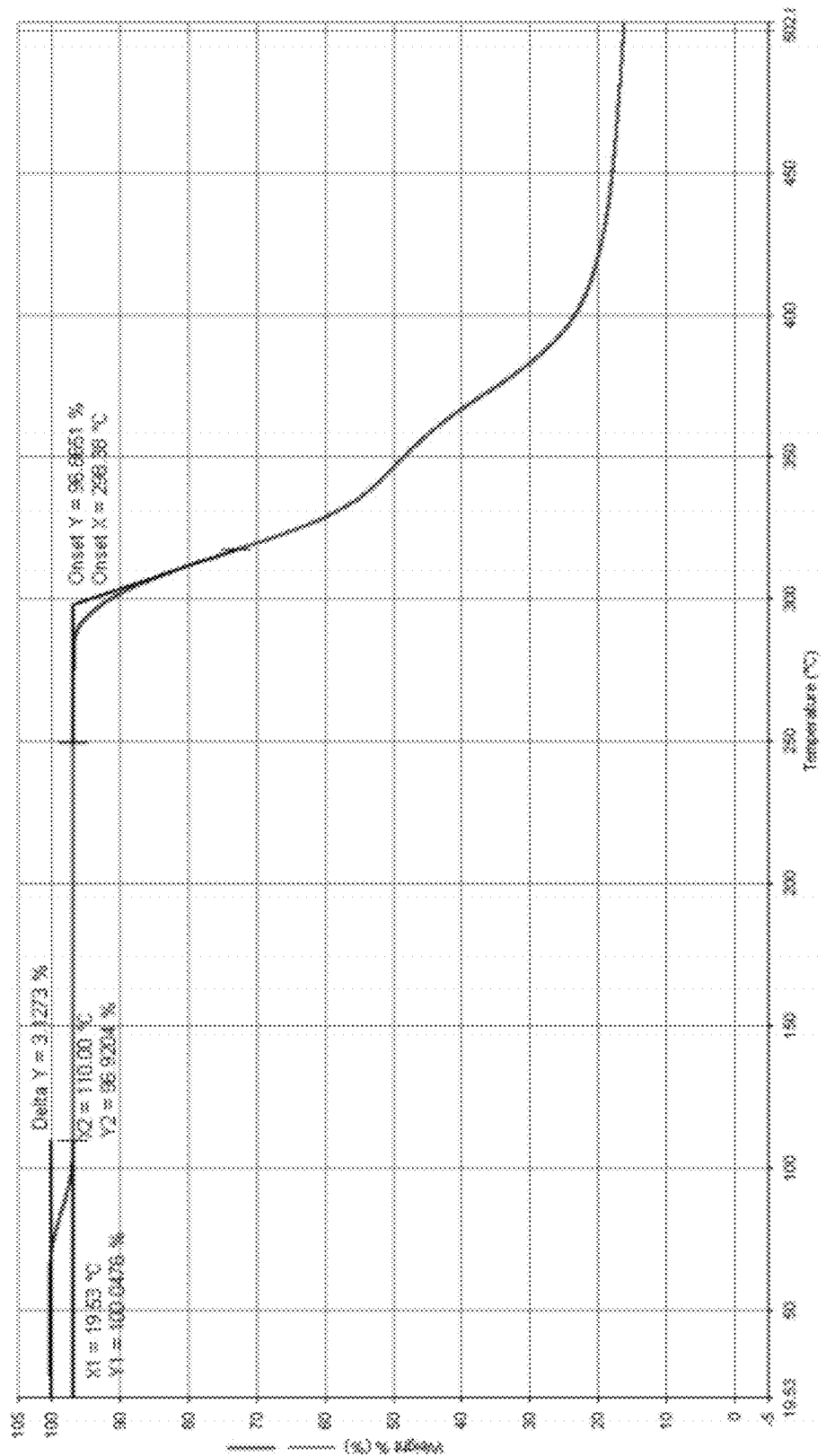
Figure 10:
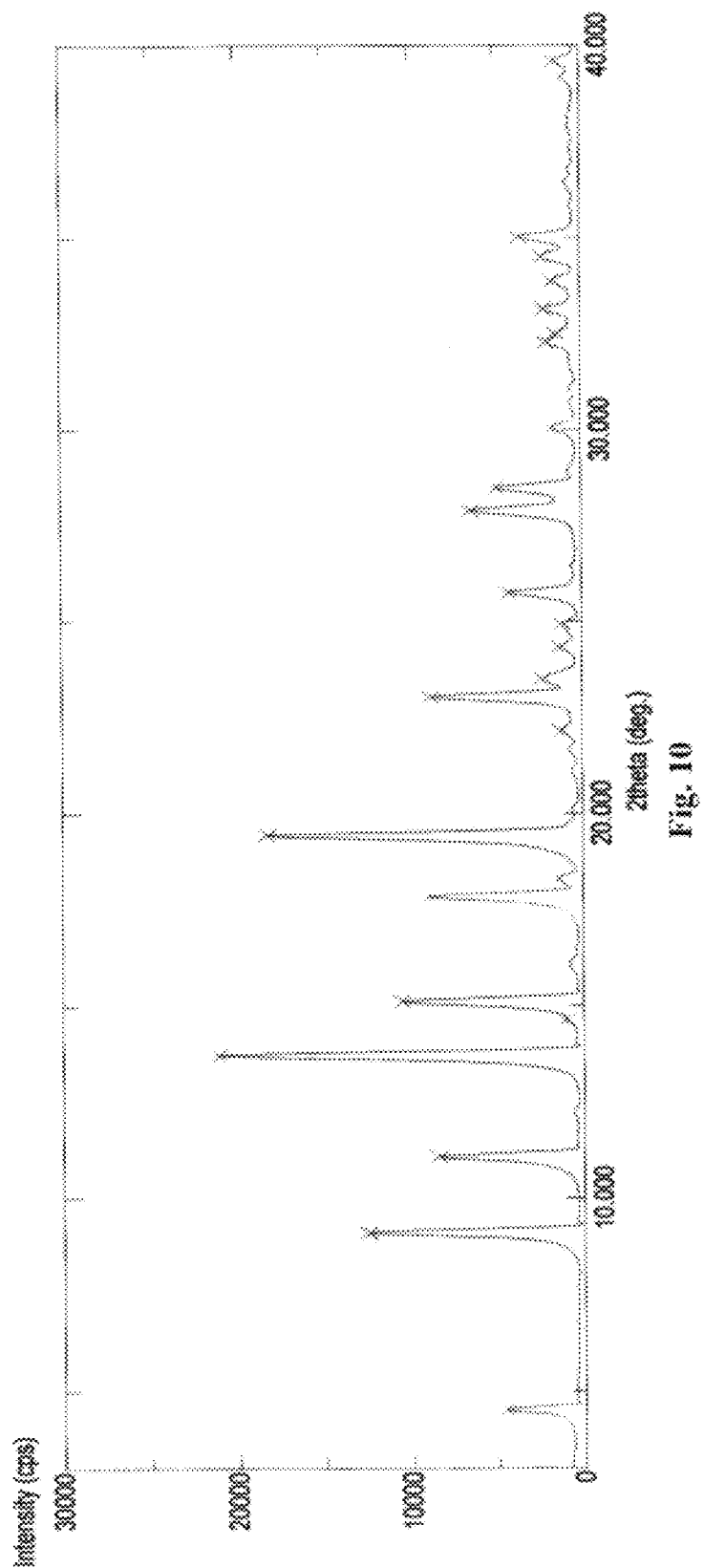
FIG. 10 is an XRPD pattern of the Polymorph I of Dasatinib of this invention after high humidity for 10 days.
Figures 1, 11:
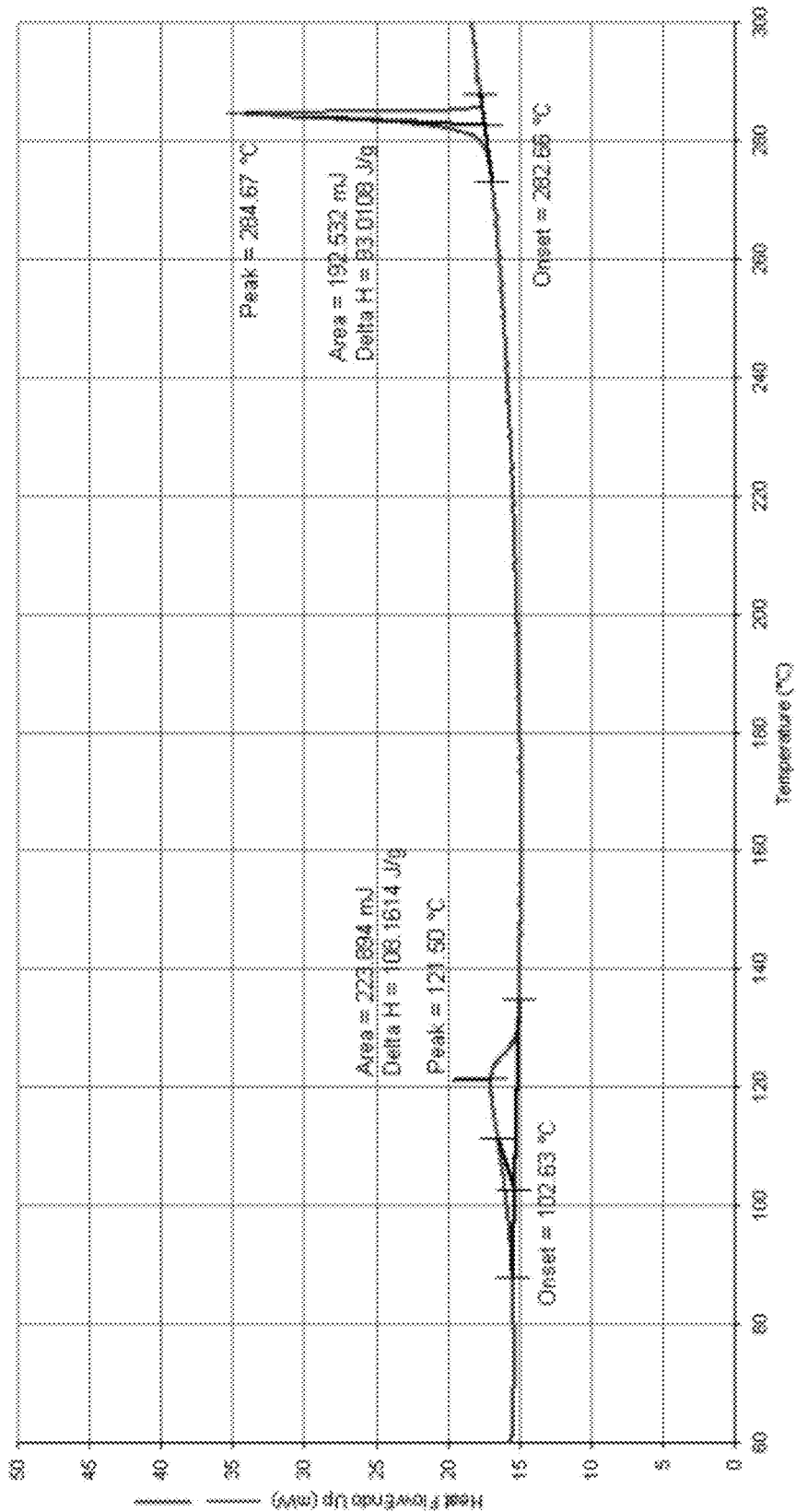
Figure 12:
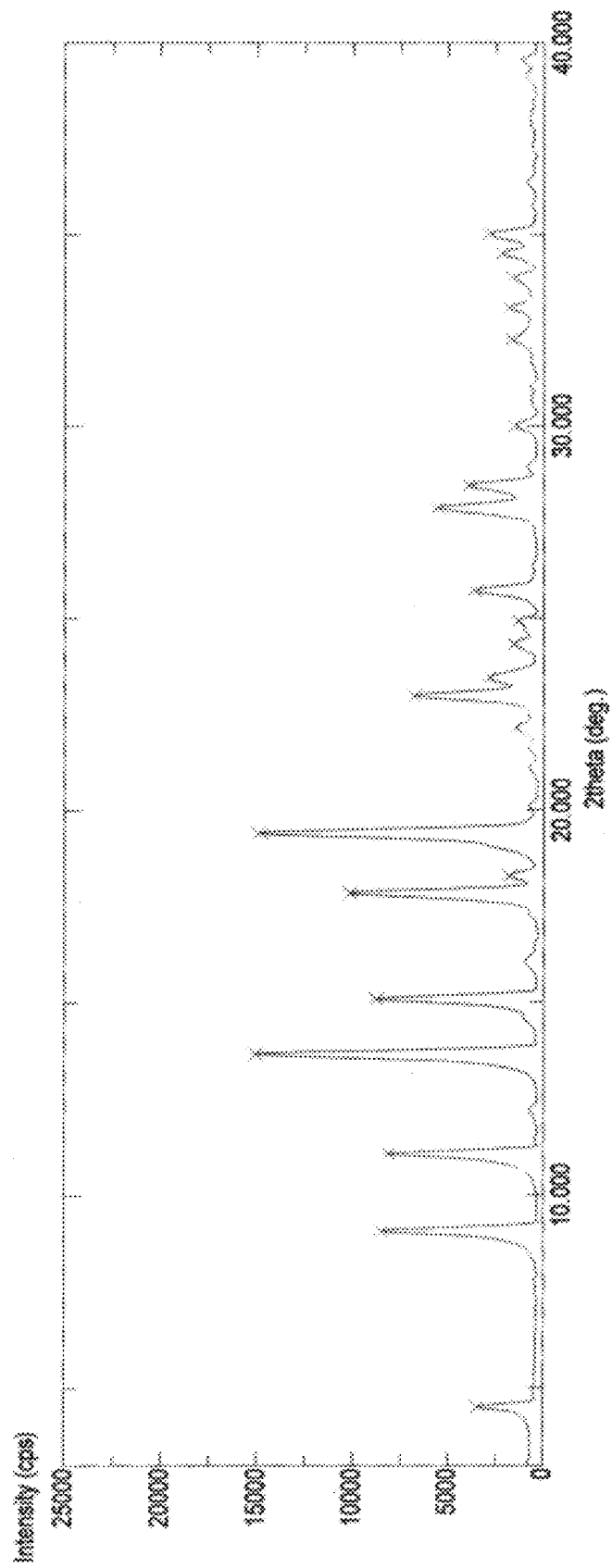
FIG. 12 is an XRPD pattern of the Polymorph I of Dasatinib of this invention after accelerated test at 40° C. for six months.
Figures 1, 13:
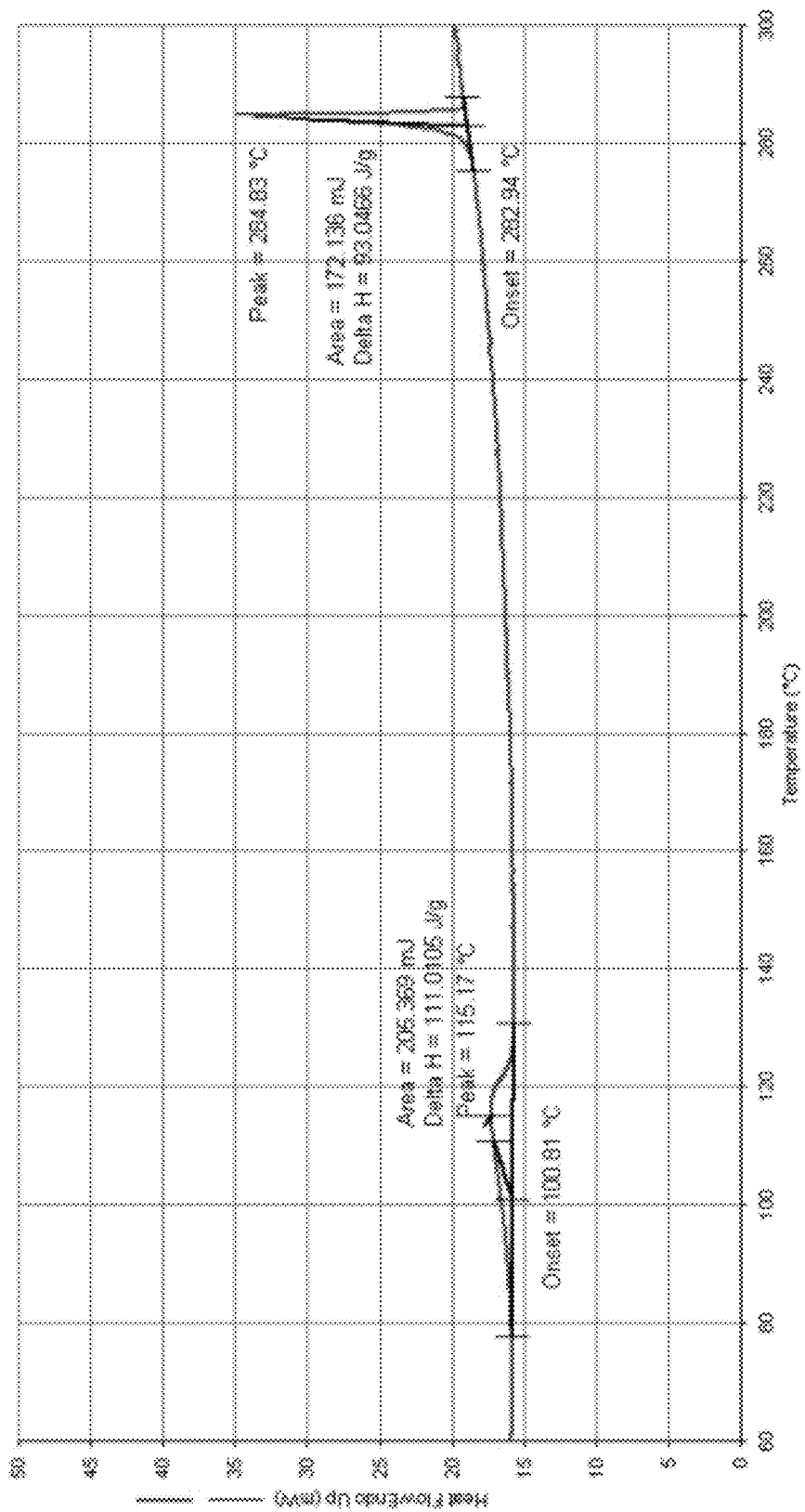
Figures 2, 13:
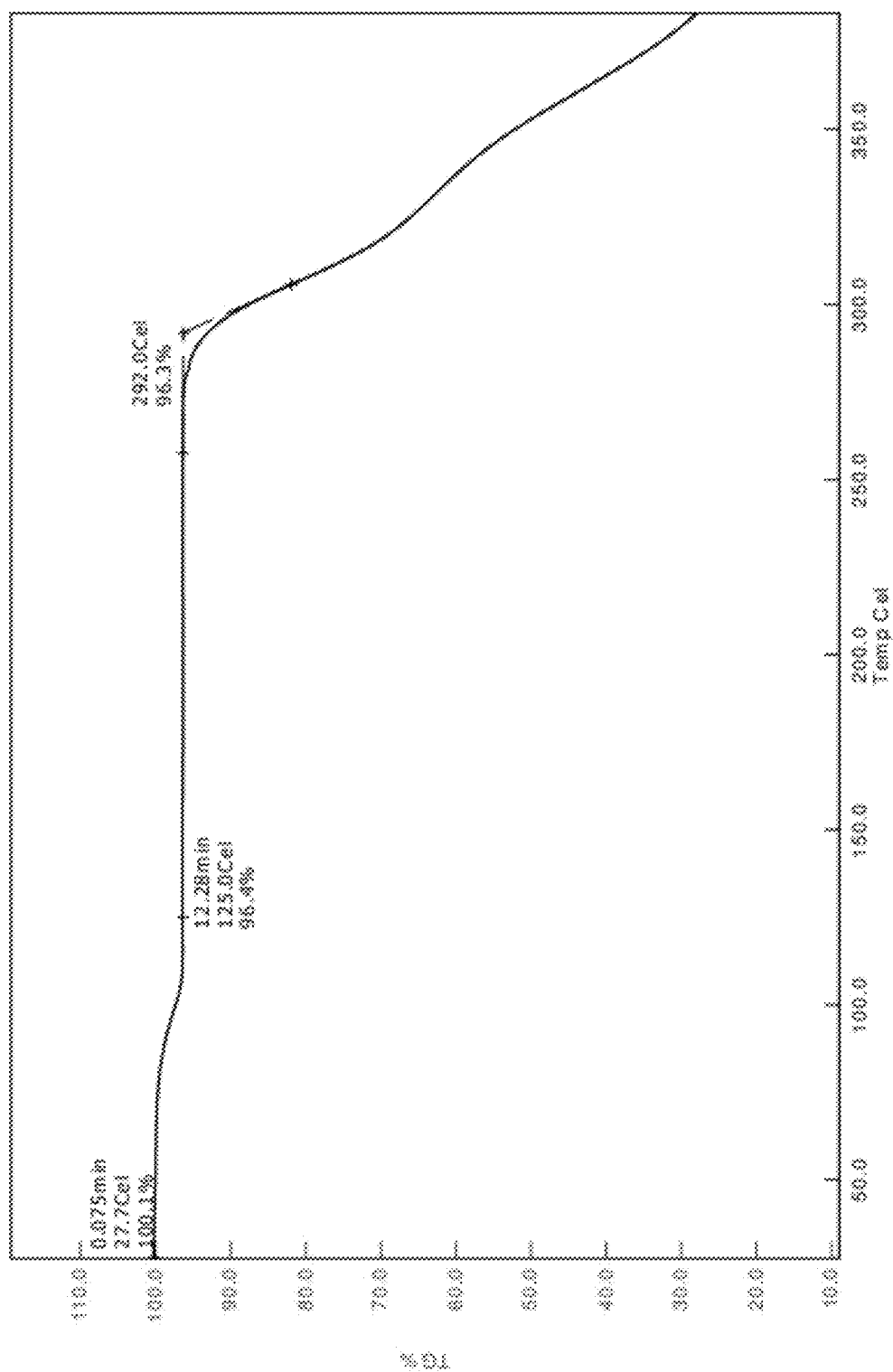

The following items of products prepared by Method A were detected: microscope-crystal form (See. FIG. 1); XRPD Test (See. FIG. 2), IR Test (See. FIG. 3), DSC-TGA Test (See. FIG. 4-1, 4-2), 13C Solid-state NMR Test (See. FIG. 5).

B. Dasatinib (10 g) and DMSO (40 ml) were added into a flask and heated slowly up to 60~70° C. by stirring, after dissolving, the mixture (160 mL) of ethanol and water (1:1) was added under heat preservation. When crystal was precipitated, cooled it down to 0° C. to grow the grains for 10 minutes. Filtrate it and the cake was washed by the mixture of ethanol and water (1:1) and dried under −0.095 MPa at about 50° C. using phosphorus pentoxide as drying aid to give 7.7 g of white solid. Yield was 87%.

| | Contrasts | |
|---|---|---|
| Items | Index of raw material before transformation | Index of Polymorph I |
| Appearance | off-white powder | White crystal powder |
| Related substance | 0.85% | 0.08% |
| KF moisture | 0.67% | 3.58% |
| 70~150 TGA weight loss | 0.72% | 3.67% |

Example 2

Preparation of the Polymorph II

A. Dasatinib (10 g) and DMF (40 ml) were added into a flask and dissolved by stirring and heating up to 60~70° C. The above-mentioned solution of Dasatinib in DMF was put in a sealed environment of acetone, where the volume of acetone was 300 mL. Acetone was evaporated at room temperature to its refluxing temperature into the solution of Dasatinib in DMF. After a few hours even up to a few days heaped-up crystal was precipitated, it was settled statically for several hours even up to several days more. Filtrate it and the cake was washed by acetone and dried under −0.095 MPa at about 50° C. using phosphorus pentoxide as drying aid to give 6.1 g of white solid. Yield was 61%.

| | Contrasts | |
| --- | --- | --- |
| Items | Index of raw material before transformation | Index of Polymorph 多晶型物 I 指标 |
| Appearance | off-white powder | White crystal powder |
| Related substance | 0.75% | 0.19% |
| KF moisture | 0.67% | 0.01% |
| 100~220 TGA weight loss | 0.72% | 9.20% |

Figures 1, 15:
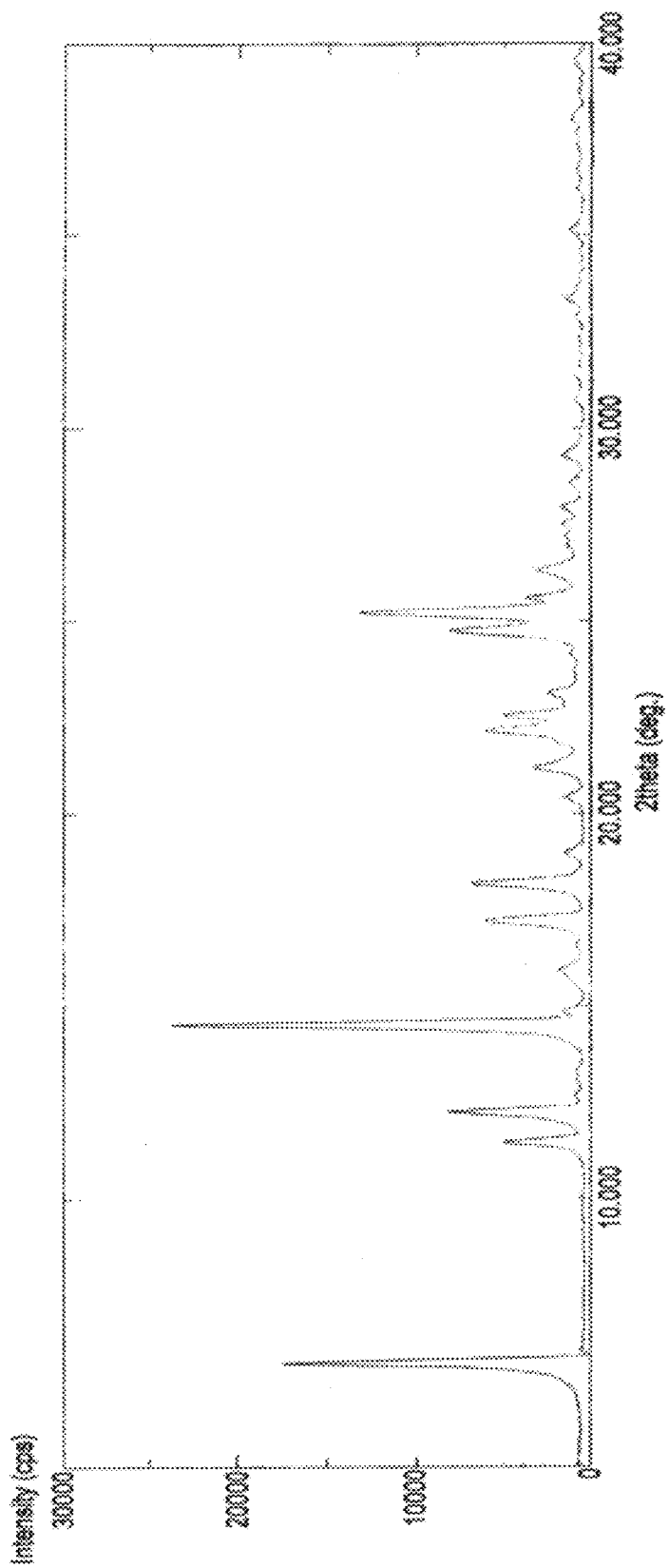
Figures 2, 15:
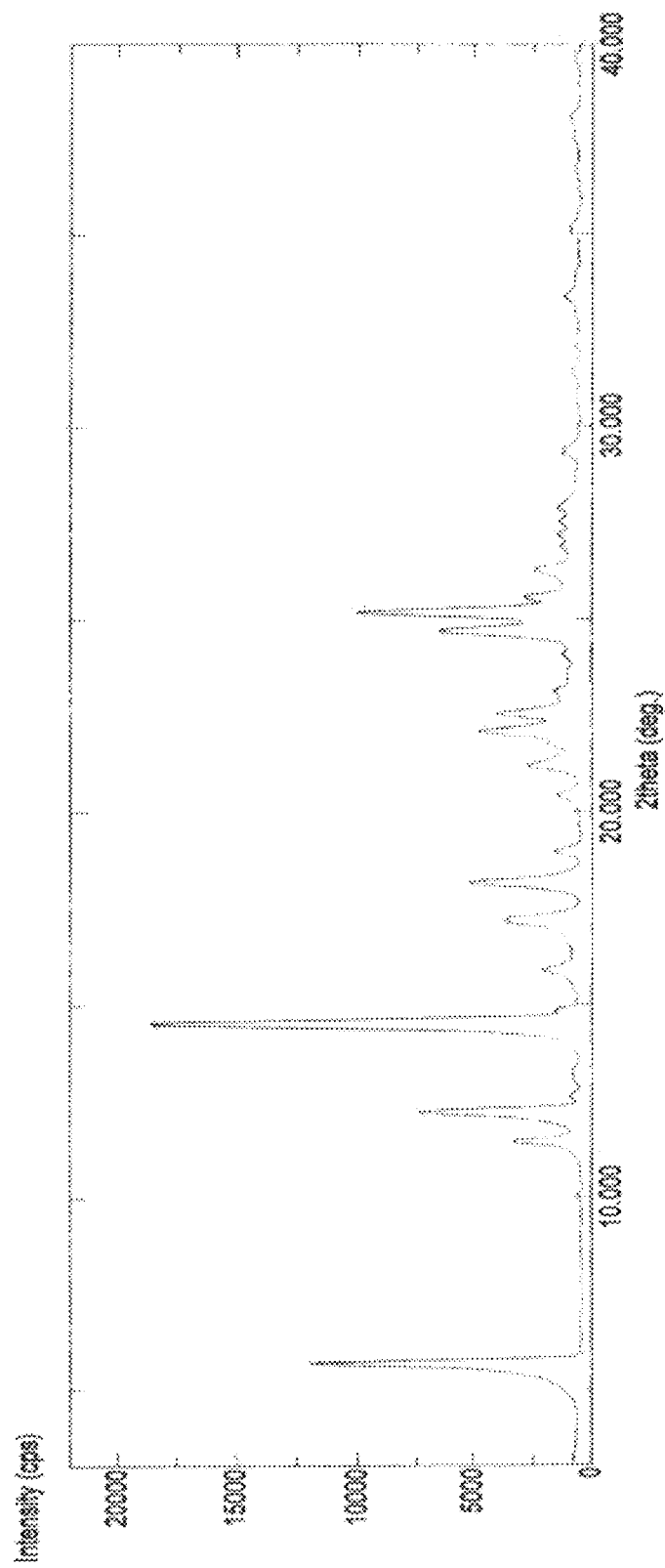
Figure 16:
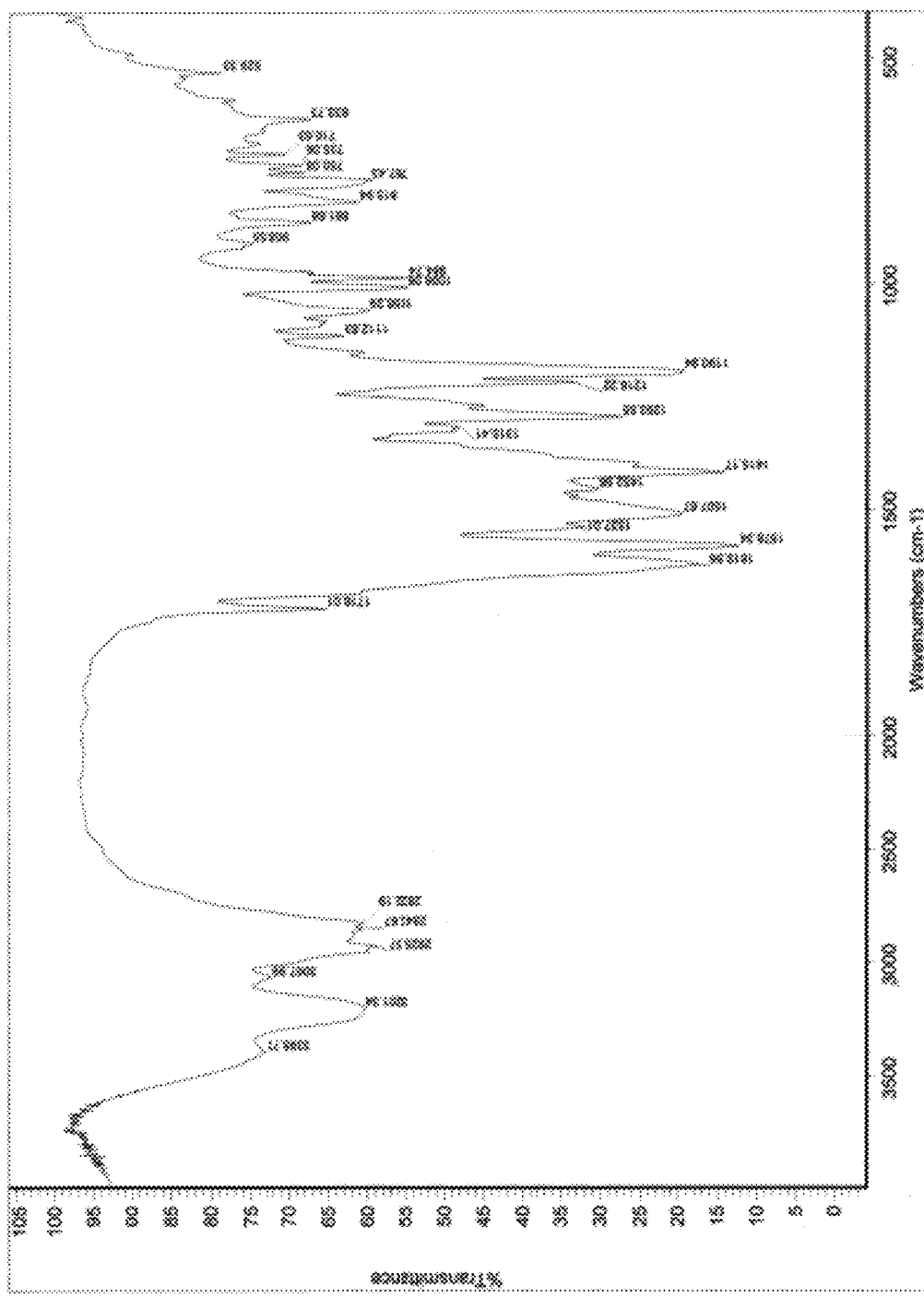
FIG. 16 is an IR diagram of the Polymorph II of Dasatinib of this invention.
Figures 1, 17:
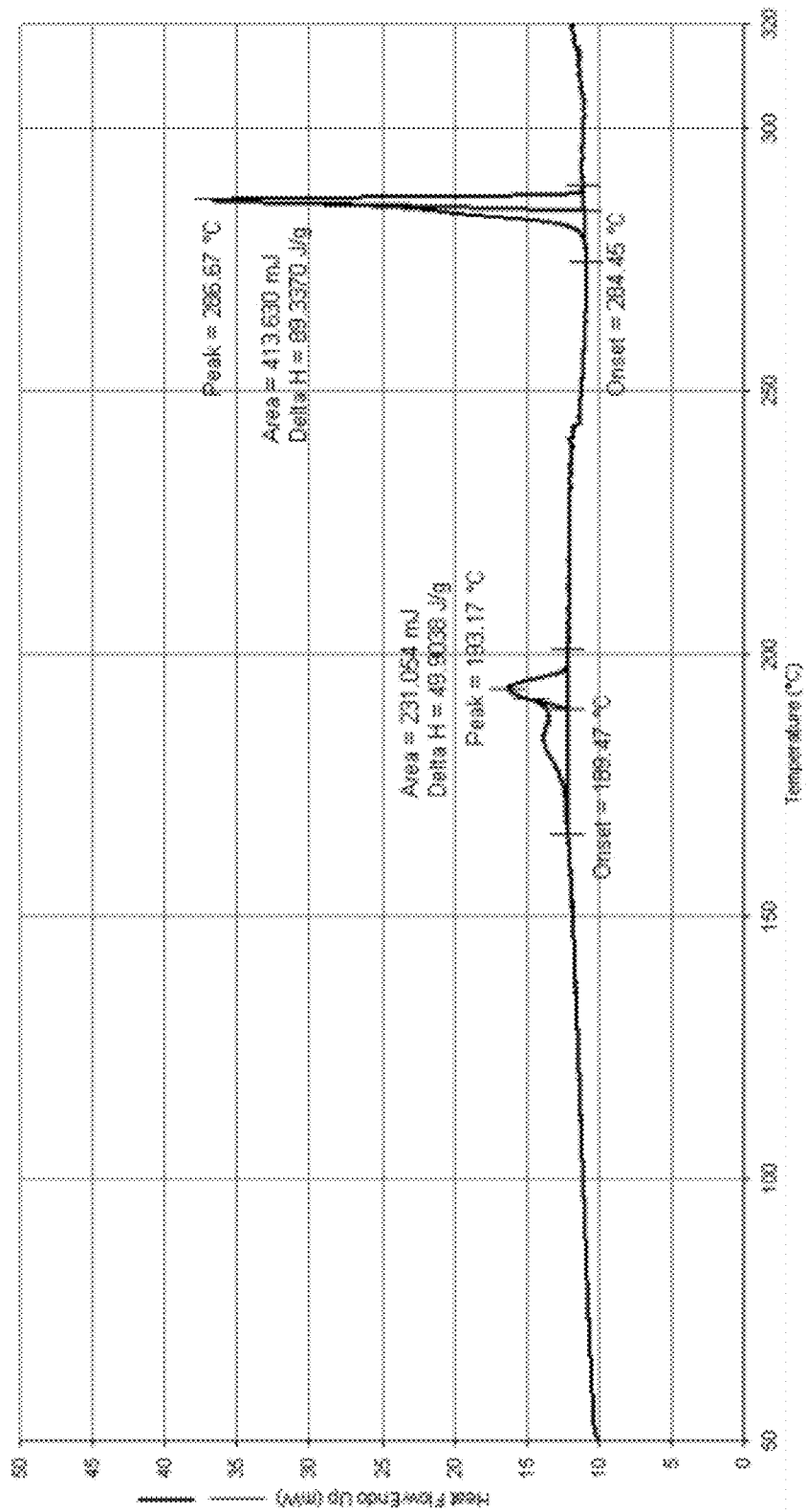
Figures 2, 17:
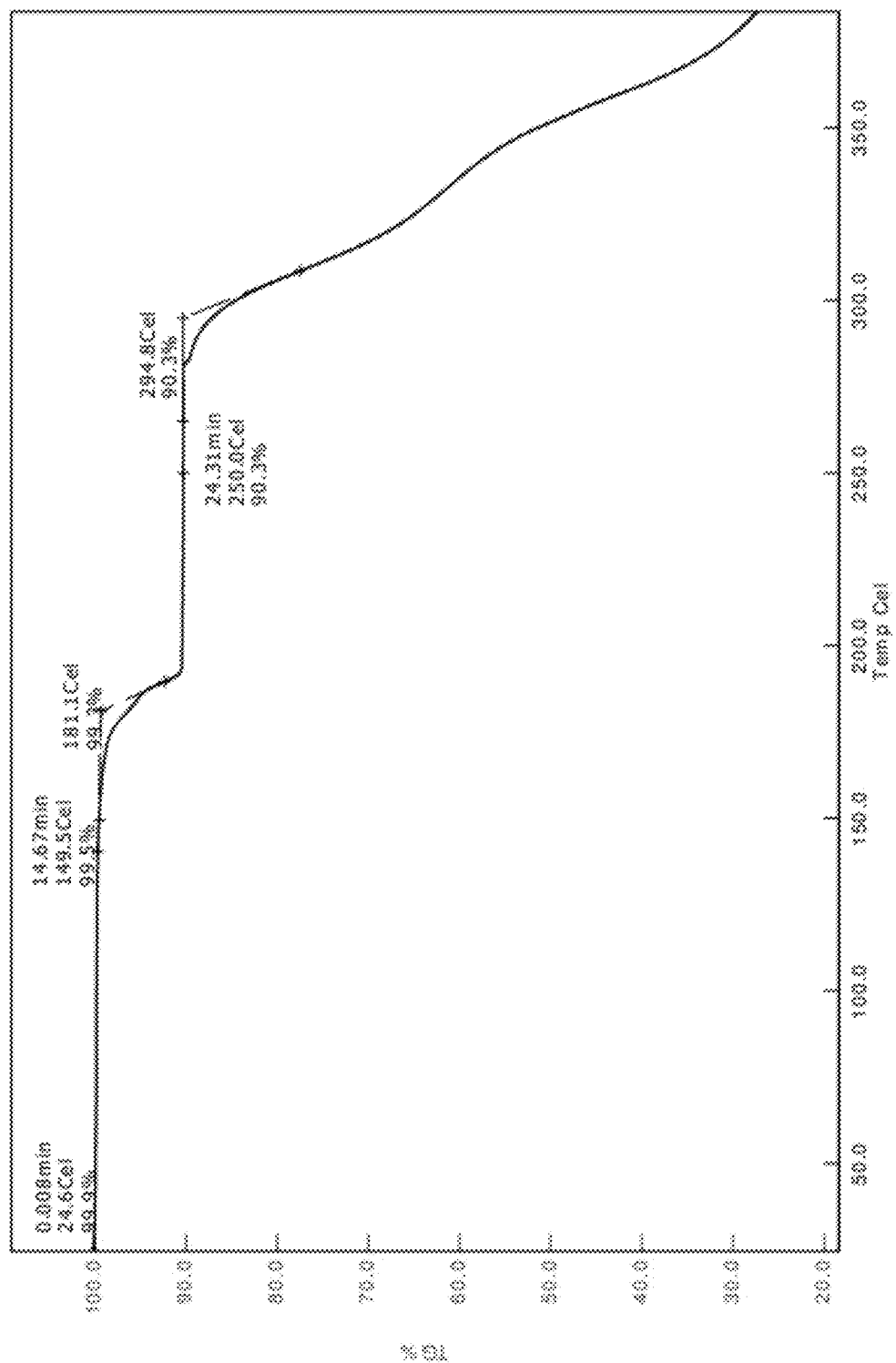
Figure 18:
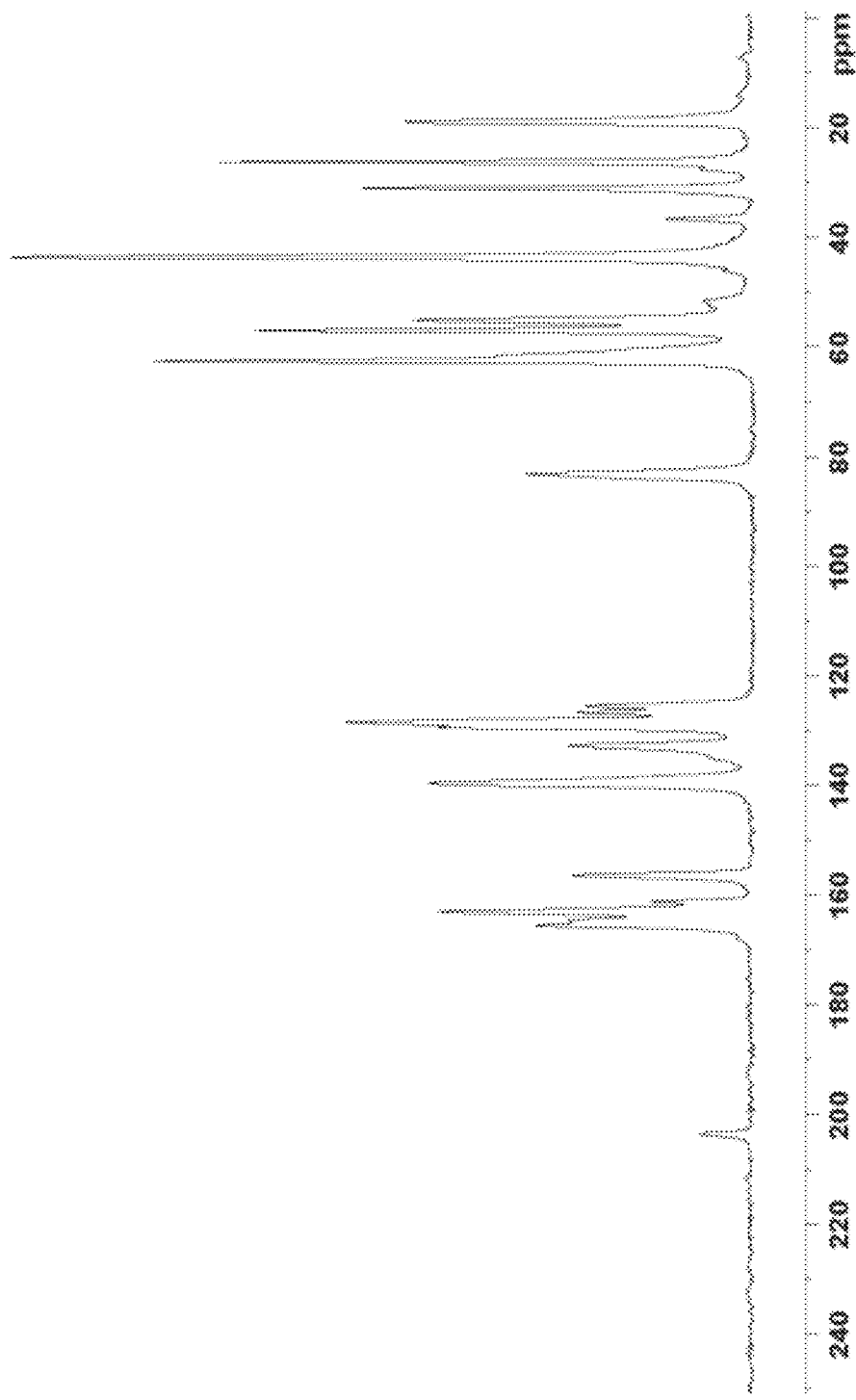
FIG. 18 is a 13C solid-state NMR spectrum of the Polymorph II of Dasatinib of this invention.
Figure 19:
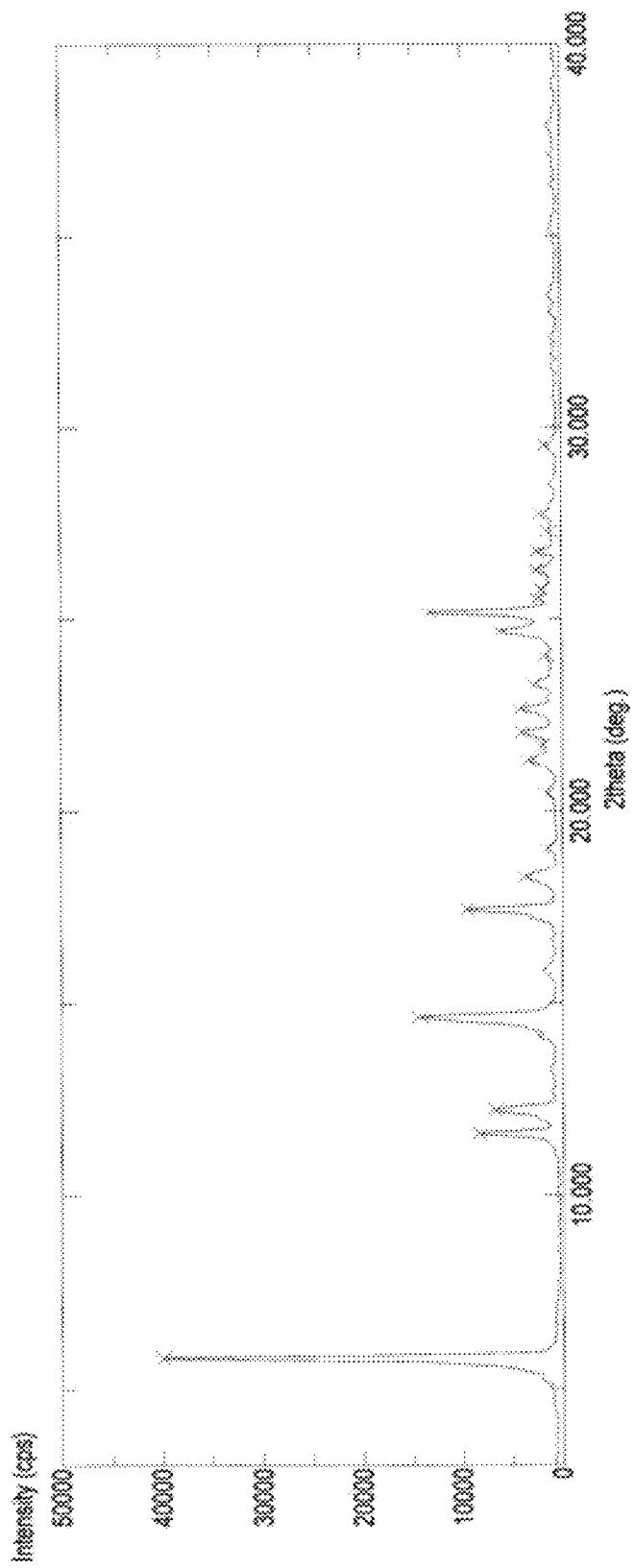
FIG. 19 is an XRPD pattern of the Polymorph II of Dasatinib of this invention after strong illumination for 10 days.
Figure 20:
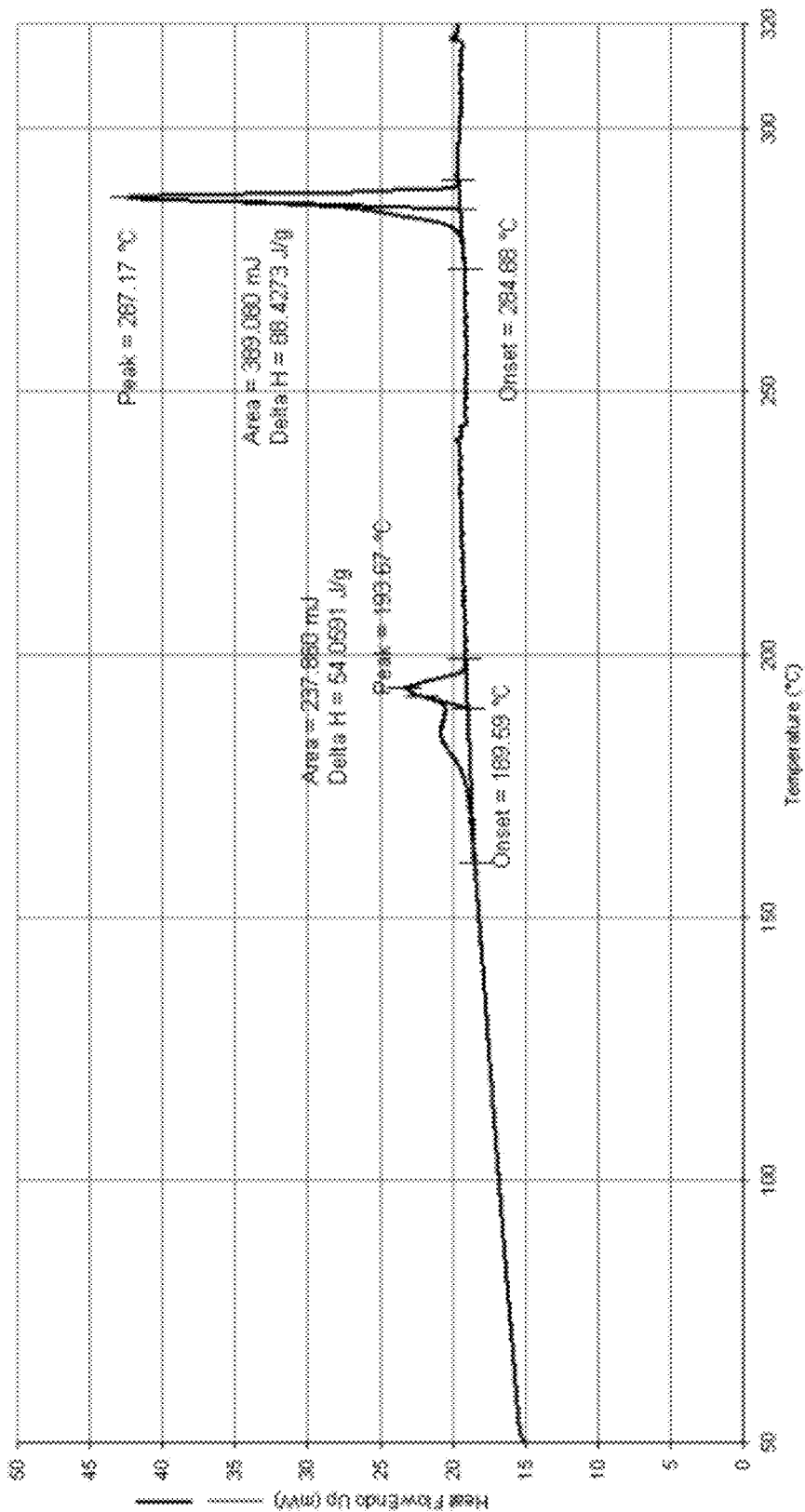
FIG. 20 is a DSC diagram of the Polymorph II of Dasatinib of this invention after strong illumination for 10 days.
Figure 21:
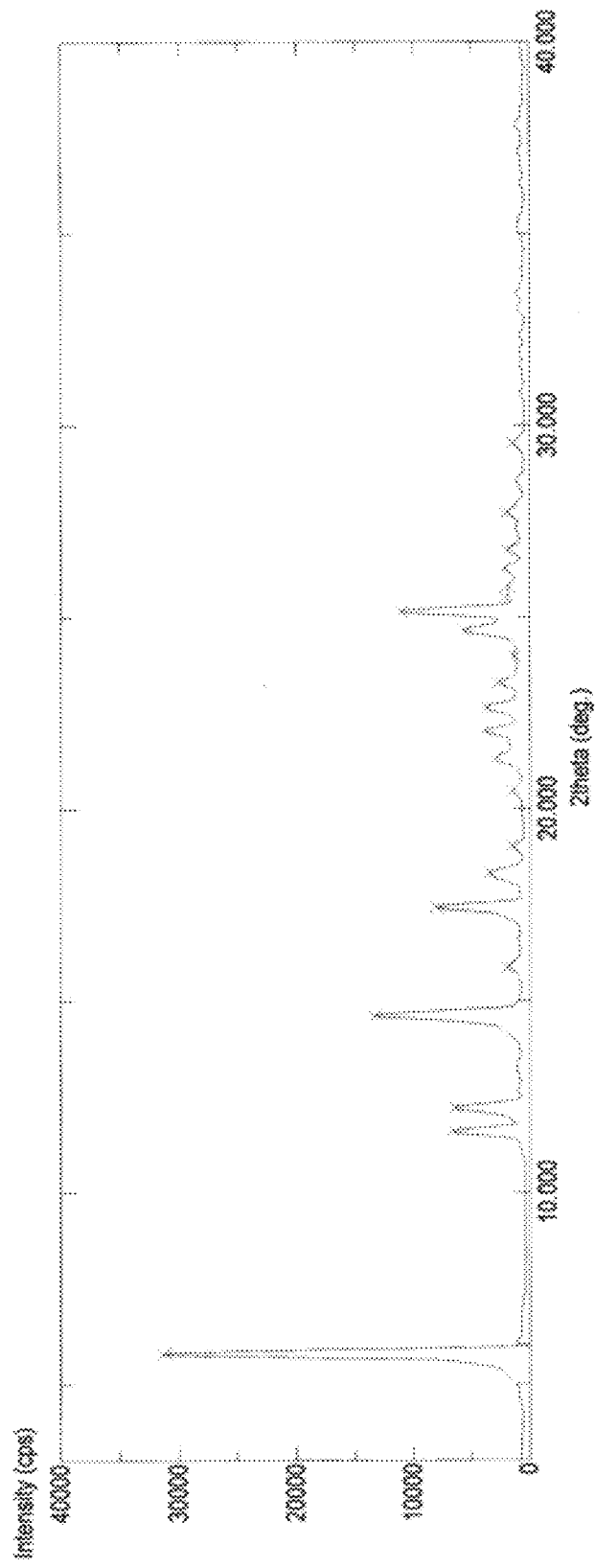
FIG. 21 is an XRPD pattern of the Polymorph II of Dasatinib of this invention after high temperature test of 60° C. for 10 days.
Figure 22:
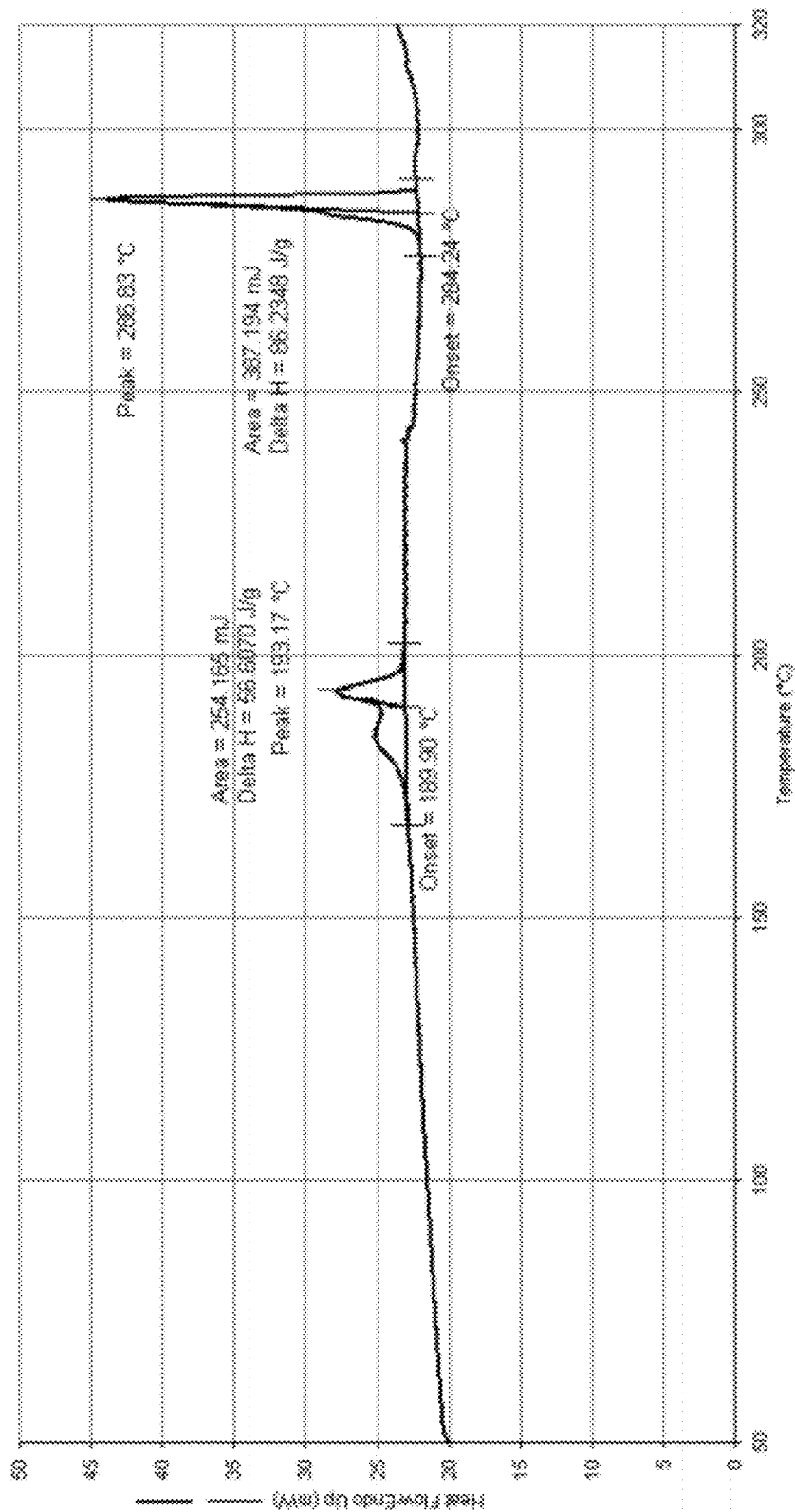
FIG. 22 is a DSC diagram of the Polymorph II of Dasatinib of this invention after high temperature test of 60° C. for 10 days.
Figure 23:
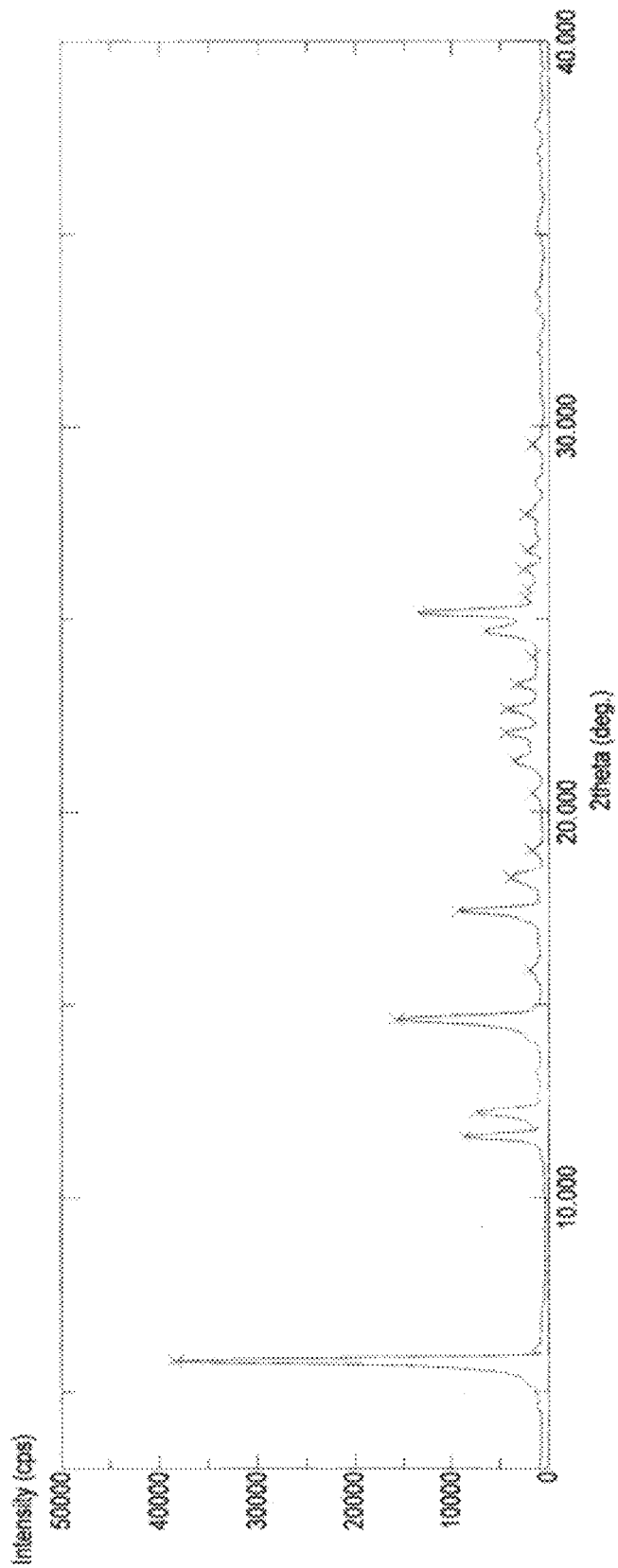
FIG. 23 is an XRPD pattern of the Polymorph II of Dasatinib of this invention after high humidity for 10 days.
Figures 1, 24:
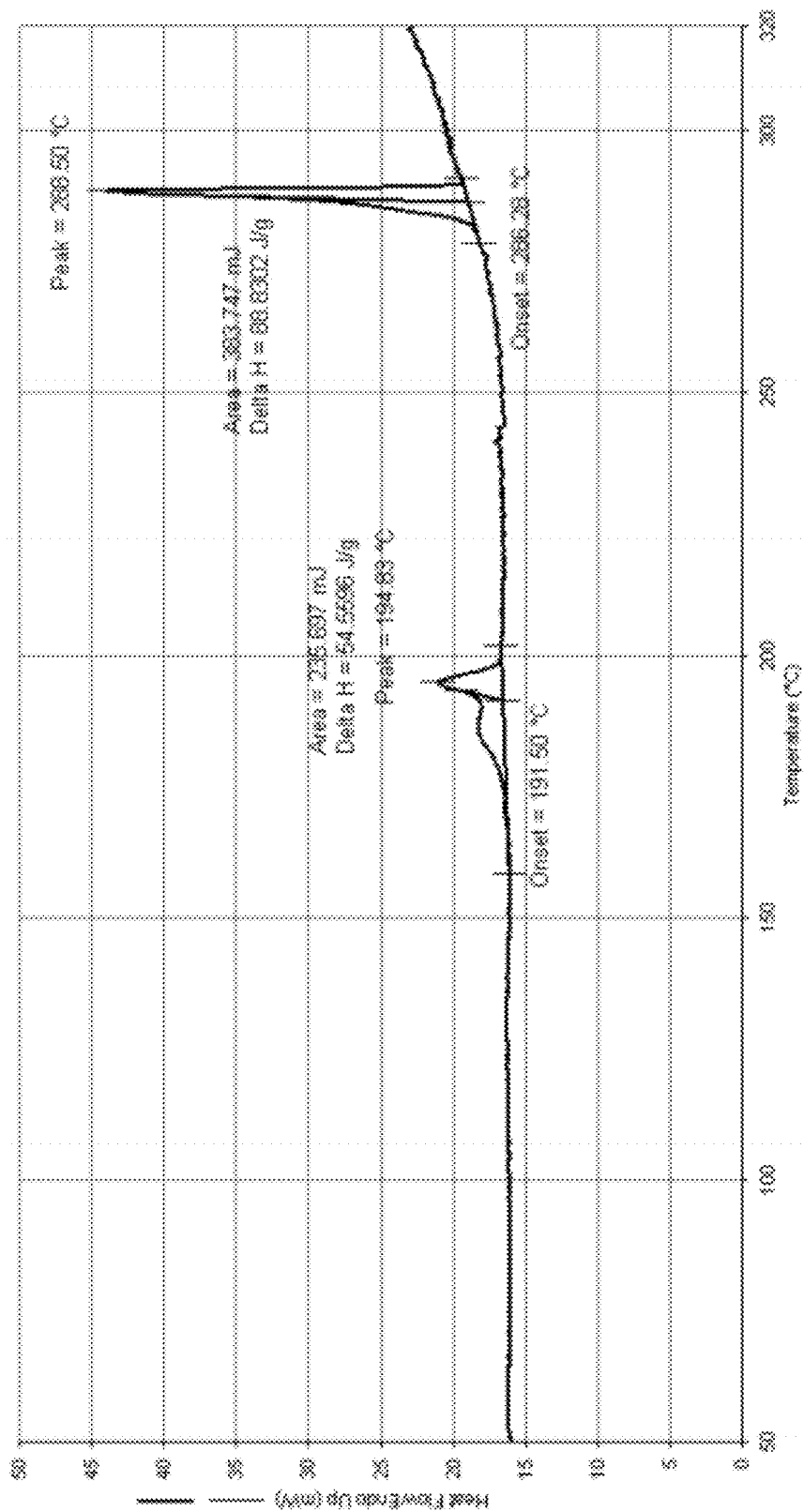
Figures 2, 24:
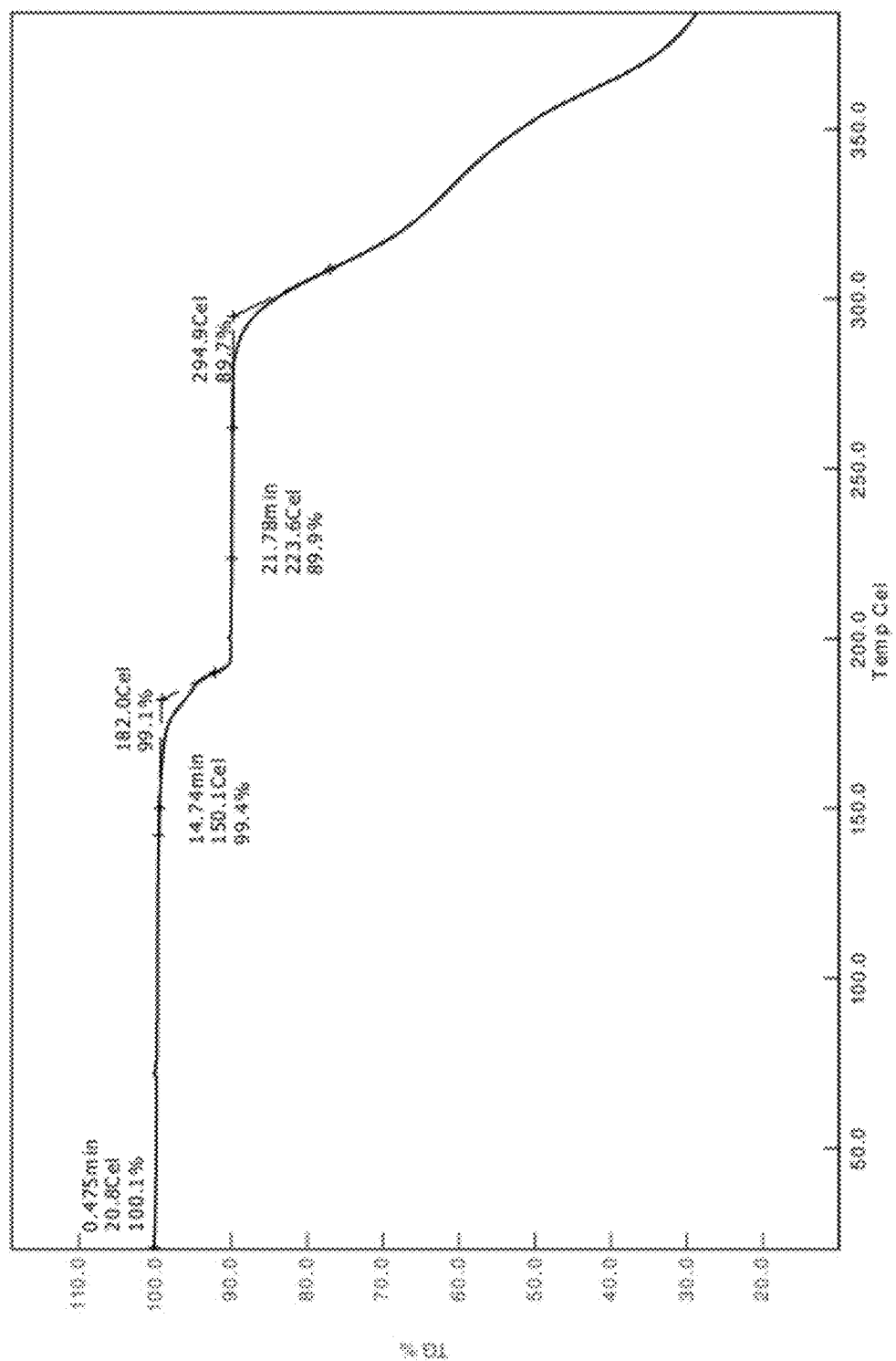
Figure 25:
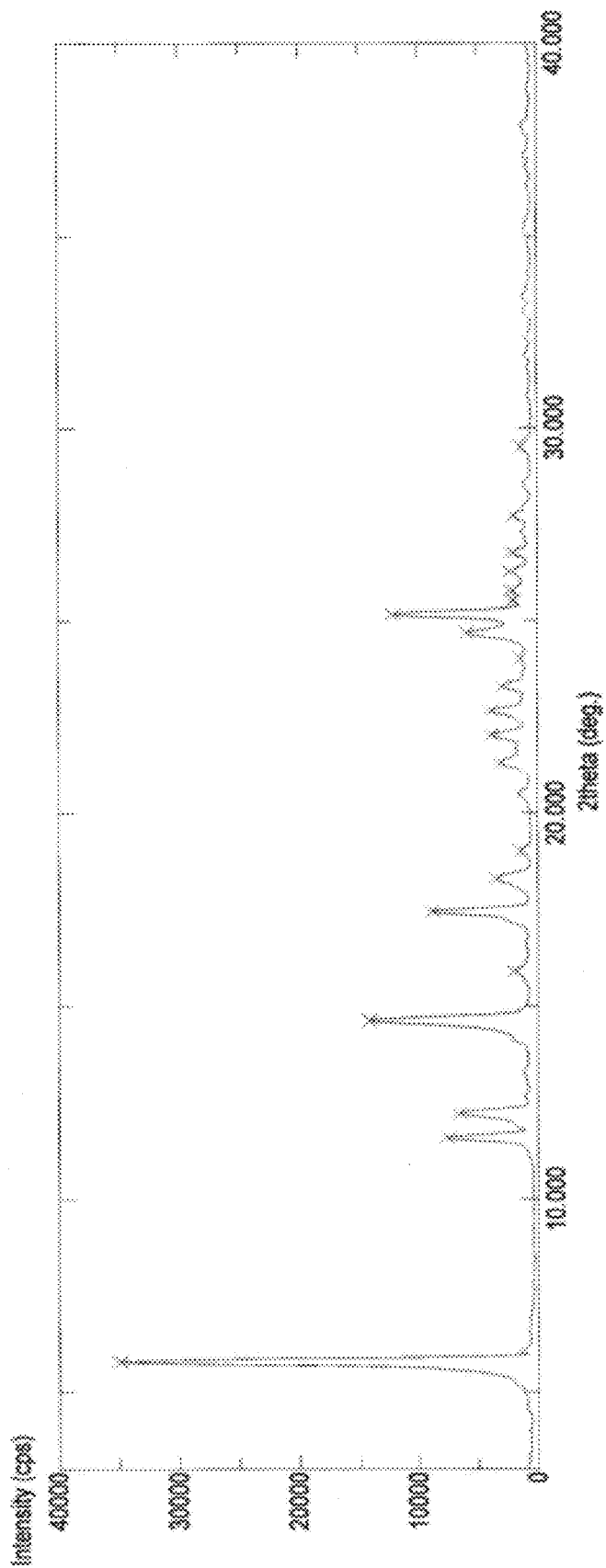
FIG. 25 is an XRPD pattern of the Polymorph II of Dasatinib of this invention after accelerated test at 40° C. for six months.
Figures 1, 26:
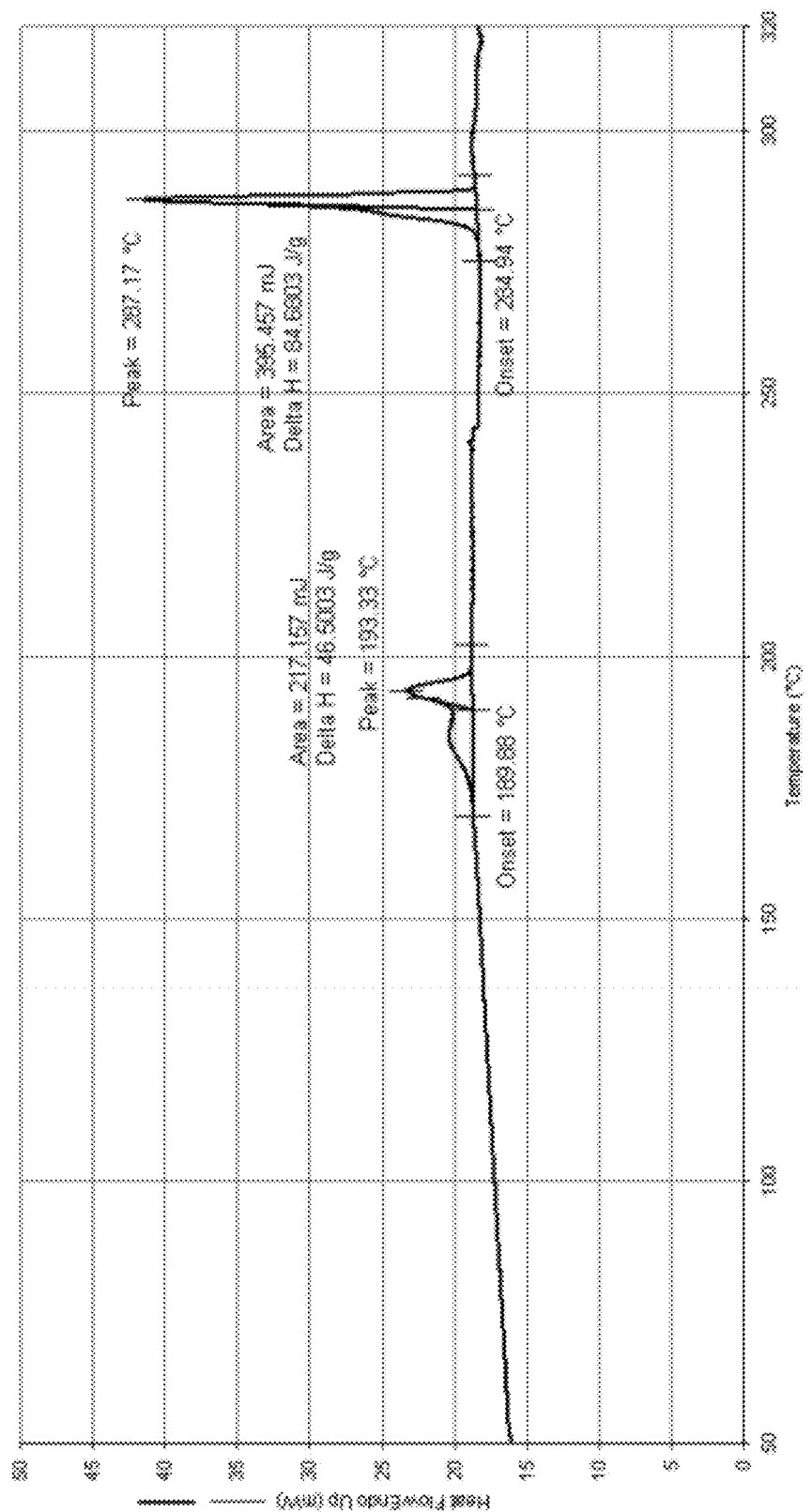
Figures 2, 26:
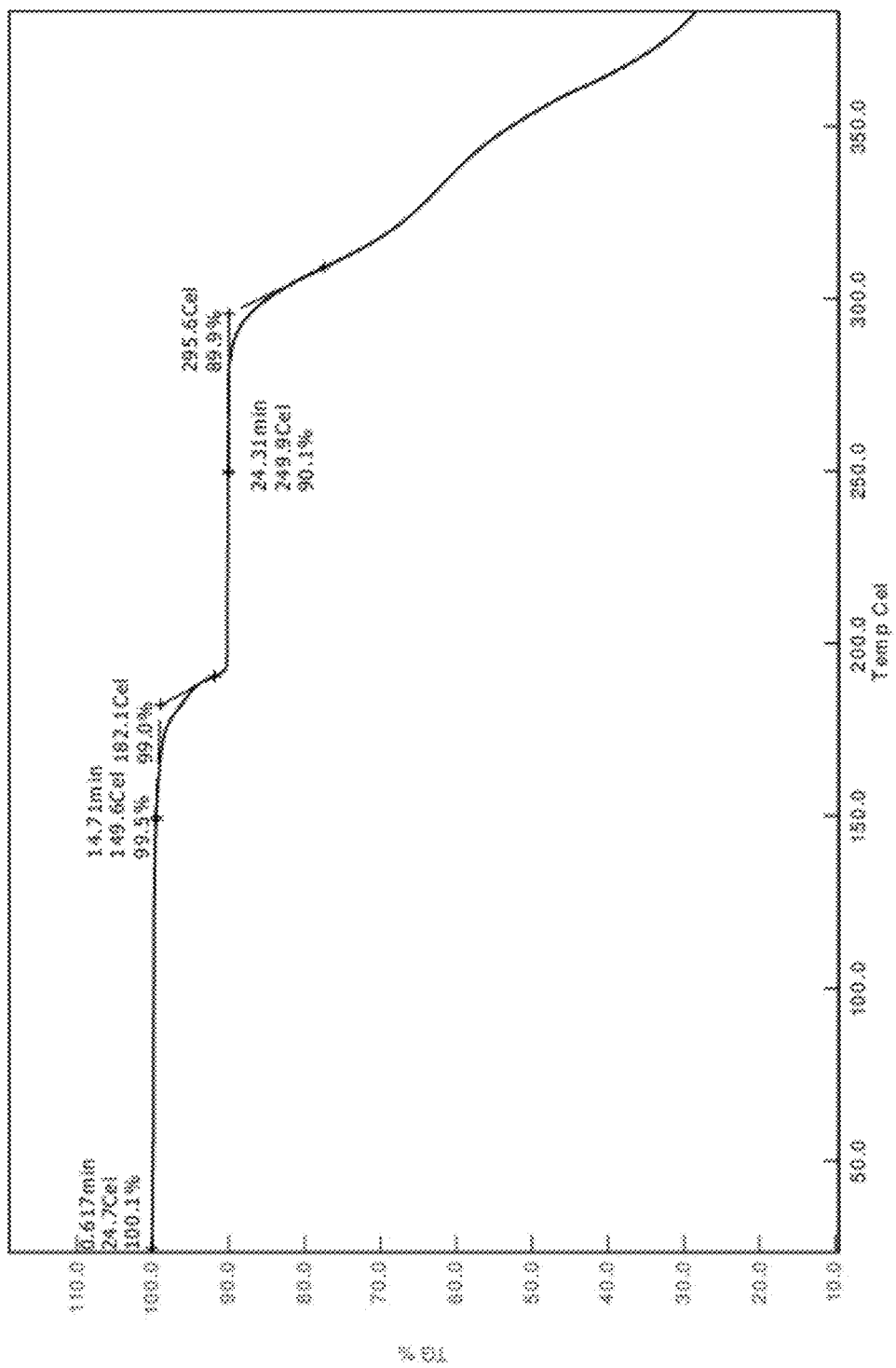
Figure 28:
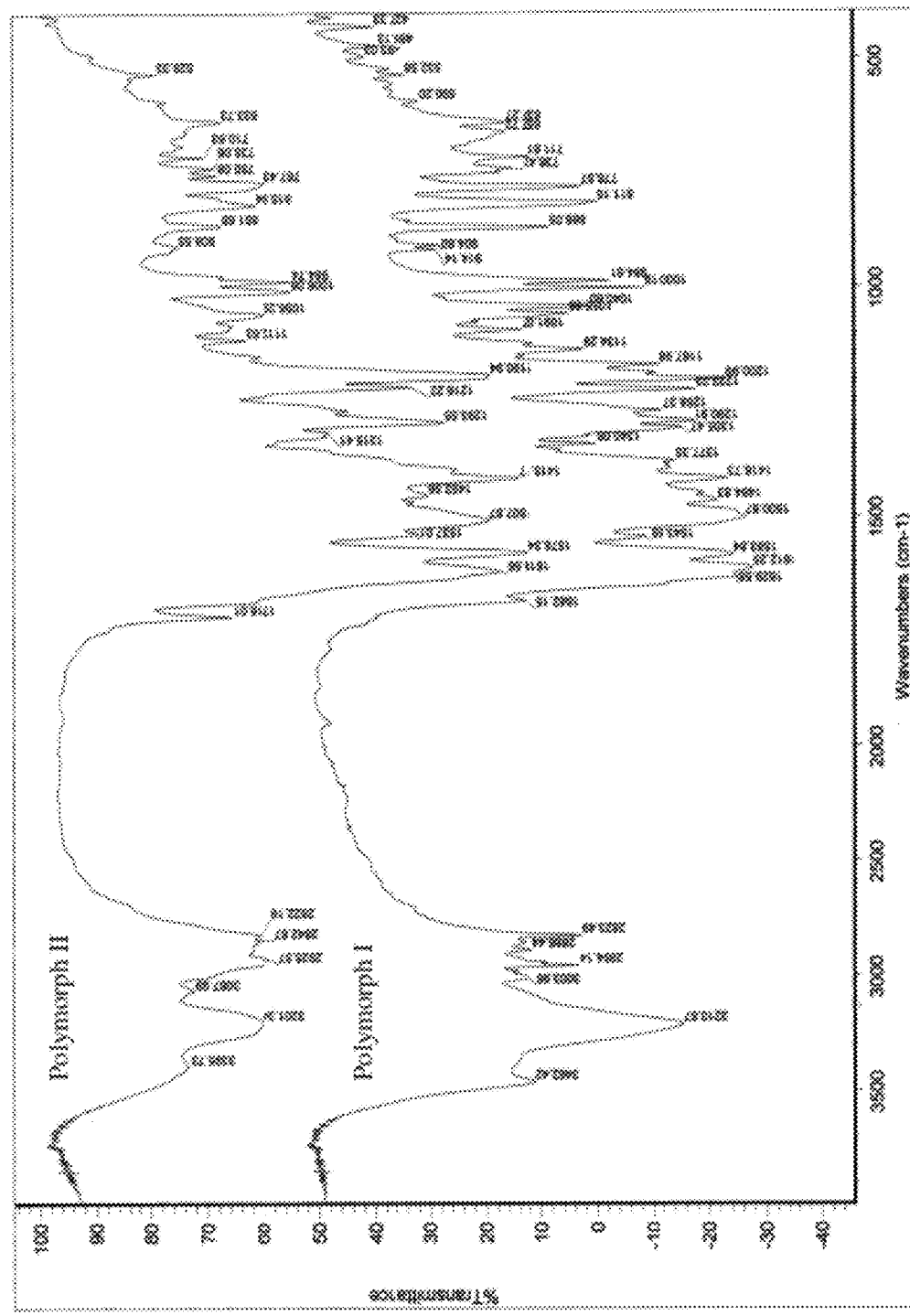
FIG. 28 is a comparative IR spectrum of the Polymorph I and II of Dasatinib of this invention.
Figure 30:
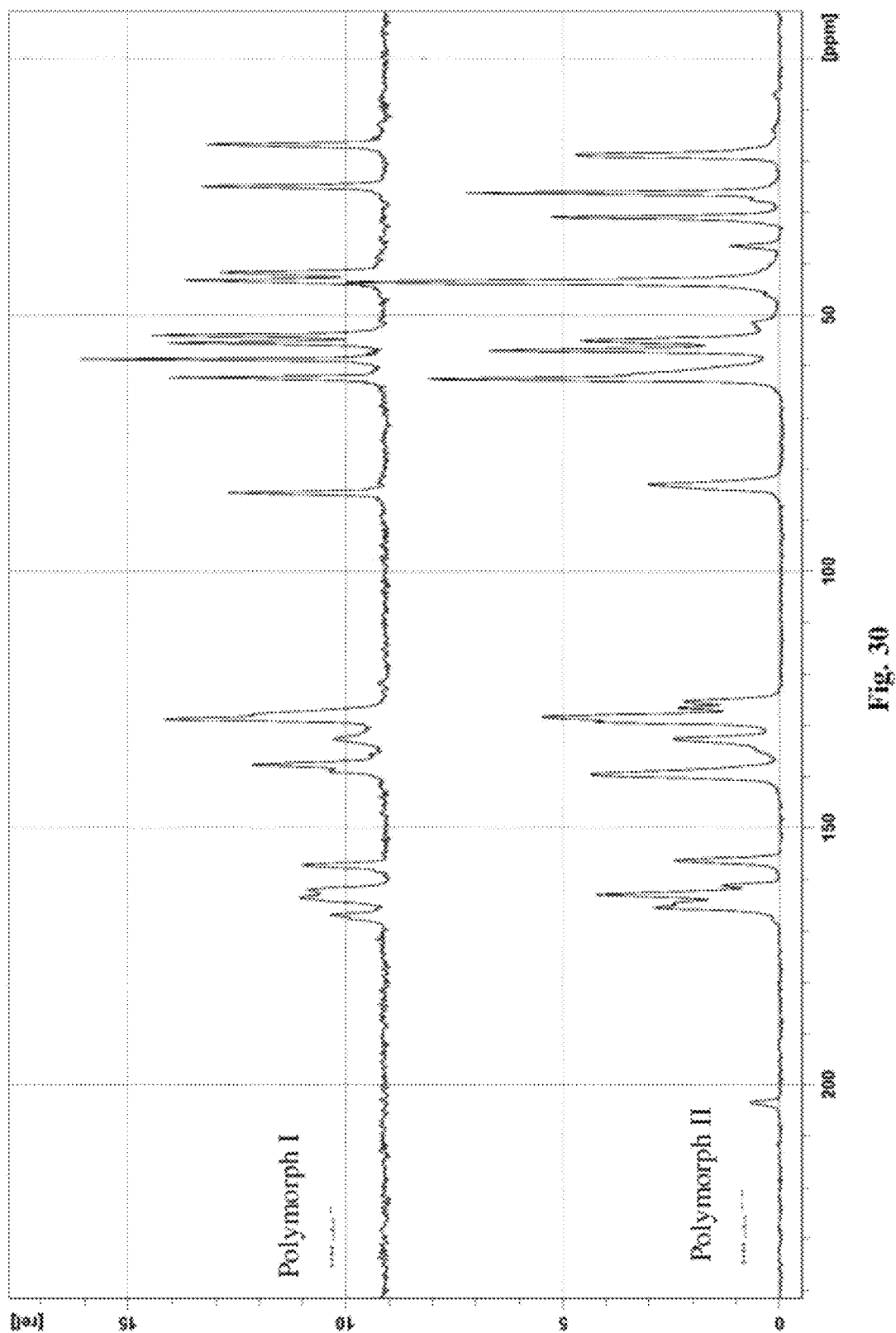
FIG. 30 is a comparative 13C solid-state NMR spectrum of the Polymorph I and II of Dasatinib of this invention.

The following items of products prepared by Method A were detected: microscope-crystal form (See. FIG. 14A, 14B); XRPD Test (See. FIG. 15-1), IR Test (See. FIG. 16), DSC-TGA Test (See. FIG. 17-1, 17-2), 13C Solid-state NMR Test (See. FIG. 18).

B. Dasatinib (10 g) and DMSO (40 ml) were added into a flask and dissolved by stirring and heating up to 60~70° C. The above-mentioned solution of Dasatinib in DMSO was put in a sealed environment of ethyl acetate, where the volume of ethyl acetate was 300 mL. Ethyl acetate was evaporated at room temperature to its refluxing temperature into the solution of Dasatinib in DMSO. After a few hours even up to a few days heaped-up crystal was precipitated, it was settled statically for several hours even up to several days more. Filtrate it and the cake was washed by acetone and dried under −0.095 MPa at about 50° C. using phosphorus pentoxide as drying aid to give 8.1 g of white solid. Yield was 81%.

| | Contrasts | |
| --- | --- | --- |
| Items | Index of raw material before transformation | Index of Polymorph II |
| Appearance | off-white powder | White crystal powder |
| Related substance | 0.75% | 0.16% |
| KF moisture | 0.67% | 0.51% |
| 100~220 TGA weight loss | 0.72% | 8.75% |

The following item of products prepared by Method B were detected: XRPD (See. FIG. 15-2);

Example 3

Formulation and Preparation Method of Dasatini Capsules

According to the below-mentioned methods, several excipients and the Polymorph I or II of Dasatinib or a mixture of the above-mentioned polymorphs in any ratio were formulated into capsules containing 50 mg per capsule.

| | Amount (g/1000 tablets) | |
| --- | --- | --- |
| Active ingredient and Excipients | Formlation 1 | Formulation 2 |
| Dasatinib (I, II) | 50 g | 50 g |
| lactose | 80 g | 65 g |

-continued

| | Amount (g/1000 tablets) | |
| --- | --- | --- |
| Active ingredient and Excipients | Formlation 1 | Formulation 2 |
| microcrystal cellulose | 55 g | 65 g |
| sodium carboxylmethyl starch | 4 g | 8 g |
| Polyvidone K30 | 10 g | 11 g |
| magnesium stearate | 1 g | 1 g |

The manufacturing method of capsules containing the Polymorph I or II of Dasatinib or a mixture of the above-mentioned Polymorph I and II in any ratio was: the former four of the above-mentioned excipients were mixed homogeneously with the Polymorph I or II of Dasatinib or a mixture of the above-mentioned two polymorphs in any ratio, and a proper amount of water was added to form damp mass. Then the damp mass was made to be the wet granules and dried. After drying, magnesium stearate was added to be homogeneous mixture, which was capsuled to yield Dasatinib capsules.

Dissolution Curve

| Capsules In Formulation 1 (Polymorph I) | | | | | | | | |
| --- | --- | --- | --- | --- | --- | --- | --- | --- |
| Time | 1# | 2# | 3# | 4# | 5# | 6# | Average % | SD % |
| 0 | 0 | 0 | 0 | 0 | 0 | 0 | 0.00 | 0.00 |
| 5 | 62.3 | 57.9 | 60.1 | 58.6 | 65.4 | 53.3 | 59.6 | 4.12 |
| 10 | 82.6 | 83.9 | 86.7 | 82.8 | 85.1 | 78.4 | 83.3 | 2.82 |
| 20 | 95.3 | 93.1 | 92.4 | 90.2 | 91.9 | 92.2 | 92.5 | 1.67 |
| 30 | 97.8 | 98.9 | 96.5 | 98.7 | 97.4 | 99.3 | 98.1 | 1.06 |
| 45 | 97.3 | 98.1 | 96.0 | 97.8 | 96.6 | 98.1 | 97.3 | 0.86 |
| 60 | 96.7 | 97.5 | 95.7 | 97.3 | 96.1 | 97.9 | 96.9 | 0.85 |

Figure 31:
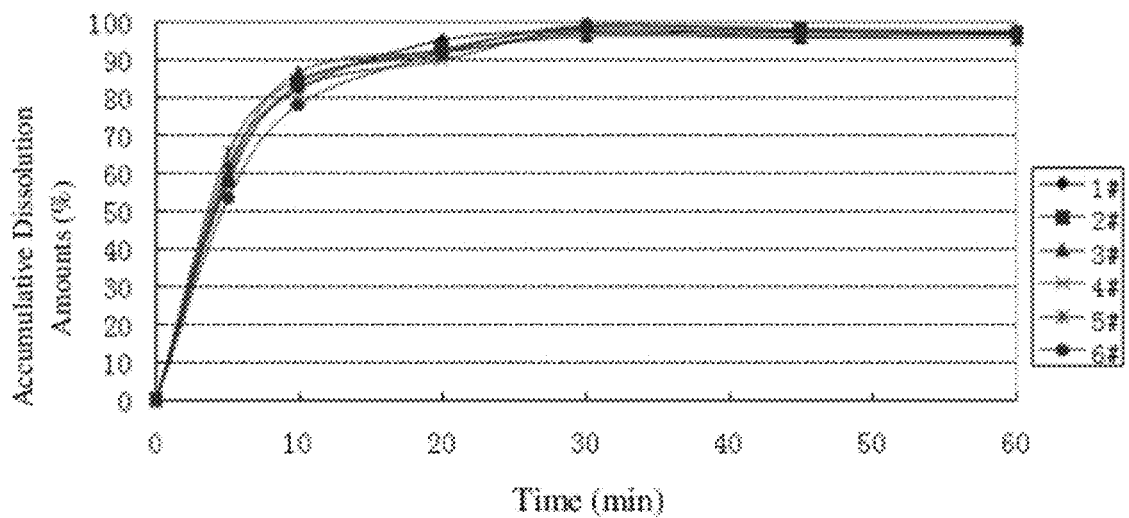
FIG. 31 is a dissolution curve of the Polymorph I and II of Dasatinib Capsules in Formulation 1 of this invention.

Dissolution curve of capsules in Formulation 1 (Batch 1# to Batch 6#) was shown in FIG. 31.

| Capsules Formulation 2 (Polymorph II) | | | | | | | | |
| --- | --- | --- | --- | --- | --- | --- | --- | --- |
| Time | 1# | 2# | 3# | 4# | 5# | 6# | Average % | SD % |
| 0 | 0 | 0 | 0 | 0 | 0 | 0 | 0.00 | 0.00 |
| 5 | 59.9 | 62.7 | 58.1 | 63.5 | 65.2 | 57.7 | 61.2 | 3.07 |
| 10 | 86.9 | 89.5 | 86.1 | 84.2 | 83.3 | 88.7 | 86.5 | 2.44 |
| 20 | 93.4 | 96.7 | 94.8 | 96.5 | 95.6 | 91.2 | 94.7 | 2.10 |
| 30 | 99.5 | 97.6 | 98.1 | 97.3 | 98.8 | 99.7 | 98.5 | 0.99 |
| 45 | 98.6 | 97.2 | 97.6 | 96.4 | 97.5 | 98.8 | 97.7 | 0.90 |
| 60 | 98.1 | 96.3 | 96.7 | 95.9 | 96.6 | 97.4 | 96.8 | 0.79 |

Figure 32:
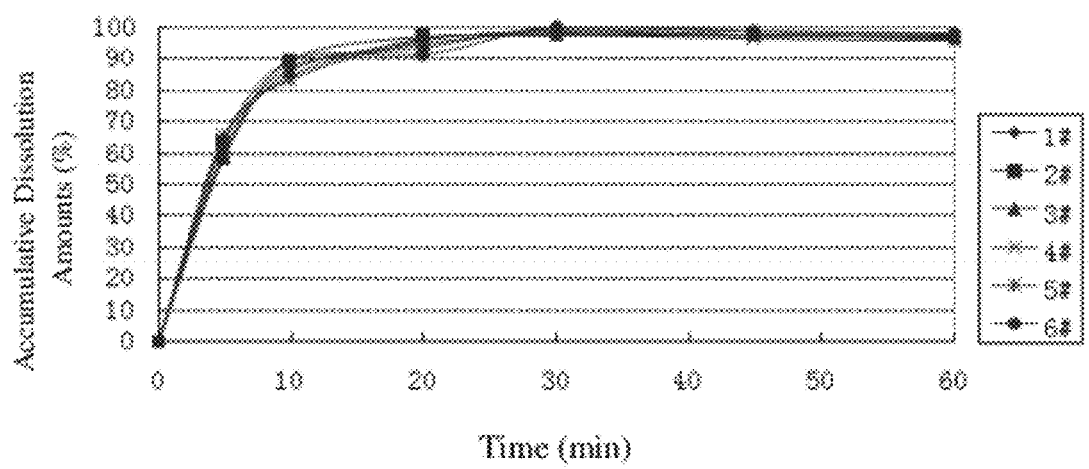
FIG. 32 is a dissolution curve of the Polymorph I and II of Dasatinib Capsules in Formulation 2 of this invention.

Dissolution curve of capsules in Formulation 2 (Batch 1# to Batch 6#) was shown in FIG. 32.

Example 4

Formulation and Preparation Method of Dasatinib Tablets

According to the below-mentioned methods, several excipients and the above-mentioned Polymorph I or II of Dasatinib or a mixture of the Polymorph I, and II in any ratio were formulated into tablets containing 50 mg per tablet.

| | Amount (g/1000 tablets) | |
| --- | --- | --- |
| Active ingredient and Excipients | Formulation 1 | Formulation 2 |
| Dasatinib (I, II) | 50 g | 50 g |
| lactose | 80 g | 65 g |

-continued

| Active ingredient and Excipients | Amount (g/1000 tablets) | |
|---|---|---|
| | Formulation 1 | Formulation 2 |
| microcrystal cellulose | 50 g | 65 g |
| sodium carboxylmethyl starch | 9 g | 8 g |
| Polyvidone K30 | 10 g | 11 g |
| magnesium stearate | 1 g | 1 g |
| opadry | 3 g | 4 g |

The manufacturing method of tablets containing the Polymorph I or II of Dasatinib or a mixture of the above-mentioned Polymorph I and II in any ratio was: the former four of the above-mentioned excipients were mixed homogeneously with the Polymorph I or II of Dasatinib or a mixture of the above-mentioned two polymorphs in any ratio, and a proper amount of water was added to form damp mass. Then the damp mass was made to be the wet granules and dried. The dried granules and magnesium stearate were mixed homogeneously, and then were compressed into tablets, which were coated with opadry to yield Dasatinib tablets.

Dissolution Curve

| Tablets In Formulation 1 (Polymorph I) | | | | | | | | |
|---|---|---|---|---|---|---|---|---|
| Time | 1# | 2# | 3# | 4# | 5# | 6# | Average % | SD % |
| 0 | 0 | 0 | 0 | 0 | 0 | 0 | 0.00 | 0.00 |
| 5 | 45.8 | 40.1 | 47.9 | 42.5 | 48.4 | 42.8 | 44.6 | 3.31 |
| 10 | 75.9 | 78.8 | 74.2 | 79.4 | 77.3 | 76.8 | 77.1 | 1.91 |
| 20 | 88.9 | 86.4 | 88.2 | 87.1 | 87.7 | 91.7 | 88.3 | 1.86 |
| 30 | 95.5 | 94.1 | 93.3 | 94.9 | 96.7 | 97.8 | 95.4 | 1.66 |
| 45 | 98.7 | 97.9 | 97.4 | 96.9 | 98.3 | 99.4 | 98.1 | 0.90 |
| 60 | 97.1 | 97.2 | 96.8 | 96.7 | 97.5 | 98.2 | 97.3 | 0.55 |

Figure 33:
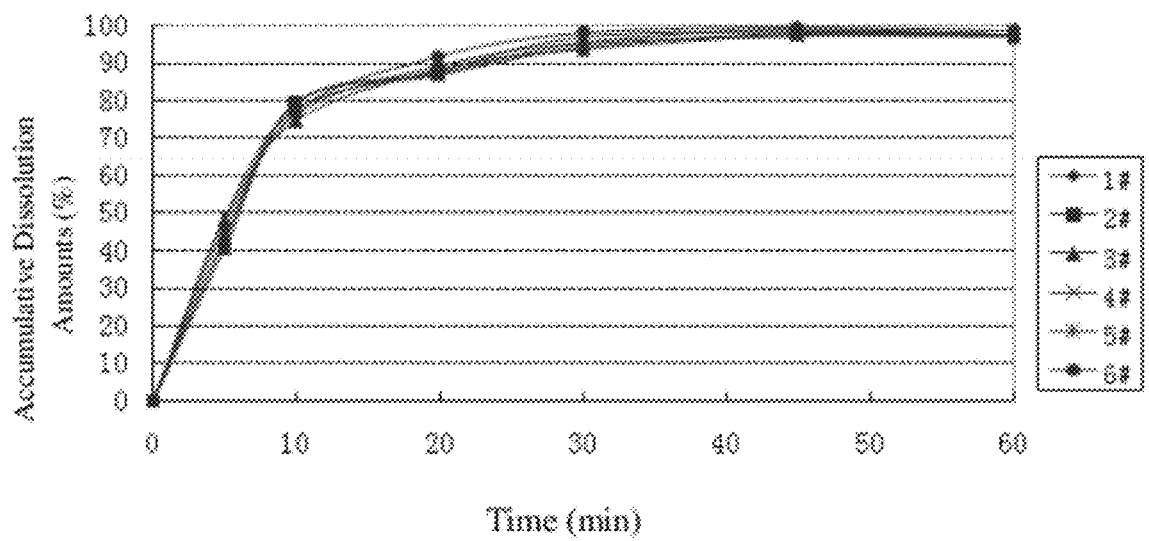
FIG. 33 is a dissolution curve of the Polymorph I and II of Dasatinib Tablets in Formulation 1 of this invention.
Figure 34:
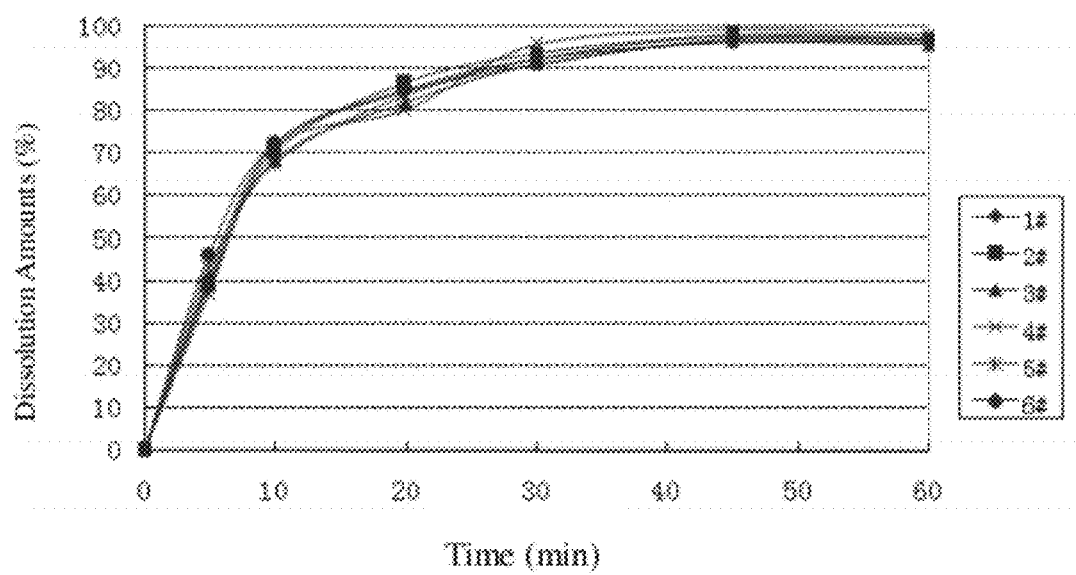
FIG. 34 is a dissolution curve of the Polymorph I and II of Dasatinib Tablets in Formulation 2 of this invention.

Dissolution curve of tablets in Formulation 1 (Batch 1# to Batch 6#) was shown in FIG. 33.

| Tablets In Formulation 2 (Polymorph I) | | | | | | | | |
|---|---|---|---|---|---|---|---|---|
| Time | 1# | 2# | 3# | 4# | 5# | 6# | Average % | SD % |
| 0 | 0 | 0 | 0 | 0 | 0 | 0 | 0.00 | 0.00 |
| 5 | 40.8 | 38.6 | 39.4 | 37.2 | 42.9 | 45.9 | 40.80 | 3.17 |
| 10 | 72.5 | 70.3 | 68.4 | 71.6 | 67.8 | 72.3 | 70.48 | 2.01 |
| 20 | 85.1 | 86.7 | 82.2 | 80.5 | 83.9 | 84.5 | 83.82 | 2.19 |
| 30 | 92.6 | 93.8 | 91.2 | 95.7 | 92.4 | 91.1 | 92.80 | 1.74 |
| 45 | 96.3 | 97.9 | 96.7 | 99.5 | 98.1 | 97.2 | 97.62 | 1.15 |
| 60 | 96.0 | 97.3 | 95.8 | 98.2 | 97.4 | 96.6 | 97.60 | 0.92 |

With the same methods, capsules and tablets containing 20 mg/70 mg/100 mg Dasatinib can be prepared.

Comparative Test on Stability

The methods of destruction experiment of the Polymorph I and II of this invention (hereinafter referred to as 'Polymorph I' and 'Polymorph II') contrasting with the Polymorph A of Dasatinib prepared by the method in CN200580011916.6 (hereinafter referred to as '916.6 Polymorph A') and results of stability are followed:

Table 16 results of stability of 916.6 Polymorph A, Polymorph I and Polymorph II in destruction test

| | Polymorph kind | | | | | |
|---|---|---|---|---|---|---|
| Conditions | 916.6 Polymorph A | | Polymorph I Results | | Polymorph II | |
| before destruction | Total impurities: | 0.07% | Total impurities: | 0.07% | Total impurities: | 0.06% |
| | tR4.135 | 0.02% | tR4.113 | 0.02% | tR4.114 | 0.02% |
| | tR5.092 | 0.02% | tR5.037 | 0.01% | tR5.049 | 0.01% |
| | tR5.523 | 0.03% | tR5.535 | 0.03% | tR5.473 | 0.02% |
| oxidation destruction | Total impurities: | 2.41% | Total impurities: | 1.32% | Total impurities: | 1.19% |
| | tR4.123 | 0.01% | tR3.719 | 0.06% | tR4.393 | 0.02% |
| | tR4.584 | 0.02% | tR4.108 | 0.02% | tR4.567 | 0.03% |
| | tR5.089 | 0.02% | tR4.568 | 0.04% | tR5.090 | 0.01% |
| | tR5.504 | 0.05% | tR5.090 | 0.01% | tR5.510 | 0.07% |
| | tR9.450 | 2.30% | tR5.508 | 0.06% | tR6.468 | 0.04% |
| | | | tR6.467 | 0.05% | tR9.486 | 1.00% |
| | | | tR9.476 | 1.058% | | |
| 1 mol/L acid destruction | Total impurities: | 0.06% | Total impurities: | 0.06% | Total impurities: | 0.06% |
| | tR3.580 | 0.01% | tR4.102 | 0.02% | tR4.101 | 0.01% |
| | tR4.106 | 0.02% | tR4.987 | 0.01% | tR4.993 | 0.01% |
| | tR5.001 | 0.02% | tR5.603 | 0.02% | tR5.604 | 0.02% |
| 1 mol/L alkali estruction | Total impurities: | 0.11% | Total impurities: | 0.08% | Total impurities: | 0.08% |
| | tR4.107 | 0.01% | tR4.130 | 0.02% | tR3.580 | 0.01% |
| | tR5.007 | 0.03% | tR5.089 | 0.01% | tR4.131 | 0.02% |
| | tR5.351 | 0.03% | tR5.501 | 0.02% | tR5.092 | 0.01% |
| | tR8.943 | 0.01% | | | tR5.512 | 0.02% |
| | | | | | tR9.424 | 0.01% |
| illumination destruction | Total impurities: | 1.89% | Total impurities: | 1.28% | Total impurities: | 1.36% |
| | tR2.456 | 0.30% | tR2.199 | 0.04% | tR2.197 | 0.05% |
| | tR3.732 | 0.14% | tR2.527 | 0.06% | tR2.526 | 0.05% |
| | tR4.589 | 0.11% | tR2.911 | 0.33% | tR2.910 | 0.02% |
| | tR5.088 | 0.06% | tR3.734 | 0.11% | tR3.733 | 0.11% |
| | tR5.503 | 0.19% | tR4.119 | 0.04% | tR4.116 | 0.04% |

-continued

| Conditions | Polymorph kind | | | | | |
|---|---|---|---|---|---|---|
| | 916.6 Polymorph A | | Polymorph I Results | | Polymorph II | |
| | tR10.095 | 0.82% | tR4.585 | 0.08% | tR4.582 | 0.07% |
| | | | tR5.089 | 0.03% | tR5.084 | 0.02% |
| | | | tR5.502 | 0.14% | tR5.496 | 0.15% |
| | | | tR5.996 | 0.08% | tR5.990 | 0.06% |
| | | | tR10.096 | 0.66% | tR10.084 | 0.78% |
| high temperature destruction | Total impurities: | 0.08% | Total impurities: | 0.05% | Total impurities: | 0.06% |
| | tR4.118 | 0.02% | tR3.569 | 0.01% | tR3.567 | 0.01% |
| | tR5.081 | 0.03% | tR4.120 | 0.02% | tR4.117 | 0.01% |
| | tR5.502 | 0.03% | tR5.088 | 0.01% | tR5.085 | 0.01% |
| | | | tR5.520 | 0.02% | tR5.507 | 0.02% |

Procedure:

Oxidation destruction: 50 mg of sample weighted accurately was added into measuring flask of 100 mL, and 10 mL 30% $H_2O_2$ was added. After standing at room temperature for 2 hour, the mixture was diluted with mobile phase to scale and shook to be homogeneous, and determined by HPLC.

Acid destruction: 50 mg of sample weighted accurately was added into measuring flask of 100 mL, and 10 mL 1 mol/L HCl solution was added. After standing at 40° C. for 1 hour, an equal amount of 1 mol/L NaOH solution was added for neutralization. Then the mixture was diluted with mobile phase to scale and shook to be homogeneous, and determined by HPLC.

Alkali destruction: 50 mg of sample weighted accurately was added into measuring flask of 100 mL, and 10 mL 1 mol/L NaOH solution was added. After standing at 40° C. for 1 hour, an equal amount of 1 mol/L HCl solution was added for neutralization. Then the mixture was diluted with mobile phase to scale and shook to be homogeneous, and determined by HPLC.

Illumination destruction: 50 mg of sample weighted accurately was added into measuring flask of 100 mL, dissolved and diluted with mobile phase to be the solution containing 0.5 mg Dasatinib per milliliter. After standing under illumination of 4000 lx for 6 hour, the mixture was determined by HPLC.

High temperature destruction: 50 mg of sample weighted accurately was added into measuring flask of 100 mL, dissolved and diluted with mobile phase to be the solution containing 0.5 mg Dasatinib per milliliter. After standing in homothermal water bath of 60° C. for 4 hour, the mixture was cooled and then determined by HPLC.

Related Substances Determination

HPLC conditions and system applicability: octadecylsilane bonded silica as the filler; 0.05 mol/L of potassium dihydrogen phosphate (adjusted to pH 2.5 by phosphoric acid, 0.2% triethylamine)-methanol (45:55) as the mobile phase; detection wavelength was 230 nm; the number of theoretical plates should be not less than 2000, calculated according to the peak of Dasatinib. The resolution of the peak of Dasatinib from the peaks of adjacent impurities should meet requirements.

Determination method: sample was dissolved in mobile phase to be the solution containing 0.5 mg per milliliter. 20 μL of such solution was injected into liquid chromatograph, and chromatogram was recorded until the sixfold retention time of major component peak. If there were impurities peaks in the chromatogram of sample solution, total impurities and any single impurity were calculated by normalization method on the basis of peak area.

Stability of Polymorph in the Formulations

The XRPD patterns of capsules and tablets respectively prepared in the Example 3 and Example 4 have been tested, and compared with XRPD characteristic peaks of Polymorph I of Dasatinib prepared by the Method A in the Example 1 in the present invention, as listed in the following table:

| Bulk Drug (Polymorph I) 2θ | Capsules 1 (Polymorph I) 2θ | Capsules 2 (Polymorph I) 2θ | Tablets 1 (Polymorph I) 2θ | Tablets 2 (Polymorph I) 2θ |
|---|---|---|---|---|
| 9.060 | 9.080 | 9.070 | 9.060 | 9.070 |
| 11.100 | 11.120 | 11.110 | 11.100 | 11.110 |
| 13.640 | 13.670 | 13.650 | 13.640 | 13.650 |
| 15.100 | 15.120 | 15.110 | 15.100 | 15.110 |
| 17.820 | 17.840 | 17.830 | 17.820 | 17.820 |
| 19.380 | 19.400 | 19.390 | 19.380 | 19.390 |
| 22.940 | 22.970 | 22.950 | 22.950 | 22.950 |

The results in the above-mentioned comparative table have shown that the crystal form had substantially no change after Polymorph I of Dasatinib in the invention were prepared into capsules or tablets by the formulation process.

In addition, The relative substances of capsules and tablets respectively prepared in the Example 3 and Example 4 have been tested, and compared with those of Polymorph I of Dasatinib prepared by the Method A in the Example 1 in the present invention, as listed in the following table:

| Bulk Drug (Polymorph I) | Capsules 1 | Capsules 2 | Tablets 1 | Tablets 2 |
|---|---|---|---|---|
| 0.07% | 0.08% | 0.08% | 0.07% | 0.08% |

The results in the above-mentioned comparative table have shown that the Polymorph I of Dasatinib was stable, and there were no significantly changes in respect to the relative substances, after Polymorph I of Dasatinib in the invention were prepared into capsules or tablets by the formulation process.

INDUSTRIAL APPLICATION

The present invention provides novel polymorphs of Dasatinib, preparing methods, and pharmaceutical composition comprising them. These polymorphs have better physicochemical properties, are more stable and are more suitable for industrial scale production, furthermore, are suitable for long-term storage, and are advantageous to meet the requirements of formulation process and long-term storage of formulations. The preparation technique of this invention was simple, quite easy for operation and convenient for industrial production, and the quality of the products was controllable with paralleled yields. In addition, by the methods of polymorph preparation in this invention, the amount of organic solvent used in crystal transformation could be reduced greatly, which led to reduced cost of products; organic solvents in Class III with low toxicity could be used selectively to prepare the polymorphs of this invention, reducing the toxic effects of the organic solvents potentially on human body to some extent.

The invention claimed is:

1. A Polymorph I of Dasatinib monohydrate, characterized by diffraction peaks at 9.1±0.2, 11.1±0.2, 13.7±0.2, 15.1±0.2, 17.8±0.2, 23.0±0.2 and 19.4±0.2 of 2θ indicated with degree in its X-ray powder diffraction pattern using Cu-Ka radiation.

2. The Polymorph I according to claim 1, wherein its X-ray powder diffraction pattern includes the following diffraction peaks:

3. The Polymorph I according to claim 1, having the first endothermic peak at about 100~130° C., and the second endothermic transform at about 284~290° C. in its DSC diagram.

4. The polymorph I according to claim 1, characterized by absorption peaks at about 3462.42 $cm^{-1}$, 3210.67 $cm^{-1}$, 3003.96 $cm^{-1}$, 2954.14 $cm^{-1}$, 2823.49 $cm^{-1}$, 1682.15 $cm^{-1}$, 1629.58 $cm^{-1}$, 1612.25 $cm^{-1}$, 1583.84 $cm^{-1}$, 1305.47 $cm^{-1}$, 1290.91 $cm^{-1}$, 1000.19 $cm^{-1}$ and 1040.60 $cm^{-1}$ in its infrared spectrum in KBr disc.

5. The polymorph I according to claim 1, characterized by chemical shifts at about 16.75±0.2 ppm, 24.92±0.2 ppm, 41.72±0.2 ppm, 43.23±0.2 ppm, 44.28±0.2 ppm, 54.01±0.2 ppm, 55.48±0.2 ppm, 57.53±0.2 ppm, 58.70±0.2 ppm, 62.23±0.2 ppm, 63.20±0.2 ppm, 84.66±0.2 ppm, 127.92±0.2 ppm, 128.81±0.2 ppm, 132.70±0.2 ppm, 137.68±0.2 ppm, 139.00±0.2 ppm, 157.17±0.2 ppm, 162.07±0.2 ppm, 163.54±0.2 ppm, 166.84±0.2 ppm and 167.58±0.2 ppm in its $^{13}C$ solid-state NMR spectrum.

6. A preparation method of the Polymorph I of claim 1 includes the following steps:
   1) Dasatinib is added into dimethylformamide or dimethylsulfoxide;
   2) dissolved by stirring and heating;
   3) a mixed solvent system of water and an organic solvent is added; wherein, the organic solvent is one kind of solvent or a mixed solvent of several kinds, to which Dasatinib is insoluble or slightly soluble;
   4) after finish adding, it is heat-preserved and then cooled down slowly to 0-5° C. with stirring to make crystal precipitated completely and grow the grain;
   5) after filtration, the solid is collected and dried.

7. A pharmaceutical composition comprising Polymorph I of Dasatinib monohydrate of claim 1.

8. The Polymorph I according to claim 2, having the first endothermic peak at about 100~130° C., and the second endothermic transform at about 284~290° C. in its DSC diagram.

9. The polymorph I according to claim 2, characterized by absorption peaks at about 3462.42 $cm^{-1}$, 3210.67 $cm^{-1}$, 3003.96 $cm^{-1}$, 2954.14 $cm^{-1}$, 2823.49 $cm^{-1}$, 1682.15 $cm^{-1}$, 1629.58 $cm^{-1}$, 1612.25 $cm^{-1}$, 1583.84 $cm^{-1}$, 1305.47 $cm^{-1}$, 1290.91 $cm^{-1}$, 1000.19 $cm^{-1}$ and 1040.60 $cm^{-1}$ in its infrared spectrum in KBr disc.

10. The polymorph I according to claim 2, characterized by chemical shifts at about 16.75±0.2 ppm, 24.92±0.2 ppm, 41.72±0.2 ppm, 43.23±0.2 ppm, 44.28±0.2 ppm, 54.01±0.2 ppm, 55.48±0.2 ppm, 57.53±0.2 ppm, 58.70±0.2 ppm, 62.23±0.2 ppm, 63.20±0.2 ppm, 84.66±0.2 ppm, 127.92±0.2 ppm, 128.81±0.2 ppm, 132.70±0.2 ppm, 137.68±0.2 ppm, 139.00±0.2 ppm, 157.17±0.2 ppm, 162.07±0.2 ppm, 163.54±0.2 ppm, 166.84±0.2 ppm and 167.58±0.2 ppm in its $^{13}C$ solid-state NMR spectrum.

* * * * *